US010538568B2

(12) United States Patent
Powell, Jr. et al.

(10) Patent No.: US 10,538,568 B2
(45) Date of Patent: Jan. 21, 2020

(54) METHODS AND COMPOSITIONS OF A FOLLICLE STIMULATING HORMONE RECEPTOR IMMUNORECEPTOR

(71) Applicant: The Trustees of the University of Pennsylvania, Philadelphia, PA (US)

(72) Inventors: Daniel J. Powell, Jr., Bala Cynwyd, PA (US); Caitlin Stashwick, Philadelphia, PA (US); Katarzyna Urbanska, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 15/524,158

(22) PCT Filed: Nov. 3, 2015

(86) PCT No.: PCT/US2015/058797
§ 371 (c)(1),
(2) Date: May 3, 2017

(87) PCT Pub. No.: WO2016/073456
PCT Pub. Date: May 12, 2016

(65) Prior Publication Data
US 2018/0057557 A1    Mar. 1, 2018

Related U.S. Application Data

(60) Provisional application No. 62/074,893, filed on Nov. 4, 2014, provisional application No. 62/074,930, filed on Nov. 4, 2014, provisional application No. 62/144,159, filed on Apr. 7, 2015.

(51) Int. Cl.
*C07K 14/59* (2006.01)
*C07K 14/725* (2006.01)
*A61K 38/00* (2006.01)

(52) U.S. Cl.
CPC .............. *C07K 14/59* (2013.01); *A61K 38/00* (2013.01); *C07K 14/7051* (2013.01); *C07K 2319/03* (2013.01); *C07K 2319/74* (2013.01)

(58) Field of Classification Search
None
See application file for complete search history.

(56) References Cited

U.S. PATENT DOCUMENTS

| 2002/0165146 | A1  | 11/2002 | Hoffman et al. | |
| 2006/0067920 | A1* | 3/2006  | Jensen ............... | C07K 14/5437 424/93.21 |
| 2010/0316572 | A1* | 12/2010 | Ghinea ............ | G01N 33/57434 424/9.1 |
| 2014/0161767 | A1  | 6/2014  | Leuschner et al. | |

OTHER PUBLICATIONS

Accession EF198021. Jan. 28, 2007 (Year: 2007).*
Accession BC111848. Jan. 3, 2008 (Year: 2008).*
Singh et al. Curr Protein Pept Sci. 2017, 18, 1-11 (Year: 2017).*
International Search Report and Written Opinion for PCT International Application No. PCT/US2015/058797 dated Mar. 28, 2016.

Abel, et al., "Spermatogenesis and Sertoli cell activity in mice lacking Sertoli cell receptors for follicle stimulating hormone and androgen", Endocrinology. 149(7), 2008, 3279-3285.
Bierer, et al., "Cyclosporin A and FK506: molecular mechanisms of immunosuppression and probes for transplantation biology", Current Opinion in Immunology 5, 1993, 763-773.
Carpenito, et al., "Control of large, established tumor xenografts with genetically retargeted human T cells containing CD28 and CD137 domains", PNAS 106(9):, 2009, 3360-3365.
Dierich, et al., "Impairing follicle-stimulating hormone (FSH) signaling in vivo: targeted disruption of the FSH receptor leads to aberrant gametogenesis and hormonal imbalance", Proc Natl Acad Sci U S A. 95(23), 1998, 13612-13617.
Fong, et al., "Ovarian cancer mouse models: a summary of current models and their limitations", J Ovarian Res. 2(1), 2009, 12.
Grasso, et al., "In vivo effects of follicle-stimulating hormone-related synthetic peptides on the mouse estrous cycle", Endocrinology. 137(12), 1996, 5370-5375.
Grasso, et al., "In vivo effects of human follicle-stimulating hormone-related synthetic peptide hFSH-beta-(81-95) and its subdomain hFSH-beta-(90-95) on the mouse estrous cycle", Biol Reprod. 58(3), 1998, 821-825.
Henderson, et al., "Comparison of the effects of FK-506, cyclosporin A and rapamycin on IL-2 production", Immunology 73, 1991, 316-321.
Hudecek, et al., "The non-signaling extracellular spacer domain of chimeric antigen receptors is decisive for in vivo antitumor activity", Cancer Immunol Res. 3(2), 2015, 125-135.
Jiang, et al., "Structure of follicle-stimulating hormone in complex with the entire ectodomain of its receptor", Proc Natl Acad Sci U S A. 109(31), 2012, 12491-12496.
Lanitis, et al., "Redirected Antitumor Activity of Primary Human Lymphocytes Transduced With a Fully Human Anti-mesothelin Chimeric Receptor", Molecular Therapy, 20(3), 2012, 633-643.
Li, et al., "FSH stimulates ovarian cancer cell growth by action on growth factor variant receptor", Mol Cell Endocrinol. 267(1-2), 2007, 26-37.
Liu, et al., "Calcineurin Is a Common Target of Cyclophilin-Cyclosporin A and FKBP-FK506 Complexes", Cell 66, 1991, 807-815.
Lum, et al., "Phase I/II study of treatment of stage Iv breast cancer with OKT3 x trastuzumab-armed activated T cells", Clin Breast Cancer 4(3), 2003, 212-217.
Morbeck, et al., "A receptor binding site identified in the region 81-95 of the beta-subunit of human luteinizing hormone (LH) and chorionic gonadotropin (hCG)", Mol Cell Endocrinol. 97(1-2), 1993, 173-181.
Radu, et al., "Expression of follicle-stimulating hormone receptor in tumor blood vessels", N Engl J Med. 363(17), 2010, 1621-1630.
Renner, et al., "Follicle-stimulating hormone receptor expression in soft tissue sarcomas", Histopathology. 63(1), 2013, 29-35 (Abstract Only).
Robbins, et al., "Cutting edge: persistence of transferred lymphocyte clonotypes correlates with cancer regression in patients receiving cell transfer therapy", J Immunol. 173(12), 2004, 7125-7130.

(Continued)

*Primary Examiner* — Christian L Fronda
(74) *Attorney, Agent, or Firm* — Saul Ewing Arnstein & Lehr LLP; Kathryn Doyle

(57) ABSTRACT

The present invention relates to compositions and methods for diagnosing and treating diseases, disorders or conditions associated with dysregulated expression of FSHR. The invention provides novel peptides that specifically bind to Follicle-stimulation hormone receptor (FSHR).

12 Claims, 32 Drawing Sheets

Specification includes a Sequence Listing.

(56) References Cited

OTHER PUBLICATIONS

Robinson, et al., "FSH-Receptor Isoforms and FSH-dependent Gene Transcription in Human Monocytes and Osteoclasts", Biochem Biophys Res Commun. 394(1), 2010, 12-17.
Siraj, et al., "Expression of follicle-stimulating hormone receptor by the vascular endothelium in tumor metastases", BMC Cancer 13, 2013, 246.
Song, et al., "CD27 costimulation augments the survival and antitumor activity of redirected human T cells in vivo", Blood 119(3), 2012, 696-706.
Song, et al., "Chimeric NKG2D Car-expressing T cell-mediated attack of human ovarian cancer is enhanced by histone deacetylase inhibition", Hum Gene Ther. 24(3), 2013, 295-305.
Song, et al., "In vivo persistence, tumor localization, and antitumor activity of CAR-engineered T cells is enhanced by costimulatory signaling through CD137 (4-1BB)", Cancer Res. 71(13), 2011, 4617-4627.
Zhang, et al., "Follicle-stimulating hormone peptide can facilitate paclitaxel nanoparticles to target ovarian carcinoma in vivo", Cancer Res. 69(16), 2009, 6506-6514.

\* cited by examiner

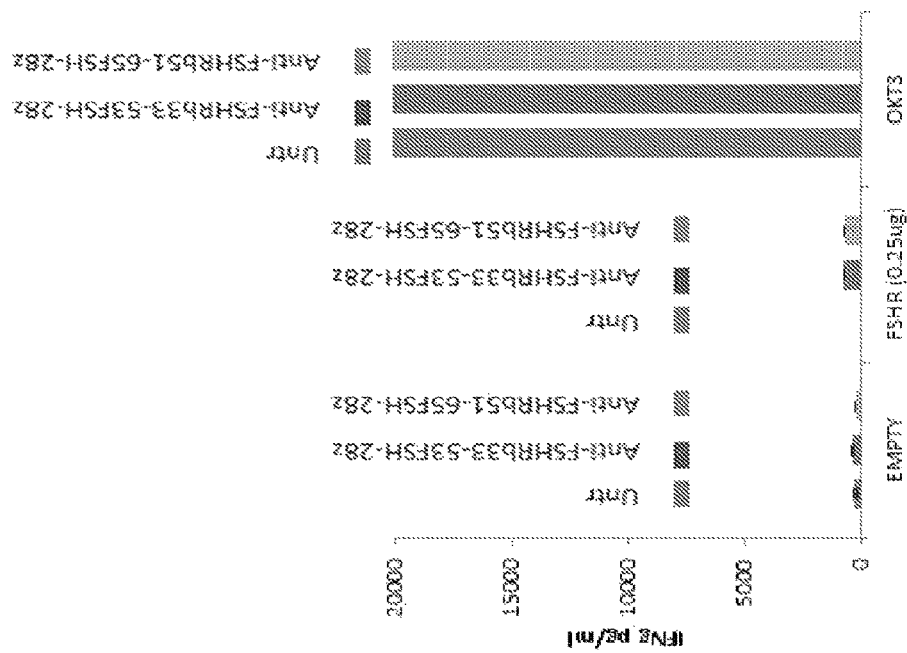
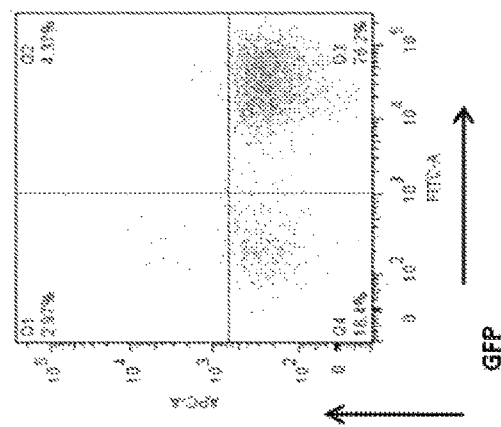
Fig. 3A
Fig. 3B

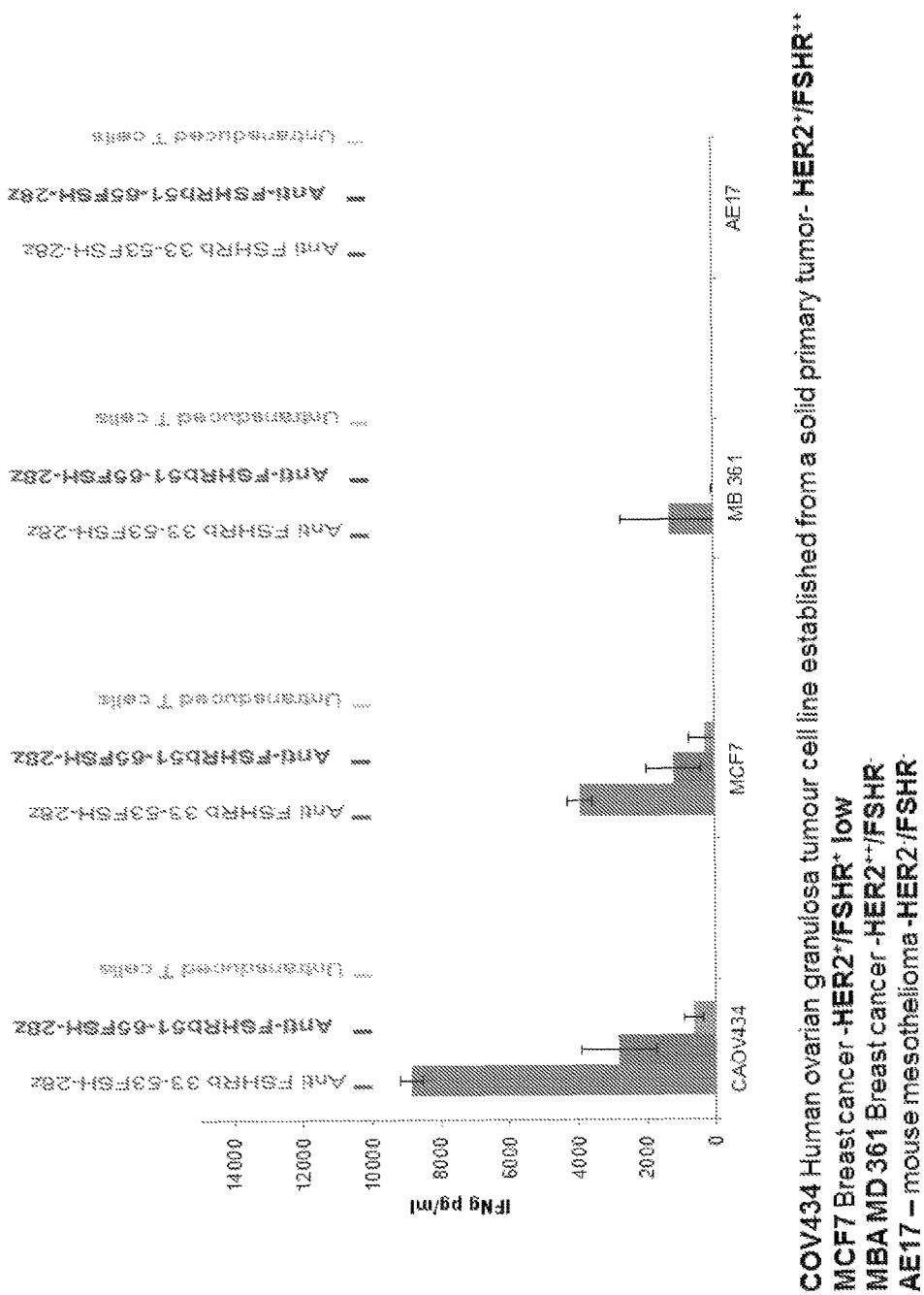

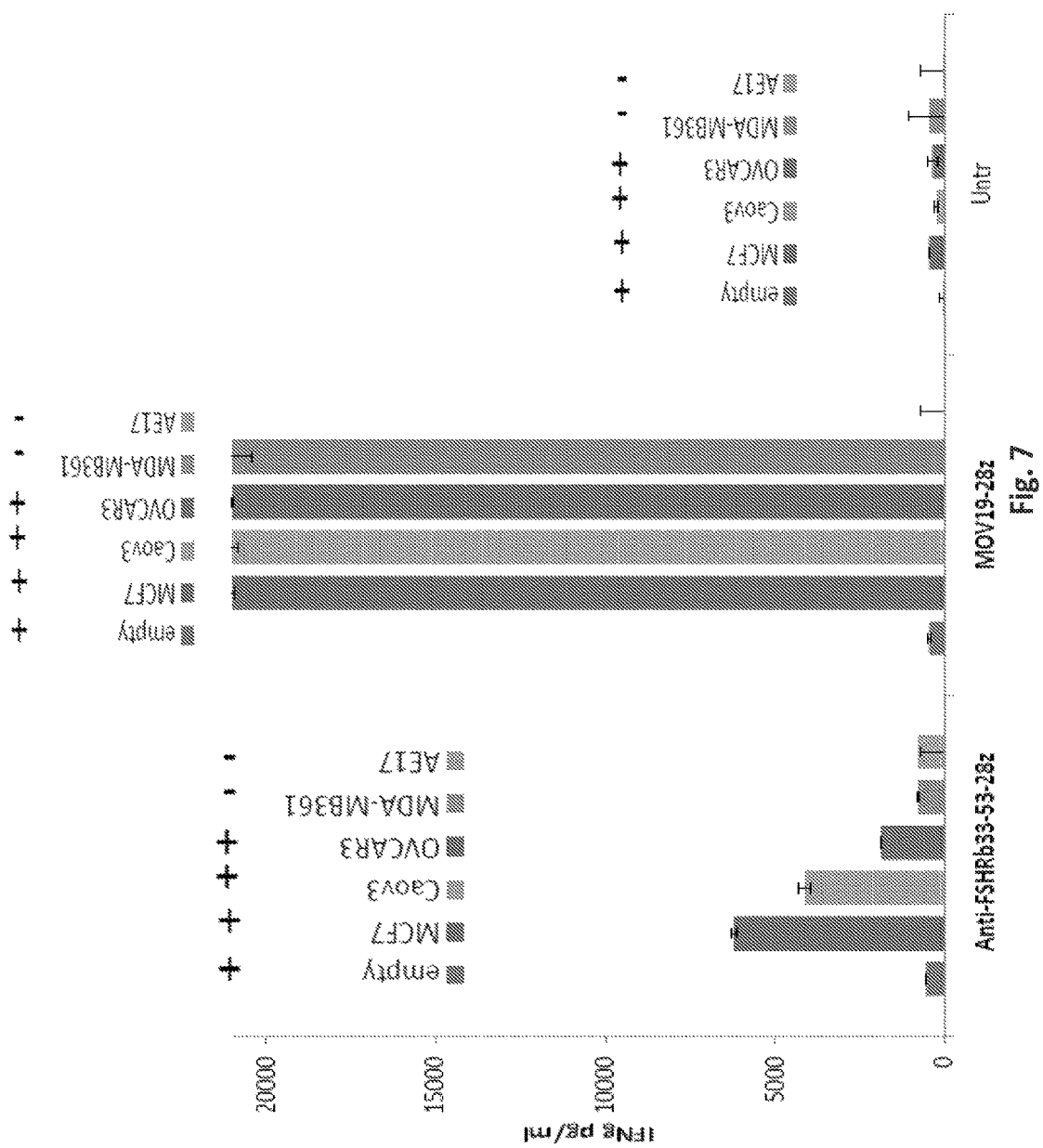

| SEQ ID NO: | FSH-derived peptides | Sequence/Name | Predicted affinity | Predicted cross-reactivity |
|---|---|---|---|---|
| 1 | β33-53 aa | YTRDLVYKDPARPKIQKTCTF<br>Anti-FSHRb33-53FSH-28z | $10^{-5}$M | Human /Mouse |
| 2 | β51–65 aa | CTFKELVYETVRVPGC<br>Anti-FSHRb51-65FSH-28z | $10^{-4}$M | Human |
| 3 | β81-95 aa | QCHCGKCDSDSTDCT<br>Anti-FSHRb51-65FSH-28z | $10^{-5}$M | Human/Mouse |
| 4 | Antagonist A β(87-94aa)+α(25-42aa) | CDSDSTDCILQCMGCCFSRAYPTPLR<br>Anti-FSHRantagonistA-28Z | $10^{-8}$M | Human/Mouse |
| 5 | Agonist A β(87-94aa)+α(25-42aa)+β(27-45aa) | CDSDSTDCILQCMGCCFSRAYPTPLR<br>WCAGYCYCYTRDVKDPARP<br>Anti-FSHRantagonistA-28Z | $10^{-7}$M | Human/Mouse |
| | FSH (alpha + beta) linear | GenBank Gene IDs: 1081 (follicle stimulating hormone, alpha subunit) + 2488 (follicle stimulating hormone, beta subunit) Anti-FSHRalpha+beta-28Z | NA | Human/Mouse |
| | α(25-42aa) + β(87-94aa) | Anti-FSHRantagonistB-28Z | | |
| | β(87-94aa)+α(25-42aa)+β(27-45aa) | Anti-FSHRagonistB-28Z | | |

```
                              SEQUENCE LISTING

<160> NUMBER OF SEQ ID NOS: 31

<210> SEQ ID NO 1
<211> LENGTH: 21
<212> TYPE: PRT
<213> ORGANISM: Artificial Sequence
<220> FEATURE:
<223> OTHER INFORMATION: Synthetic sequence

<400> SEQUENCE: 1

Tyr Thr Arg Asp Leu Val Tyr Lys Asp Pro Ala Arg Pro Lys Ile Gln
1               5                   10                  15

Lys Thr Cys Thr Phe
            20

<210> SEQ ID NO 2
<211> LENGTH: 16
<212> TYPE: PRT
<213> ORGANISM: Artificial Sequence
<220> FEATURE:
<223> OTHER INFORMATION: Synthetic sequence

<400> SEQUENCE: 2

Cys Thr Phe Lys Glu Leu Val Tyr Glu Thr Val Arg Val Pro Gly Cys
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Synthetic sequence

<400> SEQUENCE: 3

Gln Cys His Cys Gly Lys Cys Asp Ser Asp Ser Thr Asp Cys Thr
1               5                   10                  15

<210> SEQ ID NO 4
<211> LENGTH: 26
<212> TYPE: PRT
<213> ORGANISM: Artificial Sequence
<220> FEATURE:
```

<223> OTHER INFORMATION: Synthetic sequence

<400> SEQUENCE: 4

Cys Asp Ser Asp Ser Thr Asp Cys Ile Leu Gln Cys Met Gly Cys Cys
1               5                   10                  15

Phe Ser Arg Ala Tyr Pro Thr Pro Leu Arg
            20                  25

<210> SEQ ID NO 5
<211> LENGTH: 45
<212> TYPE: PRT
<213> ORGANISM: Artificial Sequence
<220> FEATURE:
<223> OTHER INFORMATION: Synthetic sequence

<400> SEQUENCE: 5

Cys Asp Ser Asp Ser Thr Asp Cys Ile Leu Gln Cys Met Gly Cys Cys
1               5                   10                  15

Phe Ser Arg Ala Tyr Pro Thr Pro Leu Arg Trp Cys Ala Gly Tyr Cys
            20                  25                  30

Tyr Cys Tyr Thr Arg Asp Val Lys Asp Pro Ala Arg Pro
        35                  40                  45

<210> SEQ ID NO 6
<211> LENGTH: 57
<212> TYPE: DNA
<213> ORGANISM: Artificial Sequence
<220> FEATURE:
<223> OTHER INFORMATION: Synthetic sequence

<400> SEQUENCE: 6
tacaccaggg atctggtgta taaggaccca gccaggccca aaatccagaa aacatgt        57

<210> SEQ ID NO 7
<211> LENGTH: 19
<212> TYPE: PRT
<213> ORGANISM: Artificial Sequence
<220> FEATURE:
<223> OTHER INFORMATION: Synthetic sequence

<400> SEQUENCE: 7

Tyr Thr Arg Asp Leu Val Tyr Lys Asp Pro Ala Arg Pro Lys Ile Gln
1               5                   10                  15

Lys Thr Cys

<210> SEQ ID NO 8
<211> LENGTH: 45
<212> TYPE: DNA
<213> ORGANISM: Artificial Sequence
<220> FEATURE:
<223> OTHER INFORMATION: Synthetic sequence

<400> SEQUENCE: 8
aaaacatgta ccttcaagga actggtatac gaaacagtga gagtg                    45

<210> SEQ ID NO 9
<211> LENGTH: 15
<212> TYPE: PRT
<213> ORGANISM: Artificial Sequence
<220> FEATURE:
<223> OTHER INFORMATION: Synthetic sequence

<400> SEQUENCE: 9

Lys Thr Cys Thr Phe Lys Glu Leu Val Tyr Glu Thr Val Arg Val

<210> SEQ ID NO 10
<211> LENGTH: 57
<212> TYPE: DNA
<213> ORGANISM: Artificial Sequence
<220> FEATURE:
<223> OTHER INFORMATION: Synthetic sequence

<400> SEQUENCE: 10
ggatcccagt gtcactgtgg caagtgtgac agcgacagca ctgattgtac tgctagc    57

<210> SEQ ID NO 11
<211> LENGTH: 19
<212> TYPE: PRT
<213> ORGANISM: Artificial Sequence
<220> FEATURE:
<223> OTHER INFORMATION: Synthetic sequence

<400> SEQUENCE: 11

Gly Ser Gln Cys His Cys Gly Lys Cys Asp Ser Asp Ser Thr Asp Cys
1               5                   10                  15

Thr Ala Ser

<210> SEQ ID NO 12
<211> LENGTH: 89
<212> TYPE: DNA
<213> ORGANISM: Artificial Sequence
<220> FEATURE:
<223> OTHER INFORMATION: Synthetic sequence

<400> SEQUENCE: 12
gatcctgcga tagcgatagc accgattgca ttctgcagtg catgggctgc tgctttagcc    60
gcgcgtatcc gaccccgctg cgcgctagc                                     89

<210> SEQ ID NO 13
<211> LENGTH: 30
<212> TYPE: PRT
<213> ORGANISM: Artificial Sequence
<220> FEATURE:
<223> OTHER INFORMATION: Synthetic sequence

<400> SEQUENCE: 13

Gly Ser Cys Asp Ser Asp Ser Thr Asp Cys Ile Leu Gln Cys Met Gly
1               5                   10                  15

Cys Cys Phe Ser Arg Ala Tyr Pro Thr Pro Leu Arg Ala Ser
            20                  25                  30

<210> SEQ ID NO 14
<211> LENGTH: 90
<212> TYPE: DNA
<213> ORGANISM: Artificial Sequence
<220> FEATURE:
<223> OTHER INFORMATION: Synthetic sequence

<400> SEQUENCE: 14
ggatcccgcc tgccgacccc gtatgcgcgc agcttttgct gcggcatgtg ccagctgatt    60
tgcgatacca gcgatagcga ttgcgctagc                                     90

<210> SEQ ID NO 15
<211> LENGTH: 30
<212> TYPE: PRT
<213> ORGANISM: Artificial Sequence
<220> FEATURE:

```
<223> OTHER INFORMATION: Synthetic sequence

<400> SEQUENCE: 15

Gly Ser Arg Leu Pro Thr Pro Tyr Ala Arg Ser Phe Cys Cys Gly Met
1               5                   10                  15

Cys Gln Leu Ile Cys Asp Thr Ser Asp Ser Asp Cys Ala Ser
            20                  25                  30

<210> SEQ ID NO 16
<211> LENGTH: 300
<212> TYPE: DNA
<213> ORGANISM: Artificial Sequence
<220> FEATURE:
<223> OTHER INFORMATION: Synthetic sequence

<400> SEQUENCE: 16
ggatcctgcg atagcgatag caccgattgc attctgcagt gcatgggctg cctaggacgc     60
tatcgctatc gtggctaacg taagacgtca cgtacccgac ctgctttagc cgcgcgtatc   120
cgaccccgct gcgctggtgc gcgggctatt gacgaaatcg gcgcgcatag gctggggcga   180
cgcgaccacg cgcccgataa gctattgcta tacccgcgat ctggtgaaag atccggcgcg   240
cccggctagc cgataacgat atgggcgcta gaccactttc taggccgcgc gggccgatcg   300

<210> SEQ ID NO 17
<211> LENGTH: 50
<212> TYPE: PRT
<213> ORGANISM: Artificial Sequence
<220> FEATURE:
<223> OTHER INFORMATION: Synthetic sequence

<400> SEQUENCE: 17

Gly Ser Cys Asp Ser Asp Ser Thr Asp Cys Ile Leu Gln Cys Met Gly
1               5                   10                  15

Cys Cys Phe Ser Arg Ala Tyr Pro Thr Pro Leu Arg Trp Cys Ala Gly
            20                  25                  30

Tyr Cys Tyr Cys Tyr Thr Arg Asp Leu Val Lys Asp Pro Ala Arg Pro
        35                  40                  45

Ala Ser
    50

<210> SEQ ID NO 18
<211> LENGTH: 295
<212> TYPE: DNA
<213> ORGANISM: Artificial Sequence
<220> FEATURE:
<223> OTHER INFORMATION: Synthetic sequence

<400> SEQUENCE: 18
cccgcgcgcg ccggataaag tgctggatcg cacctattgc tattgcctag gggcgcgcgc     60
ggcctatttc acgacctagc gtggataacg ataacctatg gcgcgtgctg gcgcctgccg   120
accccgtatg cgcgcagctt ttgctgatac cgcgcacgac cgcggacggc tggggcatac   180
gcgcgtcgaa aacgagcggc atgtgccagc tgatttgcga taccagcgat agcgattgcg   240
ctagccgccg tacacggtcg actaaacgct atggtcgcta tcgctaacgc gatcg         295

<210> SEQ ID NO 19
<211> LENGTH: 46
<212> TYPE: PRT
<213> ORGANISM: Artificial Sequence
<220> FEATURE:
<223> OTHER INFORMATION: Synthetic sequence
```

<400> SEQUENCE: 19

Pro Arg Ala Pro Asp Lys Val Leu Asp Arg Thr Tyr Cys Tyr Cys Tyr
1               5                   10                  15

Gly Ala Cys Trp Arg Leu Pro Thr Pro Tyr Ala Arg Ser Phe Cys Cys
                20                  25                  30

Gly Met Cys Gln Leu Ile Cys Asp Thr Ser Asp Ser Asp Cys
            35                  40                  45

<210> SEQ ID NO 20
<211> LENGTH: 621
<212> TYPE: DNA
<213> ORGANISM: Artificial Sequence
<220> FEATURE:
<223> OTHER INFORMATION: Synthetic sequence

<400> SEQUENCE: 20

```
ggatccaaca gctgcgaact gaccaacatt accattgcga ttgaaaaaga agaatgccgc      60
ttttgcatta gcattaacac cacctggtgc gcgggctatt gctataccccg cgatctggtg    120
tataaagatc cggcgcgccc gaaaattcag aaaacctgca cctttaaaga actggtgtat    180
gaaaccgtgc gcgtgccggg ctgcgcgcat catgcggata gcctgtatac ctatccggtg    240
gcgacccagt gccattgcgg caaatgcgat agcgatagca ccgattgcac cgtgcgcggc    300
ctgggcccga gctattgcag ctttggcgaa atgaaagaag cgccggatgt gcaggattgc    360
ccggaatgca ccctgcagga aaacccgttt tttagccagc cgggcgcgcc gattctgcag    420
tgcatgggct gctgctttag ccgcgcgtat ccgaccccgc tgcgcagcaa aaaaaccatg    480
ctggtgcaga aaacgtgac cagcgaaagc acctgctgcg tggcgaaaag ctataaccgc    540
gtgaccgtga tgggcggctt taaagtggaa accataccg cgtgccattg cagcacctgc    600
tattatcata aaagcgctag c                                              621
```

<210> SEQ ID NO 21
<211> LENGTH: 207
<212> TYPE: PRT
<213> ORGANISM: Artificial Sequence
<220> FEATURE:
<223> OTHER INFORMATION: Synthetic sequence

<400> SEQUENCE: 21

Gly Ser Asn Ser Cys Glu Leu Thr Asn Ile Thr Ile Ala Ile Glu Lys
1               5                   10                  15

Glu Glu Cys Arg Phe Cys Ile Ser Ile Asn Thr Thr Trp Cys Ala Gly
                20                  25                  30

Tyr Cys Tyr Thr Arg Asp Leu Val Tyr Lys Asp Pro Ala Arg Pro Lys
            35                  40                  45

Ile Gln Lys Thr Cys Thr Phe Lys Glu Leu Val Tyr Glu Thr Val Arg
    50                  55                  60

Val Pro Gly Cys Ala His His Ala Asp Ser Leu Tyr Thr Tyr Pro Val
65                  70                  75                  80

Ala Thr Gln Cys His Cys Gly Lys Cys Asp Ser Asp Ser Thr Asp Cys
                85                  90                  95

Thr Val Arg Gly Leu Gly Pro Ser Tyr Cys Ser Phe Gly Glu Met Lys
            100                 105                 110

Glu Ala Pro Asp Val Gln Asp Cys Pro Glu Cys Thr Leu Gln Glu Asn
        115                 120                 125

Pro Phe Phe Ser Gln Pro Gly Ala Pro Ile Leu Gln Cys Met Gly Cys 130                 135                 140
Cys Phe Ser Arg Ala Tyr Pro Thr Pro Leu Arg Ser Lys Lys Thr Met
145                 150                 155                 160

Leu Val Gln Lys Asn Val Thr Ser Glu Ser Thr Cys Val Ala Lys
                165                 170                 175

Ser Tyr Asn Arg Val Thr Val Met Gly Gly Phe Lys Val Glu Asn His
                180                 185                 190

Thr Ala Cys His Cys Ser Thr Cys Tyr Tyr His Lys Ser Ala Ser
                195                 200                 205

<210> SEQ ID NO 22
<211> LENGTH: 135
<212> TYPE: DNA
<213> ORGANISM: Artificial Sequence
<220> FEATURE:
<223> OTHER INFORMATION: Synthetic sequence

<400> SEQUENCE: 22
accacgacgc cagcgccgcg accaccaaca ccggcgccca ccatcgcgtc gcagcccctg      60
tccctgcgcc cagaggcgtg ccggccagcg gcgggggggcg cagtgcacac gaggggggctg    120 gacttcgcct gtgat                                                      135

<210> SEQ ID NO 23
<211> LENGTH: 45
<212> TYPE: PRT
<213> ORGANISM: Artificial Sequence
<220> FEATURE:
<223> OTHER INFORMATION: Synthetic sequence

<400> SEQUENCE: 23

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp
                35                  40                  45

<210> SEQ ID NO 24
<211> LENGTH: 81
<212> TYPE: DNA
<213> ORGANISM: Artificial Sequence
<220> FEATURE:
<223> OTHER INFORMATION: Synthetic sequence

<400> SEQUENCE: 24
ttttgggtgc tggtggtggt tggtggagtc ctggcttgct atagcttgct agtaacagtg      60
gcctttatta ttttctgggt g                                                81

<210> SEQ ID NO 25
<211> LENGTH: 27
<212> TYPE: PRT
<213> ORGANISM: Artificial Sequence
<220> FEATURE:
<223> OTHER INFORMATION: Synthetic sequence

<400> SEQUENCE: 25

Phe Trp Val Leu Val Val Val Gly Gly Val Leu Ala Cys Tyr Ser Leu
1               5                   10                  15

Leu Val Thr Val Ala Phe Ile Ile Phe Trp Val
                20                  25

<210> SEQ ID NO 26
<211> LENGTH: 207
<212> TYPE: DNA
<213> ORGANISM: Artificial Sequence
<220> FEATURE:
<223> OTHER INFORMATION: Synthetic sequence

<400> SEQUENCE: 26

```
accacgacgc cagcgccgcg accaccaaca ccggcgccca ccatcgcgtc gcagcccctg    60
tccctgcgcc cagaggcgtg ccggccagcg gcggggggcg cagtgcacac gagggggctg   120
gacttcgcct gtgatatcta catctgggcg cccttggccg ggacttgtgg ggtccttctc   180
ctgtcactgg ttatcaccct ttactgc                                      207
```

<210> SEQ ID NO 27
<211> LENGTH: 69
<212> TYPE: PRT
<213> ORGANISM: Artificial Sequence
<220> FEATURE:
<223> OTHER INFORMATION: Synthetic sequence

<400> SEQUENCE: 27

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Val
    50                  55                  60

Ile Thr Leu Tyr Cys
65

<210> SEQ ID NO 28
<211> LENGTH: 123
<212> TYPE: DNA
<213> ORGANISM: Artificial Sequence
<220> FEATURE:
<223> OTHER INFORMATION: Synthetic sequence

<400> SEQUENCE: 28

```
aggagtaaga ggagcaggct cctgcacagt gactacatga acatgactcc ccgccgcccc    60
gggcccaccc gcaagcatta ccagccctat gccccaccac gcgacttcgc agcctatcgc   120
tcc                                                                123
```

<210> SEQ ID NO 29
<211> LENGTH: 41
<212> TYPE: PRT
<213> ORGANISM: Artificial Sequence
<220> FEATURE:
<223> OTHER INFORMATION: Synthetic sequence

<400> SEQUENCE: 29

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

```
<210> SEQ ID NO 30
<211> LENGTH: 339
<212> TYPE: DNA
<213> ORGANISM: Artificial Sequence
<220> FEATURE:
<223> OTHER INFORMATION: Synthetic sequence

<400> SEQUENCE: 30
agagtgaagt tcagcaggag cgcagacgcc cccgcgtacc agcagggcca gaaccagctc      60
tataacgagc tcaatctagg acgaagagag gagtacgatg ttttggacaa gagacgtggc     120
cgggaccctg agatgggggg aaagccgaga aggaagaacc ctcaggaagg cctgtacaat     180
gaactgcaga aagataagat ggcggaggcc tacagtgaga ttgggatgaa aggcgagcgc     240
cggaggggca aggggcacga tggcctttac cagggtctca gtacagccac caaggacacc     300
tacgacgccc ttcacatgca ggccctgccc cctcgctaa                            339

<210> SEQ ID NO 31
<211> LENGTH: 112
<212> TYPE: PRT
<213> ORGANISM: Artificial Sequence
<220> FEATURE:
<223> OTHER INFORMATION: Synthetic sequence

<400> SEQUENCE: 31

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

METHODS AND COMPOSITIONS OF A FOLLICLE STIMULATING HORMONE RECEPTOR IMMUNORECEPTOR

CROSS REFERENCE TO RELATED APPLICATIONS

The present application is a 35 U.S.C. § 371 national phase application from, and claims priority to, International Application No. PCT/US2015/058797, filed Nov. 3, 2015, which claims priority under 35 U.S.C. § 119(e) to U.S. Provisional Application No. 62/074,893, filed Nov. 4, 2014, U.S. Provisional Application No. 62/074,930, filed Nov. 4, 2014, and, U.S. Provisional Application No. 62/144,159, filed Apr. 7, 2015, all of which applications are incorporated herein by reference in their entireties.

BACKGROUND OF THE INVENTION

Despite great advances in research and treatment, the occurrence and mortality of ovarian cancer remains high. Each year, about 22,000 women in the United States are diagnosed with ovarian cancer. Currently, the standard treatment for Stage IV ovarian cancer consists of both surgery and chemotherapy. Unfortunately, less than 10% of patients experience long-term survival following standard treatment (Barnett et al., Cancer 119:3653-3661, 2013; Phippen et al., Gynecol Oncol 131:158-162, 2013; Zhidkov et al., Mol Pharm. 10(9): 3315-22, 2013) because advanced stage ovarian cancer is difficult to completely remove with surgery and currently available chemotherapy is unable to eradicate all of the remaining cancer cells (Colombo, Future Oncol 9:19-23; colombo et al., Crit Rev Oncol Hematol. 89(2): 207-16, 2014; Rooth, Br J Nurs. 22(17):523-30, 2013).

Follicle-stimulation hormone (FSH, follitropin) is released by the pituitary gland and is associated with reproduction and the development of eggs in women and sperm in men. This hormone belongs to a family of heterodimeric glycoproteins together with luteinizing hormone (LH; lutropin), chorionic gonadotropin (CG; choriogonadotropin), and thyroid-stimulating hormone (TSH; thyrotropin). The FSH heterodimer protein comprises an alpha and a beta subunit. The alpha subunit is encoded by a single gene and can be interchanged between hormones without effect on receptor binding, whereas the beta subunits differ and direct binding specificity. Follicle-stimulation hormone receptor (FSHR) is a seven-transmembrane G-protein-coupled receptor, which interacts with follicle-stimulation hormone (FSH).

In healthy adult humans, FSHR is expressed only in the granulosa cells of the ovary, Sertoli cells of the testis, and a minimal expression is observed in the endothelial cells of gonadal blood vessels. Recently several reports have documented the expression of FSHR in 50-70% of ovarian cancer tissues, as well as other types of tumors including; renal cell carcinoma, prostate, breast, colon, pancreas, urinary bladder, kidney, lung, liver, stomach, testis. Notably, FSHR protein is also selectively expressed on the surface of the blood vessels of a wide range of tumors e.g., renal cell carcinoma, prostate, breast, colon, pancreas, urinary bladder, kidney, lung, liver, stomach, testis, and ovary (primary tumor and/or metastases) (Radu et al., N Engl J Med 363:1621, 2010; Siraj et al., BMC Cancer 13:246, 2013; and Renner et al., Histopathology 63:29, 2013). FSH receptors are important in tumor angiogenesis by signaling via two pathways, one involving VEGF, and a Gq/11 mechanism that activates VEGFR-2 independently of VEGF. The relative specific expressions of FSHR on cell surface of malignant tissues make it an attractive target for FSHR tumor immunotherapy.

Immunotherapy is a promising approach for cancer treatment thanks to the potential of the immune system to target tumors without the toxicity associated with traditional chemo-radiation. However, there is an urgent need for a more targeted antigen-specific immunotherapy for treatment of certain cancers, such as, for example, ovarian cancer. The present invention addresses this need.

SUMMARY OF THE INVENTION

As disclosed herein, the present invention includes compositions of and methods for their use, of novel peptides that specifically bind to follicle-stimulation hormone receptor (FSHR).

In one aspect, the invention includes an isolated nucleic acid sequence encoding a follicle-stimulating hormone receptor (FSHR) binding immunoreceptor (IR) comprising a FSHR binding domain, a transmembrane domain, and a signaling domain, wherein the FSHR binding domain comprises a follicle-stimulating hormone (FSH) or fragment thereof, a FSHR antagonist or fragment thereof, or an anti-FSHR agonist or fragment thereof.

In another aspect, the invention includes a vector comprising the isolated nucleic acid sequence described herein.

In yet another aspect, the invention includes an isolated follicle-stimulating hormone receptor (FSHR) binding immunoreceptor (IR) comprising a FSHR binding domain, a transmembrane domain, and a signaling domain, wherein the FSHR binding domain comprises a follicle-stimulating hormone (FSH) or fragment thereof, a FSHR antagonist or fragment thereof, or an anti-FSHR agonist or fragment thereof.

In still another aspect, the invention includes a cell comprising the isolated nucleic acid sequence described herein or the isolated FSHR binding IR described herein. In another aspect, the invention includes a modified cell comprising a nucleic acid sequence encoding a follicle-stimulating hormone receptor (FSHR) binding immunoreceptor (IR), wherein the FSHR binding IR comprises a FSHR binding domain, a transmembrane domain, and a signaling domain, and wherein the FSHR binding domain comprises a follicle-stimulating hormone (FSH) or fragment thereof, a FSHR antagonist or fragment thereof, or an anti-FSHR agonist or fragment thereof.

In yet another aspect, the invention includes a composition comprising the modified cell described herein. In still another aspect, the invention includes a use of the cell described herein in the manufacture of a medicament for the treatment of cancer in a subject in need thereof.

In another aspect, the invention includes a method for stimulating a T cell-mediated immune response to a thyroid cell population in a mammal. The method comprises administering to a subject an effective amount of a modified cell that expresses a follicle stimulating hormone receptor (FSHR) immunoreceptor (IR), wherein the FSHR binding IR comprises a FSHR binding domain, a transmembrane domain, and a signaling domain, and wherein the FSHR binding domain comprises a follicle-stimulating hormone (FSH) or fragment thereof, a FSHR antagonist or fragment thereof, or an anti-FSHR agonist or fragments thereof.

In yet another aspect, the invention includes a method of treating a condition in a subject. The method comprises administering to the subject a modified T cell that expresses a follicle stimulating hormone receptor (FSHR) binding immunoreceptor (IR), wherein the FSHR binding IR comprises a FSHR binding domain, a transmembrane domain, and a signaling domain, and wherein the FSHR binding domain comprises a follicle-stimulating hormone (FSH) or fragment thereof, a FSHR antagonist or fragment thereof, or an anti-FSHR agonist or fragments thereof.

In various embodiments of the above aspects or any other aspect of the invention delineated herein, the FSHR binding domain is encoded by a nucleic acid sequence selected from the group consisting of SEQ ID NOs: 6, 8, 10, 12, 14, 16, 18 and 20. In another embodiment, the FSHR binding domain comprises an amino acid sequence selected from the group consisting of SEQ ID NOs: 1-5, 7, 9, 11, 13, 15, 17, 19 and 21.

In one embodiment, the transmembrane domain comprises a CD8alpha hinge and transmembrane domain. In another embodiment, wherein the signaling domain comprises a CD3 signaling domain.

In another embodiment, the FSHR binding IR further comprises a costimulatory signaling region, such a costimulatory signaling region comprising an intracellular domain of a costimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, a ligand that specifically binds with CD83, and any combination thereof.

In another embodiment, the FSHR binding IR specifically binds to FSHR expressed by tumor cells and/or tumor vasculature. In one embodiment, the tumor cells are from a cancer selected from the group consisting of ovarian cancer, renal cell carcinoma, bladder cancer, kidney cancer, testicular cancer, prostate cancer, breast cancer, colon cancer, pancreatic cancer, lung cancer, liver cancer, stomach cancer and any combination thereof.

In another embodiment, the cell that is modified is selected from the group consisting of a T cell, a natural killer (NK) cell, a cytotoxic T lymphocyte (CTL), and a regulatory T cell. In another embodiment, the modified T cell is autologous to the subject.

In another embodiment, the condition that is treated is a cancer selected from the group consisting of ovarian cancer, renal cell carcinoma, bladder cancer, kidney cancer, testicular cancer, prostate cancer, breast cancer, colon cancer, pancreatic cancer, lung cancer, liver cancer, stomach cancer and any combination thereof.

In another embodiment, the method of treating a condition further comprises administering an antitumor vaccine to the subject. In one embodiment, the modified T cell and the antitumor vaccine are co-administered to the subject.

In one aspect, the invention includes an isolated nucleic acid sequence encoding a chimeric antigen receptor comprising a follicle-stimulating hormone receptor (FSHR) binding domain, a transmembrane domain, a costimulatory signaling region, and a CD3 zeta signaling domain, wherein the FSHR binding domain comprises an anti-FSHR antibody or a fragment thereof.

In another aspect, the invention includes a vector comprising the isolated nucleic acid sequence described herein.

In yet another aspect, the invention includes an isolated chimeric antigen receptor (CAR) comprising a follicle-stimulating hormone receptor (FSHR) binding domain, a transmembrane domain, a costimulatory signaling region, and a CD3 zeta signaling domain, wherein the FSHR binding domain comprises anti-FSHR antibody or a fragment thereof.

In still another aspect, the invention includes a cell comprising the isolated nucleic acid sequence described herein or the isolated CAR described herein.

In another aspect, the invention includes a modified cell comprising a nucleic acid sequence encoding a chimeric antigen receptor (CAR) comprising a follicle-stimulating hormone receptor (FSHR) binding domain, a transmembrane domain, a costimulatory signaling region, and a CD3 zeta signaling domain, wherein the FSHR binding domain comprises an anti-FSHR antibody or a fragment thereof.

In yet another aspect, the invention includes a composition comprising the modified cell described herein. In still another aspect, the invention includes a use of the cell described herein in the manufacture of a medicament for the treatment of cancer in a subject in need thereof.

In another aspect, the invention includes a method for stimulating a T cell-mediated immune response to a thyroid cell population in a mammal. The method comprises administering to a subject an effective amount of a modified cell that expresses a chimeric antigen receptor comprising a follicle-stimulating hormone receptor (FSHR) binding domain, a transmembrane domain, a costimulatory signaling region, and a CD3 zeta signaling domain, wherein the FSHR binding domain comprises an anti-FSHR antibody or a fragment thereof.

In another aspect, the invention includes a method of treating a subject with cancer. The method comprises administering to the subject a modified T cell that expresses a chimeric antigen receptor comprising a follicle-stimulating hormone receptor (FSHR) binding domain, a transmembrane domain, a costimulatory signaling region, and a CD3 zeta signaling domain, wherein the FSHR binding domain comprises an anti-FSHR antibody or a fragment thereof. In various embodiments of the above aspects or any other aspect of the invention delineated herein, the FSHR binding domain comprises a heavy and light chain. In one embodiment, the FSHR binding domain is a human antibody, a humanized antibody, and a fragment thereof, such as an antibody or a fragment thereof is selected from the group consisting of a Fab fragment, a F(ab')$_2$ fragment, a Fv fragment, and a single chain Fv (scFv). In another embodiment, the FSHR binding domain specifically binds to FSHR expressed by tumor cells and/or tumor vasculature, such as tumor cells from a cancer selected from the group consisting of ovarian cancer, renal cell carcinoma, bladder cancer, kidney cancer, testicular cancer, prostate cancer, breast cancer, colon cancer, pancreatic cancer, lung cancer, liver cancer, stomach cancer and any combination thereof.

In another embodiment, the costimulatory signaling region comprises an intracellular domain of a costimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, a ligand that specifically binds with CD83, and any combination thereof.

In another embodiment, the cell that is modified is selected from the group consisting of a T cell, a natural killer (NK) cell, a cytotoxic T lymphocyte (CTL), and a regulatory T cell. In yet another embodiment, the modified T cell is autologous to the subject.

In another embodiment, the cancer treated is selected from the group consisting of ovarian cancer, renal cell carcinoma, bladder cancer, kidney cancer, testicular cancer, prostate cancer, breast cancer, colon cancer, pancreatic cancer, lung cancer, liver cancer, stomach cancer and any combination thereof.

In another embodiment, the method of treating cancer further comprises administering an antitumor vaccine to the subject. In one embodiment, the modified T cell and the antitumor vaccine are co-administered to the subject.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIGS. 1A-1I are a series of images demonstrating the generation of primary human T cells expressing anti-FSHR immunoreceptor. FIGS. 1A-I are schematic representations of constructs containing FSH beta sequences 33-53, 51-65, and 81-95, or a composite of FHS alpha and beta derived peptide encoding sequences for alpha beta, agonist A, agonist B, antagonist A and antagonist B.

FIGS. 3A-3B show the lack of immunoreactivity of anti-FSHR redirected T cells against immobilized recombinant hFSHR. FIG. 3A shows that GFP+ Anti-FSHR IR T cells do not bind either immobilized recombinant FSHR or folate receptor alpha protein. FIG. 3B shows that anti-FSHR IR T cells (A, 33-53; B, 51-65) do not produce high levels of IFN-g cytokine when exposed to immobilized recombinant FSHR protein, but do when exposed to immobilized anti-CD3 antibody, OKT-3.

FIG. 5 is a histogram depicting the immunoreactivity of anti-FSHR immune receptors against FSHR+ cancer cells CAOV434 and MCF7, but not MB361 or mouse mesothelioma line, AE17. Anti-FSHR(33-53)-28z CD8+ T cells, but not untransduced CD8+ T cells, recognize FSHR on tumor cells and produce IFN-gamma in vitro. Anti-FSHR(51-65)-28z T cells produce lower levels of IFN-g in response to FSHR+ cancer cell lines.

FIG. 6A: Anti FSHR 33-53b-28z and anti-FSHR Agonist A-28z T cells become activated and express the activation marker CD69 when they encounter FSHR-positive human OvCa cell line CaOV3, and mouse ID8 (FSHR positive) targets. FIG. 6B: Anti-FSHR 33-53b-28z and anti-FSHR Agonist A-28z T cell killing of human OvCa cell line CaOV3, and mouse ID8 (FSHR positive) targets, was assessed in luciferase based killing assay (16 hrs). Target cells were transduced to express firefly luciferase and co-cultured with T cells at E:T ratios of):1, 1:1, or 3:1. Residual luciferase signal was determined after 18 hrs. Percent lysis was determined by luminescence comparison to untreated target wells. Results are presented as mean±SD. Values of *P<0.05 were considered statistically significant. FIG. 6C demonstrates that anti-FSHR(33-53)-28z T cells have the functional ability to specifically recognize and kill tumor cells expressing the target antigen, FSHR (upper left). Primary human T-cells transduced to express anti-FSHR(33-53)-IR-28z were co-cultured with tumor cells (MCF7/FSHR+, CAOV434/FSHR+ and AE17 FSHR negative) for 20 hrs at the indicated effector to target ratio. Percent specific target cell lysis was calculated as (experimental−spontaneous release)±(maximal−spontaneous release)×100. Data represent the means±SD for 3 different experiments. Thus, anti-FSHR T cells discriminate between the target antigen and other antigens. Upper right graph shows that control anti-folate receptor chimeric antigen receptor (CAR) T cells recognize and lyse folate receptor positive cancer cell lines. Lower graph shows that control T cells engineered to express green fluorescence protein (GFP), but not an immunoreceptor, do not lyse cancer cell lines.

FIG. 7 is a graph showing immune-reactivity of anti-FSHR T cells compared to a folate receptor alpha specific CAR T cells. Anti-FSHRb(33-53) FSH-28z T cells specifically recognized and produced IFNgamma against FSHR positive cell line, albeit less than that secreted by anti-folate receptor CAR T cells against the same target cells demonstrating that FSHR IR T cells recognize and respond against FSHR+ tumor cells (MCF7, CaoV3, OVCAR3) but not antigen negative cells (MDA MB 361, AE17). IFN-gamma cytokine was measured from overnight cell culture supernatants by ELISA. (Mean pg/ml+/−SEM from triplicate wells is shown). The control anti-Folate Receptor CAR (MOV19-28z) is shown as a positive control for redirected antigen-specific T cell function; untransduced T cells served as a negative control.

FIG. 8C depicts cytokine secretion by anti FSHR redirected T-cells and control GFP transduced primary human T-cells in response to the indicated cancer cell target (FSHR+ CaOV3, FSHR+ID8, FSHR negative 293T, or FSHR negative AE17). IFNg, IL2, MIP1a, TNFa, IL4 and IL10 secretion was detected by CBA (Cytokine bead-based immunoassay) 16 hr after following tumor stimulation (Data represents 3 independent experiments in triplicates). Results are presented as mean±SD. Values of *P<0.01, **P<0.05 were considered statistically significant. FIG. 8D shows that anti-FHSR T cells upregulated surface expression of a T cell activation marker when exposed to FSHR+ cancer cells. GFP+ anti-FSHRb33-53FSH-28z T cells up-regulated levels of surface CD69 expression following 6 hr coculture with FSHR positive, CaOV3 cancer cell line. GFP negative T cells that lack the anti-FSHRb33-53FSH-28z immune receptor do not upregulate CD69 in response to stimulation with FSHR positive cancer cells. Two representative histograms are shown.

FIG. 10 is a table listing the anti-FSHR peptides of this invention (SEQ ID NOs: 1-5).

FIG. 12A shows that the immunoreactivity of T cells expressing the various anti-FSHR immune receptors against FSHR+ human (CaOV3) ovarian cancer cells as well as mouse ID8-OVA ovarian cancer cell line which endogenously expresses surface mouse FSHR. All constructs contain −28z intracellular domains in this experiment. FIG. 12B shows the antigen-specific IFNg secretion by a panel of anti-FSHR-IR T-cells as detected in supernatants by ELISA after overnight co-culture with FSHR-positive CaOV3 or FSHR-negative 293T target cells. Co-cultures were established at 1:1 E:T ratio. FIG. 12C: IFNg secretion by FSHR redirected T-cells following overnight co-culture with mouse FSHR positive OvCa cells (ID8) and negative mouse mesothelioma cell line (AE17). Results are reported as pg/ml concentration and presented as mean±SD. Expression of mouse FSHR in OvCa cell lines and control AE17 cells was determined by RT-PCR using FSHR-specific PCR primers. Controls included AE17 cells and no input ($H_2O$). 18S was used as a control. RT-PCR using FSHR primers based on mouse sequence amplified the predicted product from cDNA templates. The mouse-FSHR was PCR-amplified using the following primers: 5'-GGGATCTGGATGTCAT-CACT-3" (SEQ ID NO: 34) and 5'-GGAGAACACATCT-GCCTCTA-3' (GeneID: 14309, SEQ ID NO: 35). FIG. 12D: Lack of strong immunorecognition of human recombinant FSHR protein by anti-FSHR T-cells. IFNg—interferon gamma, E:T—Effector: Target. *, P<0.05;, P<0.01; *, P<0.001 (Student t test).

FIGS. 13A-13: FSHR cell surface expression was detected by flow cytometry on a panel of established ovarian and breast cancer cell lines utilizing anti FSHR rabbit antibody followed by anti-rabbit APC (open histograms), or isotype control (grey) stained cells. AE17 mouse mesothelioma cell line was used as a negative control. Specific MFI is represented on each plot. Mean fluorescence intensity (MFI). FIG. 13C: Expression of human FSHR in OvCa cell lines and control 293T cells determined by RT-PCR using FSHR-specific PCR primers. Controls included 293T cells and no input (H2O). 18S was used as a control. RT-PCR using FSHR primers based on human sequence amplified the predicted 234 bp product from cDNA templates. The human-FSHR was PCR-amplified using the following primers: 5'-CTCACCAAGCTTC-GAGTCATCCAA-3' (SEQ ID NO: 32) and 5'-GCT-CATCTAGTTGGGTTCCATT-3' (GeneID: 2492, SEQ ID NO: 33).

FIG. 18A: $5\times10^6$ T-cells CaOV3-Luciferase cells were injected into NSG mice s.c. on day zero (d0). $5\times10^6$ T-cells Immune Receptor+ T-cells were given IV on day 20 and day 25 (d20 and d25). Tumor growth was monitored by caliper measurement. Graphs represent mean±SEM of n=5 mice per experiment. P values were calculated compared to GFP-T-cells and PBS treated control mice. (* P<0.05, ** P<0.01, ns P>0.05). Groups; PBS vs anti FSHR AgonistA-28z P-Value is 0.001755. For the PBS vs anti FSHR 33-53b-28z groups, the p-Value is 0.008346. For Anti FSHR 33-53b-28z vs anti FSHR AgonistA-28z groups, the P-Value is 0.234729. For PBS vs GFP T-cell groups, the P-Value is 0.45995. For GFP T-cells vs anti FSHR 33-53b-28z groups, the P-Value is 0.020878. For GFP T-cells vs anti FSHR AgonistA-28z groups, the P-Value is 0.004716. The result is significant at p<0.05. FIG. 18B: Preferential expansion and survival of peripheral human T-cells in anti-FSHR T-cell treated mice compared to controls; GFP T-cells and PBS treated group. Peripheral blood was collected 20 and 35 days post T-cell injection and absolute number of human CD3+ T-cells was quantified by flow cytometry via TruCount bead-based counting and reported in total cells/uL blood. Bar graphs represent mean+SD for n=5 mice per group. P values were determined compared to control GFP T-cell treated group. (* indicates P<0.05, ns indicates P>0.05).

DETAILED DESCRIPTION

Definitions

Figure 1A:
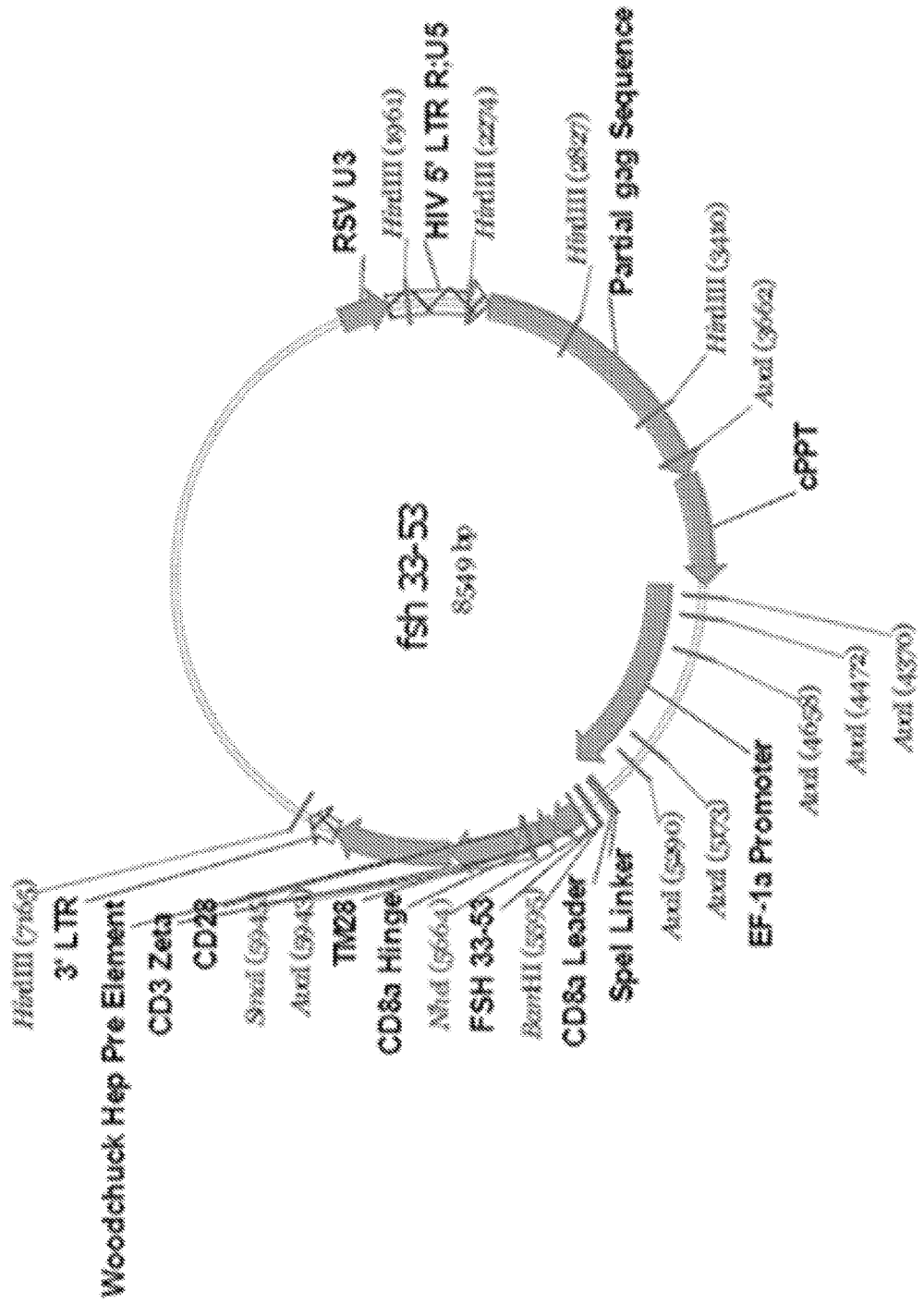
Figure 1B:
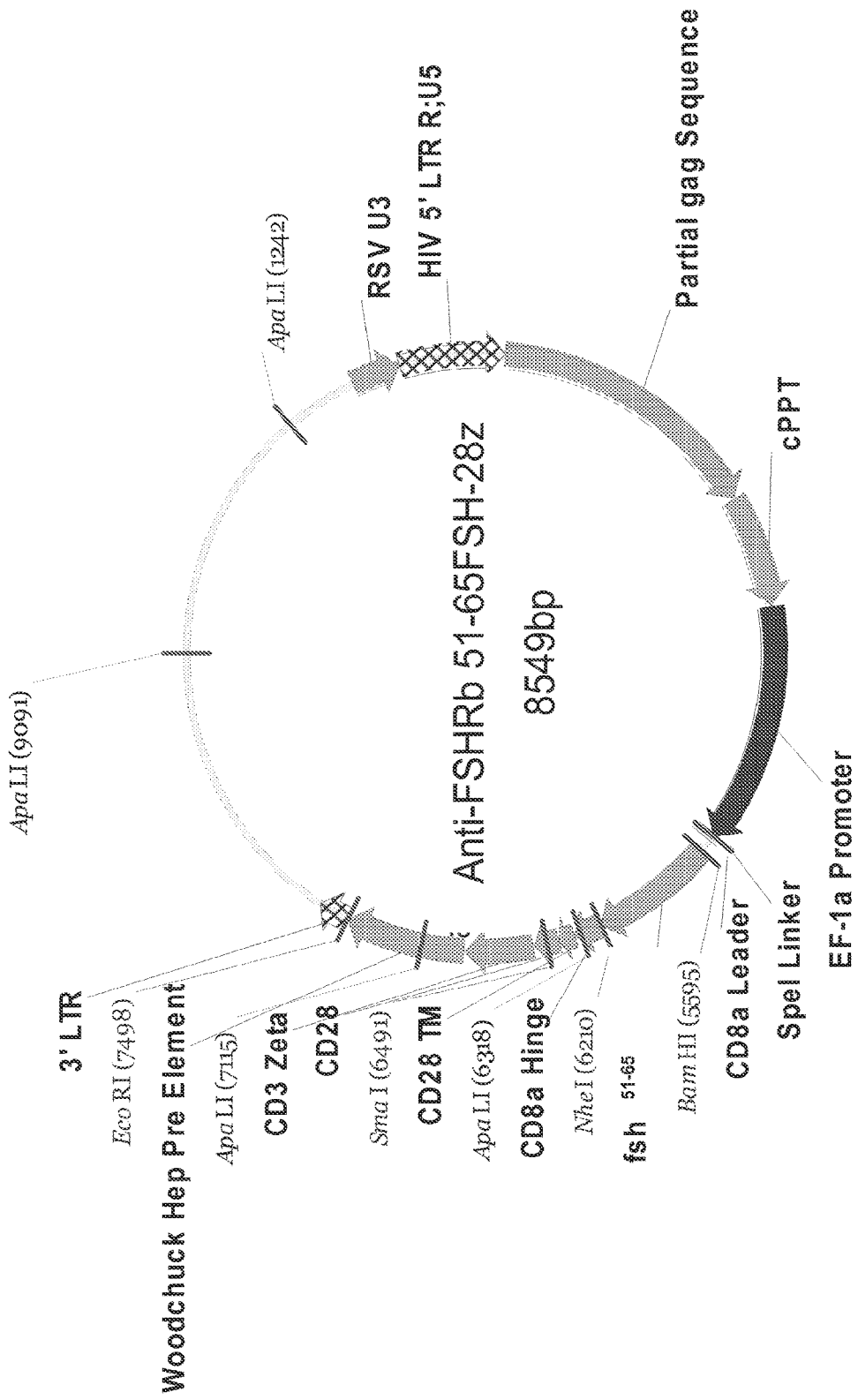
Figure 1C:
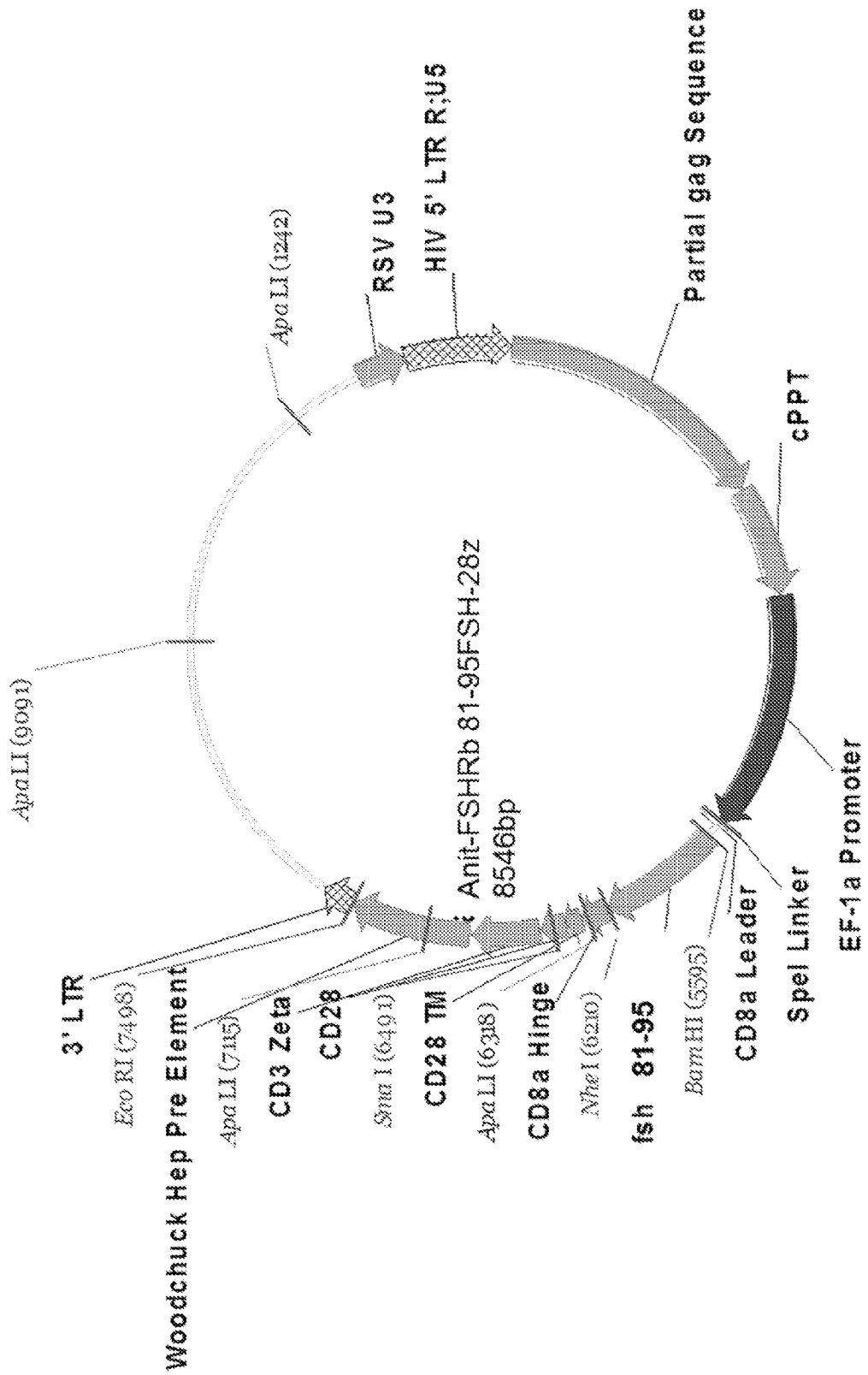
Figure 1D:
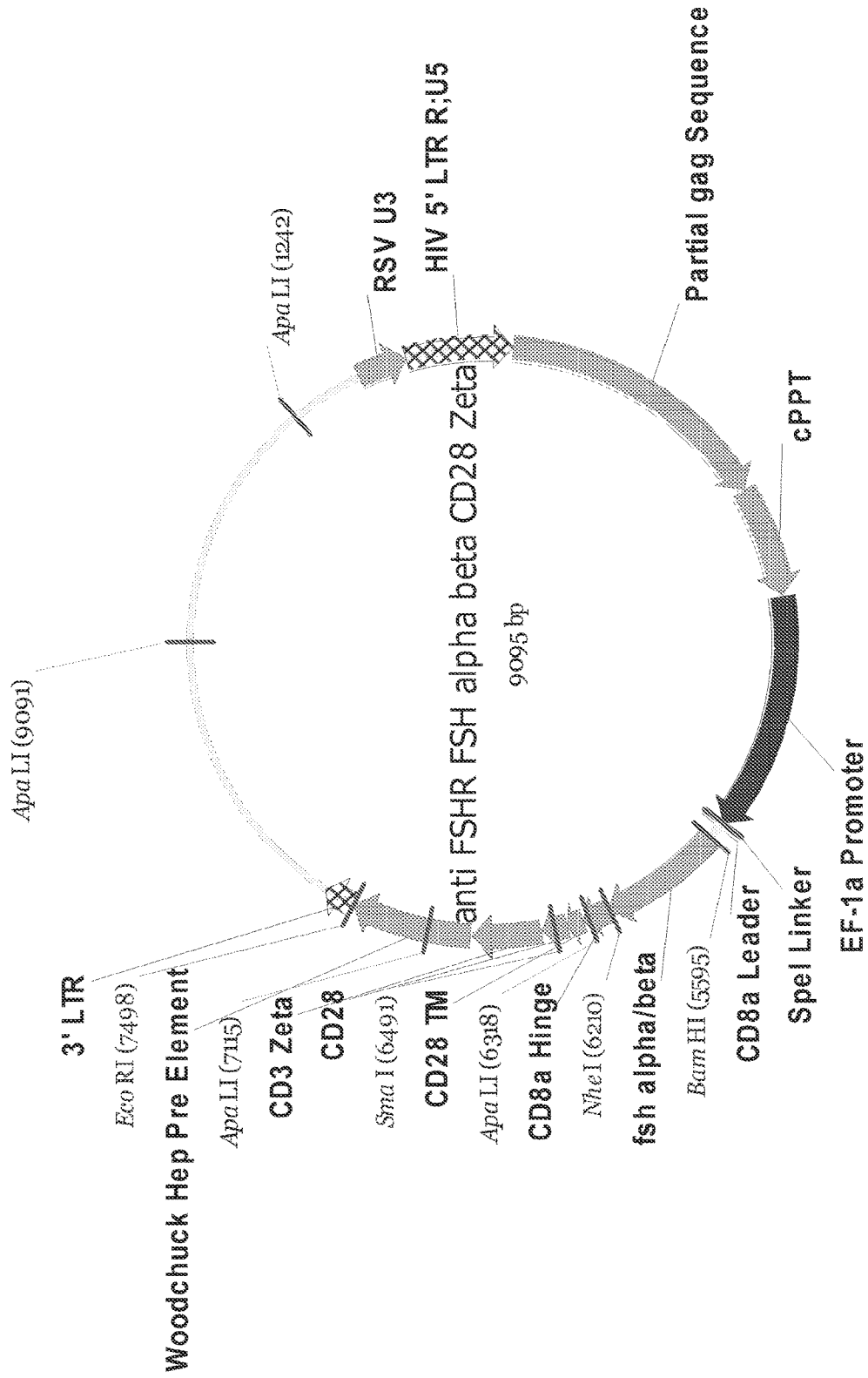
Figure 1E:
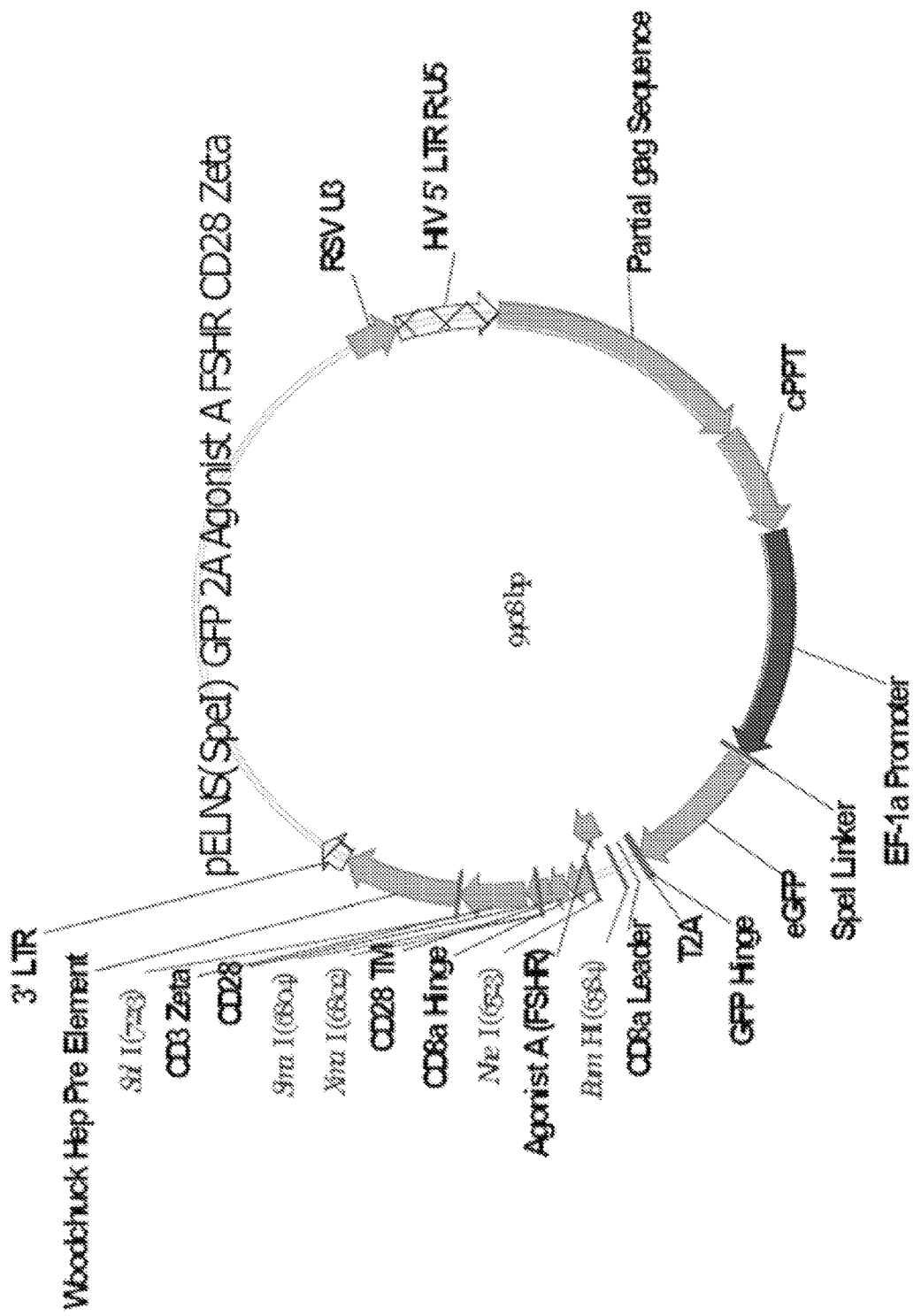
Figure 1F:
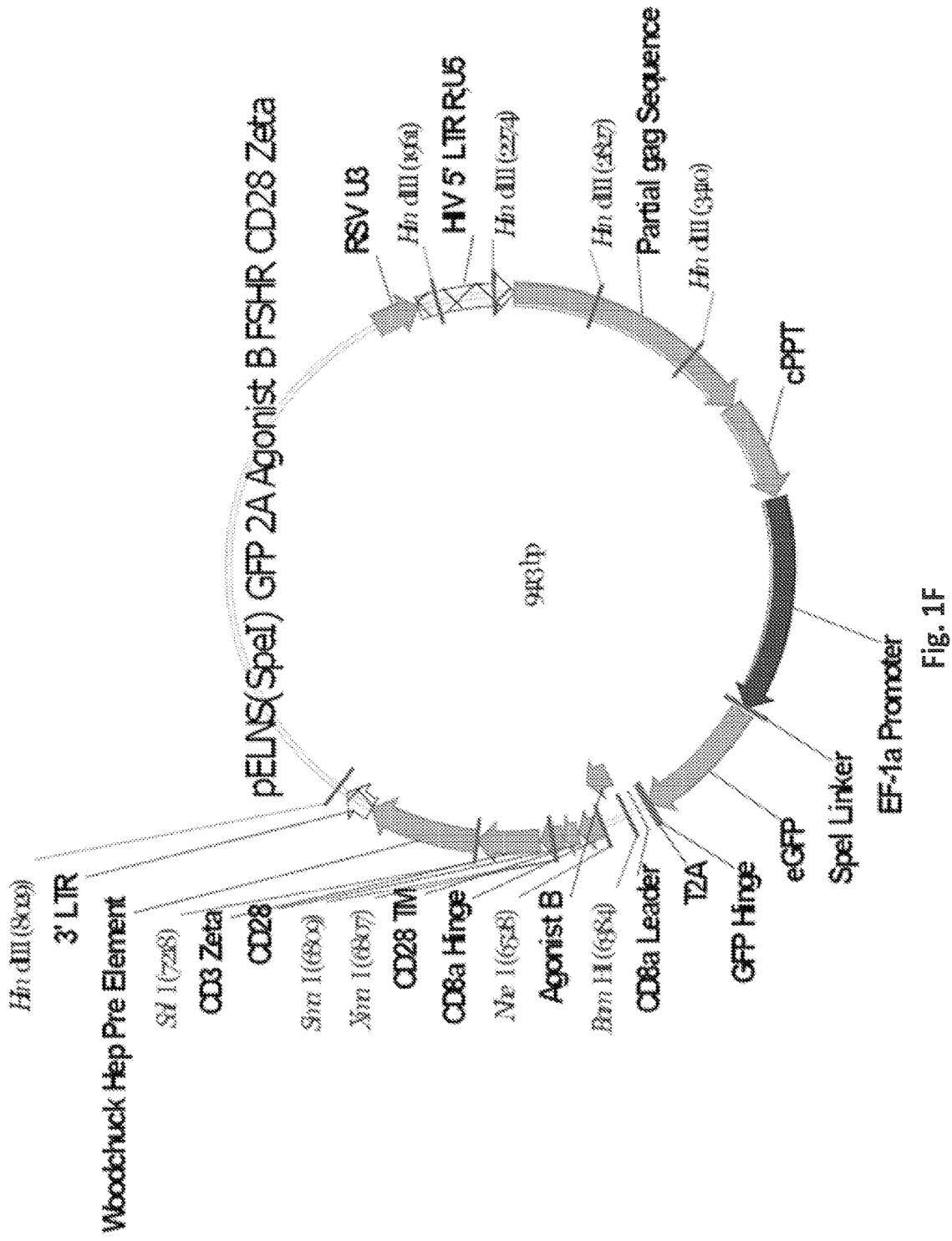
Figure 1G:
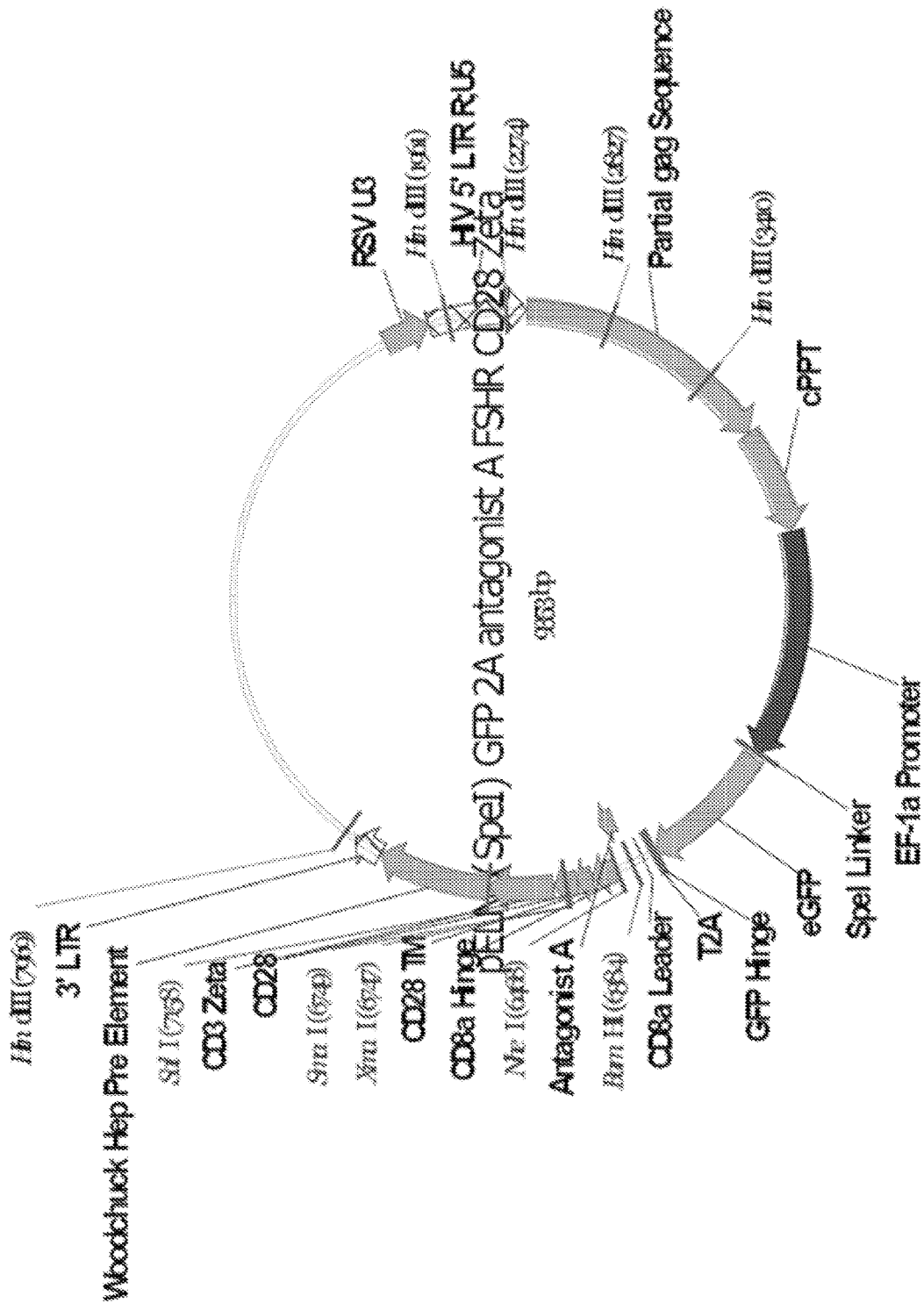
Figure 1H:
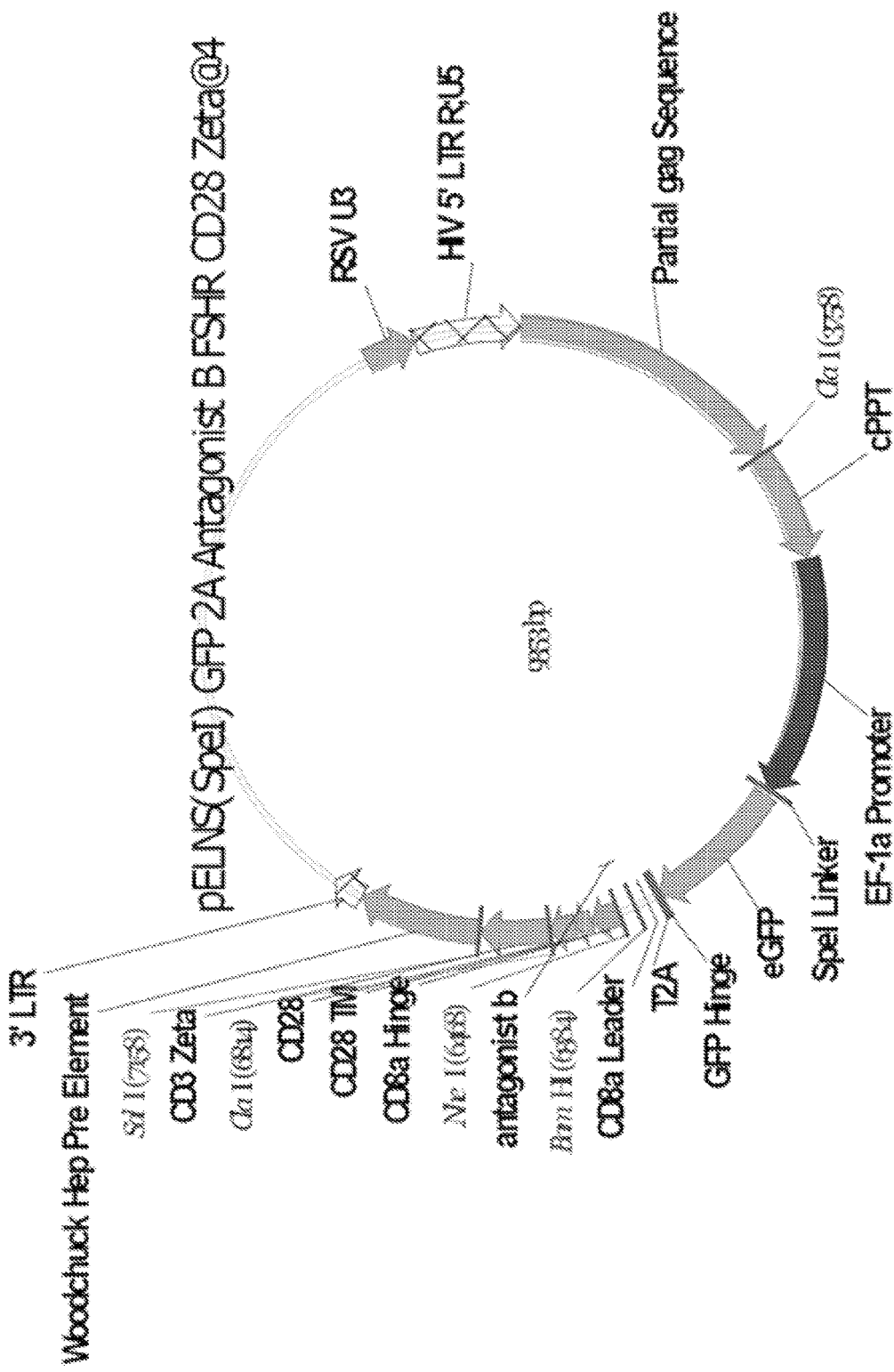
Figure 11:
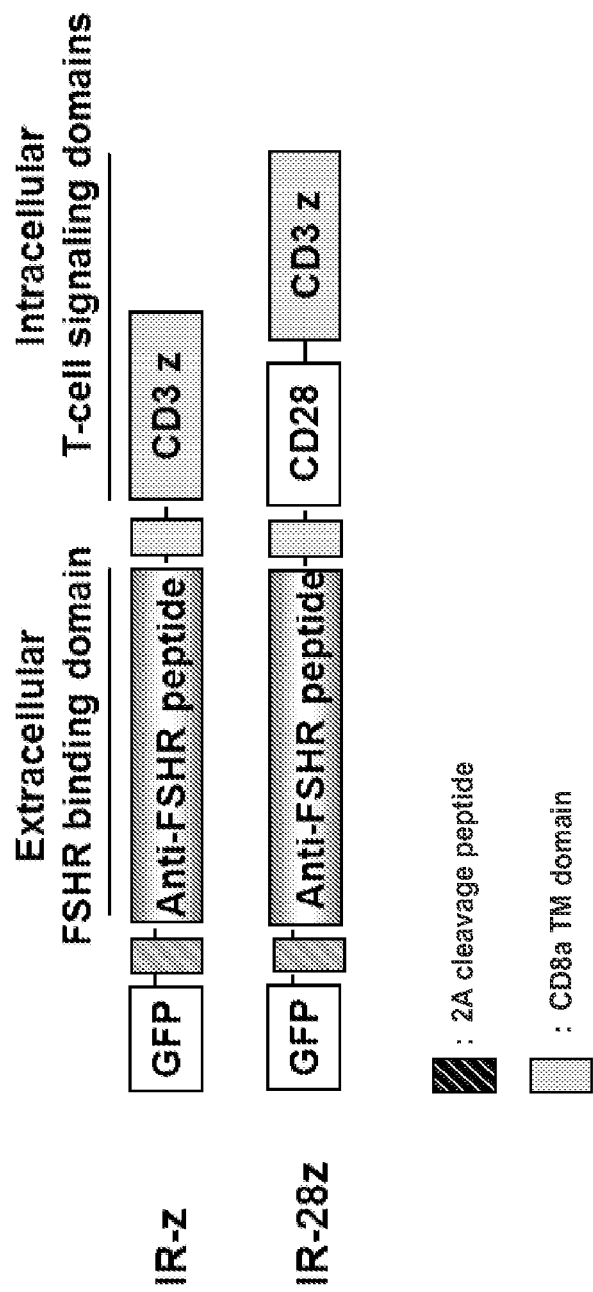
FIGS. 11A-11B illustrate the cell surface expression of the various anti-FSHR immune receptors by primary human T cells following lentiviral transduction. Transduction efficiency was determined based upon GFP expression. pELNS-GFP-2A-antiFSHR-IR constructs were used for lentivirus production. Histograms show percentage of anti-FSHR IR T cells relative to untransduced T cells following transduction with lentivirus. GFP—green fluorescent protein, TM-transmembrane domain. UNT—represents untransduced T cells.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting. The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies (scFv) and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. κ and λ light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "anti-FSHR agonist" as used herein refers to a molecule, fragment of a molecule, peptides, or a polypeptide sequence that binds to a follicle stimulating hormone receptor with similar binding affinity and/or activity as an anti-FSHR antibody.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

As used herein, the term "autologous" is meant to refer to any material derived from the same individual to which it is later to be re-introduced into the individual.

"Allogeneic" refers to a graft derived from a different animal of the same species.

"Xenogeneic" refers to a graft derived from an animal of a different species.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, ovarian cancer, renal cell carcinoma, bladder cancer, kidney cancer, testicular cancer, prostate cancer, breast cancer, colon cancer, pancreatic cancer, lung cancer, liver cancer, stomach, thyroid cancer, and the like.

The term "chimeric antigen receptor" or "CAR," as used herein, refers to an artificial T cell receptor that is engineered to be expressed on an immune effector cell and specifically bind an antigen. CARs may be used as a therapy with adoptive cell transfer. T cells are removed from a patient and modified so that they express the receptors specific to a particular form of antigen. In some embodiments, the CARs have been expressed with specificity to a tumor associated antigen, for example. CARs may also comprise an intracellular activation domain, a transmembrane domain and an extracellular domain comprising a tumor associated antigen binding region. In some aspects, CARs comprise fusions of single-chain variable fragments (scFv) derived monoclonal antibodies, fused to CD3-zeta transmembrane; and intracellular domain. The specificity of CAR designs may be derived from ligands of receptors (e.g., peptides). In some embodiments, a CAR can target cancers by redirecting the specificity of a T cell expressing the CAR specific for tumor associated antigens.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for the ability to bind FSHR using the functional assays described herein.

"Co-stimulatory ligand," as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA and a Toll ligand receptor.

The term "dysregulated" when used in the context of the level of expression or activity of FSHR refers to the level of expression or activity that is different from the expression level or activity of FSHR in an otherwise identical healthy animal, organism, tissue, cell or component thereof. The term "dysregulated" also refers to the altered regulation of the level of expression and activity of FSHR compared to the regulation in an otherwise identical healthy animal, organism, tissue, cell or component thereof "Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Effective amount" or "therapeutically effective amount" are used interchangeably herein, and refer to an amount of a compound, formulation, material, or composition, as described herein effective to achieve a particular biological result. Such results may include, but are not limited to, the inhibition of virus infection as determined by any means suitable in the art.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

As used herein, the phrase "FSHR binding domain" refers to a protein domain or polypeptide that specifically binds to a follicle stimulating hormone receptor. In one embodiment, the FSHR binding domain may comprise a follicle-stimulating hormone (FSH) or fragment thereof, a FSHR antagonist or fragment thereof, or an anti-FSHR agonist or fragments thereof.

As used herein, "FSHR antagonist" refers to a molecule or fragment thereof that has affinity for a follicle stimulating hormone receptor. The FSHR antagonist has affinity to the active site on FSHR, a similar or the same binding site as follicle-stimulating hormone. FSHR antagonist binding affinity to the FSHR may be reversible or irreversible.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Humanized" forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies can comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

"Fully human" refers to an immunoglobulin, such as an antibody, where the whole molecule is of human origin or consists of an amino acid sequence identical to a human form of the antibody.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an Arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

The phrases "an immunologically effective amount", "an anti-immune response effective amount", "an immune response-inhibiting effective amount", or "therapeutic amount" refer to the amount of the composition of the present invention to be administered to a subject which amount is determined by a physician, optionally in consultation with a scientist, in consideration of individual differences in age, weight, immune response, type of disease/condition, and the health of the subject (patient) so that the desired result is obtained in the subject.

As used herein, "immunoreceptor" refers to chimeric receptor comprising a FSHR binding domain, a transmembrane domain, and an intracellular signaling domain. In one embodiment, the FSHR binding domain comprises a follicle-stimulating hormone (FSH) or fragments thereof, a FSH antagonist or fragments thereof, or a FSHR agonist or fragments thereof.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

As used herein, the terms "GDNF family receptor alpha 4," "follicle stimulating hormone receptor," and "FSHR" are used interchangeably, and include variants, isoforms and species homologs of human FSHR. Accordingly, human antibodies of this disclosure may, in certain cases, cross-react with FSHR from species other than human. In certain embodiments, the antibodies may be completely specific for one or more human FSHR proteins and may not exhibit species or other types of non-human cross-reactivity. The complete amino acid sequence of an exemplary human FSHR has Genbank/NCBI accession number: NM_022139.

By the term "modified" as used herein, is meant a changed state or structure of a molecule or cell of the invention. Molecules may be modified in many ways, including chemically, structurally, and functionally. Cells may be modified through the introduction of nucleic acids.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

A "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the plasma membrane of a cell. An example of a "cell surface receptor" is human FSHR.

"Single chain antibodies" refer to antibodies formed by recombinant DNA techniques in which immunoglobulin heavy and light chain fragments are linked to the Fv region via an engineered span of amino acids. Various methods of generating single chain antibodies are known, including those described in U.S. Pat. No. 4,694,778; Bird (1988) Science 242:423-442; Huston et al. (1988) Proc. Natl. Acad. Sci. USA 85:5879-5883; Ward et al. (1989) Nature 334: 54454; Skerra et al. (1988) Science 242:1038-1041.

By the term "specifically binds," as used herein, is meant an antibody, or a ligand, which recognizes and binds with a cognate binding partner (e.g., a stimulatory and/or costimulatory molecule present on a T cell) protein present in a sample, but which antibody or ligand does not substantially recognize or bind other molecules in the sample.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-$\beta$, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an WIC Class I molecule loaded with a peptide, an anti-CD3 antibody, a superagonist anti-CD28 antibody, and a superagonist anti-CD2 antibody.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

A "target cell" or "target site" refers to a cell or site to which a binding molecule may specifically bind under conditions sufficient for binding to occur. Binding may occur through a molecule or fragment thereof, such as an antigen, on the target cell or at a target site to a binding partner, such as an antibody.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, lentiviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention relates generally to the treatment of a patient having a cancer associated with dysregulated expression of FSHR, or at risk of having a cancer associated with dysregulated expression of FSHR, using cellular infusion. In one embodiment, cells are modified with receptors that bind to follicle stimulating hormone receptor. The receptors include FSH immuno-receptors (IR) and chimeric antigen receptors (CAR).

FSHR Immunoreceptors

The present invention includes immunoreceptors, particularly immunoreceptors that bind specifically to follicle stimulating hormone receptor (FSHR). In certain embodiments, the immunoreceptors of the invention comprise particular structural features such as comprising particular amino acid sequences or peptides. The invention also includes methods of making such immunoreceptors. The immunoreceptors of the invention can be incorporated into an immunotherapy, a pharmaceutical composition, and the like. Accordingly, the present invention provides compositions and methods for treating, among other diseases, cancer or any malignancy or autoimmune disease in which expression of FSHR is dysregulated.

In one aspect, the invention includes an isolated nucleic acid sequence encoding a follicle-stimulating hormone receptor (FSHR) binding immunoreceptor (IR) comprising a FSHR binding domain, a transmembrane domain, and a signaling domain, wherein the FSHR binding domain comprises a follicle-stimulating hormone (FSH) or fragment thereof, a FSHR antagonist or fragment thereof, or an anti-FSHR agonist or fragments thereof. In one embodiment, the FSHR immuno-receptors can be used for diagnosing the presence of FSHR in a biological sample. In one embodiment, the FSH immuno-receptors of the invention can be used for diagnosing the presence of FSHR on a tumor cell. In another embodiment, a cell comprises the isolated nucleic acid sequence encoding the follicle-stimulating hormone receptor (FSHR) binding immunoreceptor (IR) described herein.

In another aspect, the invention includes an isolated follicle-stimulating hormone receptor (FSHR) binding immunoreceptor (IR) comprising a FSHR binding domain, a transmembrane domain, and a signaling domain, wherein the FSHR binding domain comprises a follicle-stimulating hormone (FSH) or fragment thereof, a FSHR antagonist or fragment thereof, or an anti-FSHR agonist or fragments thereof. In one embodiment, a cell comprises the isolated follicle-stimulating hormone receptor (FSHR) binding immunoreceptor (IR) described herein.

In yet another aspect, the invention includes a modified cell comprising a nucleic acid sequence encoding a follicle-stimulating hormone receptor (FSHR) binding immunoreceptor (IR), wherein the FSHR binding IR comprises a FSHR binding domain, a transmembrane domain, and a signaling domain, and wherein the FSHR binding domain comprises a follicle-stimulating hormone (FSH) or fragment thereof, a FSHR antagonist or fragment thereof, or an anti-FSHR agonist or fragments thereof. In one embodiment, the cell is selected from a T cell, a natural killer (NK) cell, a cytotoxic T lymphocyte (CTL), and a regulatory T cell.

In one embodiment, the FSHR binding IR specifically binds to FSHR expressed by tumor cells and/or tumor vasculature. In another embodiment, the FSHR binding domain of the immunoreceptor specifically binds to FSHR expressed by tumor cells and/or tumor vasculature. The tumor cells may include cells from a cancer selected from ovarian cancer, renal cell carcinoma, bladder cancer, kidney cancer, testicular cancer, prostate cancer, breast cancer, colon cancer, pancreatic cancer, lung cancer, liver cancer, stomach cancer and any combination thereof.

FSHR Binding Domain

In one embodiment, the FSHR binding domain may include a follicle-stimulating hormone (FSH) or fragment thereof, a FSHR antagonist or fragment thereof, anti-FSHR antibody or fragment thereof, or an anti-FSHR agonist or fragment thereof.

In one embodiment, the FSHR binding domain comprises an amino acid sequence derived from a follicle stimulating hormone (FSH) molecule. The FSHR binding domain includes fragments, peptides, or polypeptide sequences derived from a follicle stimulating hormone molecule. In one embodiment, the FSHR binding domain comprises peptides or polypeptides from FSH. In another embodiment, the FSHR binding domain comprises anti-FSHR peptides 33-53. In yet another embodiment, the FSHR binding domain comprises anti-FSHR peptides 51-65. In still yet another embodiment, the FSHR binding domain comprises anti-FSHR peptides 81-95.

The FSHR binding domain may include any fragment of a follicle stimulating hormone (FSH) molecule. In some embodiments, the FSHR binding domain comprises at least 10 amino acids in length of a FSH molecule. The FSHR binding domain may include at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more amino acids of a FSH molecule. In one embodiment, the FSHR binding domain comprises about 6 to about 40 amino acids of a FSH molecule. In another embodiment, the FSHR binding domain comprises about 10 to about 30 amino acids of a FSH molecule. In yet another embodiment, the FSHR binding domain comprises about 15 to about 25 amino acids of a FSH molecule. In still another embodiment, the FSH fragment retains the capacity to bind to a FSHR.

The FSHR immunoreceptor may include FSHR binding domains that are homologous to the anti-FSHR peptides described herein. The homologous anti-FSHR peptides may have 80%, 81%, 82%, 83%, 84%, 85%, 86%, 87%, 88%, 89%, 90%, 91%, 92%, 93%, 94%, 95%, 96%, 97%, 98%, 99%, or greater homology to the anti-FSHR peptides described herein.

The FSHR immunoreceptor may be encoded by a nucleic acid comprising a nucleic acid encoding a FSHR binding domain derived from a follicle stimulating hormone (FSH) molecule. The nucleic acid encoding a FSHR binding domain includes nucleotide sequences or fragments thereof derived from a nucleic acid encoding a follicle stimulating hormone molecule. In one embodiment, the nucleic acid encoding a FSHR binding domain comprises a nucleotide sequence or fragment thereof encodes an anti-FSHR peptides 33-53. In yet another embodiment, the nucleic acid encoding a FSHR binding domain comprises a nucleotide sequence or fragment thereof encodes an anti-FSHR peptides 51-65. In still yet another embodiment, the nucleic acid encoding a FSHR binding domain comprises a nucleotide sequence or fragment thereof encodes an anti-FSHR peptides 81-95.

The FSHR immunoreceptor may be encoded by a nucleic acid encoding a FSHR binding domain comprising a nucleic acid sequence having 80%, 81%, 82%, 83%, 84%, 85%, 86%, 87%, 88%, 89%, 90%, 91%, 92%, 93%, 94%, 95%, 96%, 97%, 98%, 99%, or greater identity to the nucleic acid encoding the anti-FSHR peptides described herein.

The FSHR binding domain may include a FSHR antagonist or fragment thereof, or an anti-FSHR agonist or fragment thereof. Example of FSHR antagonists and anti-FSHR agonists include, but are not limited to, urofollitropin, clorifollitropin alfa, suramin, cyclic and acyclic α and β aminocarboxamide derivatives, thiazolidine derivatives, biaryl derivatives, and thienopyrimidine derivatives.

In another embodiment, the FSHR binding immunoreceptor specifically binds to FSHR expressed by tumor cells and/or tumor vasculature.

Transmembrane Domain

With respect to the transmembrane domain, the immunoreceptor can be designed to include a transmembrane domain that is fused to the FSHR binding domain of the immunoreceptor. In one embodiment, the transmembrane domain that naturally is associated with one of the domains in the immunoreceptor is used. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Transmembrane regions of particular use may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. In some instances, a variety of human hinges can be employed as well including the human Ig (immunoglobulin) hinge. In one embodiment, the transmembrane domain comprises a CD8alpha hinge and transmembrane domain.

In another embodiment, the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

Signaling Domain

The signaling domain or intracellular signaling domain of the immunoreceptor is responsible for activation of at least one of the normal effector functions of the immune cell in which the immunoreceptor is expressed in. The term "effector function" refers to a specialized function of a cell. Effector function of a T cell, for example, may be cytolytic activity or helper activity including the secretion of cytokines. Thus the term "intracellular signaling domain" or "signaling domain" refers to the portion of a protein which transduces the effector function signal and directs the cell to perform a specialized function. While usually the entire signaling domain can be employed, in many cases it is not necessary to use the entire chain. To the extent that a truncated portion of the signaling domain is used, such truncated portion may be used in place of the intact chain as long as it transduces the effector function signal. The term signaling domain is thus meant to include any truncated portion of the signaling domain sufficient to transduce the effector function signal.

Examples of signaling domains for use in the immunoreceptor include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

Examples of ITAM containing primary cytoplasmic signaling sequences that are of particular use in the invention include those derived from TCR zeta, FcR gamma, FcR beta, CD3 gamma, CD3 delta, CD3 epsilon, CD5, CD22, CD79a, CD79b, and CD66d. It is particularly preferred that cytoplasmic signaling molecule in the immunoreceptor of the invention comprises a cytoplasmic signaling sequence derived from CD3-zeta. In one embodiment, the signaling domain of the immunoreceptor comprises a CD3 signaling domain.

In a preferred embodiment, the signaling domain of the immunoreceptor can be designed to comprise the CD3-zeta signaling domain by itself or combined with any other desired signaling domain(s) useful in the context of the immunoreceptor. For example, the signaling domain of the immunoreceptor can comprise a CD3 zeta chain portion and a costimulatory signaling region. The costimulatory signaling region refers to a portion of the immunoreceptor comprising the intracellular domain of a costimulatory molecule. A costimulatory molecule is a cell surface molecule other than an antigen receptor or its ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. Thus, while the invention in exemplified primarily with CD28 and 4-1BB as the co-stimulatory signaling element, other costimulatory elements are within the scope of the invention.

In one embodiment, the signaling domain is designed to comprise the signaling domain of CD3-zeta and the signaling domain of CD28. In another embodiment, the cytoplasmic domain is designed to comprise the signaling domain of CD3-zeta and the signaling domain of 4-1BB.

In one embodiment, the immunoreceptor of the invention further includes a co-stimulatory signaling region. The co-stimulatory domain may comprise an intracellular domain of a costimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, a ligand that specifically binds with CD83, and any combination thereof.

FSHR CAR

The present invention therefore encompasses a nucleic acid sequence encoding a CAR comprising a FSHR binding domain, a transmembrane domain and an intracellular signaling domain. The nucleic acid sequence may include a recombinant DNA construct comprising sequences of an antibody that specifically binds to FSHR, wherein the sequence of the antibody or a fragment thereof is operably linked to the nucleic acid sequence of an intracellular domain. The intracellular domain or otherwise the cytoplasmic domain comprises, a costimulatory signaling region and/or a zeta chain portion. The costimulatory signaling region refers to a portion of the CAR comprising the intracellular domain of a costimulatory molecule.

In one aspect, the invention includes an isolated nucleic acid sequence encoding a chimeric antigen receptor (CAR) comprising a follicle-stimulating hormone receptor (FSHR) binding domain, a transmembrane domain, a costimulatory signaling region, and a CD3 zeta signaling domain, wherein the FSHR binding domain comprises an anti-FSHR antibody or a fragment thereof. In one embodiment, a cell comprises the isolated nucleic acid sequence encoding the CAR described herein.

In another aspect, the invention includes an isolated chimeric antigen receptor (CAR) comprising a follicle-stimulating hormone receptor (FSHR) binding domain, a transmembrane domain, a costimulatory signaling region, and a CD3 zeta signaling domain, wherein the FSHR binding domain comprises anti-FSHR antibody or a fragment thereof. In one embodiment, a cell comprises the isolated CAR described herein.

In still yet another aspect, the invention includes a modified cell comprising a nucleic acid sequence encoding a chimeric antigen receptor (CAR) comprising a follicle-stimulating hormone receptor (FSHR) binding domain, a transmembrane domain, a costimulatory signaling region, and a CD3 zeta signaling domain, wherein the FSHR binding domain comprises an anti-FSHR antibody or a fragment thereof. In one embodiment, the cell is selected from a T cell, a natural killer (NK) cell, a cytotoxic T lymphocyte (CTL), and a regulatory T cell.

In one embodiment, the CAR specifically binds to FSHR expressed by tumor cells and/or tumor vasculature. In another embodiment, the FSHR binding domain of the CAR specifically binds to FSHR expressed by tumor cells and/or tumor vasculature. The tumor cells may include cells from a cancer selected from ovarian cancer, renal cell carcinoma, bladder cancer, kidney cancer, testicular cancer, prostate cancer, breast cancer, colon cancer, pancreatic cancer, lung cancer, liver cancer, stomach cancer and any combination thereof.

Between the extracellular domain and the transmembrane domain of the CAR, or between the cytoplasmic domain and the transmembrane domain of the CAR, there may be incorporated a spacer domain. As used herein, the term "spacer domain" generally means any oligo- or polypeptide that functions to link the transmembrane domain to, either the extracellular domain or, the cytoplasmic domain in the polypeptide chain. A spacer domain may comprise up to 300 amino acids, preferably 10 to 100 amino acids and most preferably 25 to 50 amino acids.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than as cloned molecules. In one embodiment, the CAR of the invention comprises a target-specific binding element otherwise referred to as an antigen binding moiety as described elsewhere herein. Examples of cell surface markers that may act as ligands for the antigen moiety domain in the CAR of the invention include those associated with viral, bacterial and parasitic infections, autoimmune disease and cancer cells.

FSHR Binding Domain

In a preferred embodiment, the FSHR binding domain portion of the CAR targets FSHR, including human FSHR. The choice of FSHR binding domain encompasses domains that specifically bind to FSHR. For example, the FSHR binding domain may include antibodies that specifically bind FSHR. FSHR antibodies are described in more detail elsewhere herein.

The FSHR binding domain can be any domain of an antibody that binds to FSHR including, but not limited to, monoclonal antibodies, polyclonal antibodies, synthetic antibodies, human antibodies, humanized antibodies, single fragment variable chains (scFv), and fragments thereof. Thus, in one embodiment, the FSHR binding domain of the CAR comprises a human antibody or a fragment thereof. In another embodiment, the FSHR binding domain is an antibody selected from the group consisting of a human antibody, humanized antibody, and fragment thereof. In yet another embodiment, the FSHR binding domain comprises a heavy and light chain. In still another embodiment, the FSHR binding domain is selected from the group consisting of a Fab fragment, a F(ab')$_2$ fragment, a Fv fragment, and a single chain Fv (scFv).

Transmembrane Domain

With respect to the transmembrane domain, the CAR can be designed to comprise a transmembrane domain that is fused to the extracellular domain of the CAR. In one embodiment, the transmembrane domain that naturally is associated with one of the domains in the CAR is used. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. In some instances, a variety of human hinges can be employed as well including the human Ig (immunoglobulin) hinge.

In one embodiment, the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

Signaling Domain and Costimulatory Domain

The signaling domain or otherwise the intracellular signaling domain of the CAR of the invention is responsible for activation of at least one of the normal effector functions of the immune cell in which the CAR has been placed in. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Preferred examples of intracellular signaling domains for use in the CAR of the invention include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary signaling sequences regulate primary activation of the TCR complex either in a stimulatory way, or in an inhibitory way. Primary signaling sequences that act in a stimulatory manner may contain signaling motifs which are known as immunoreceptor tyrosine-based activation motifs or ITAMs.

Examples of ITAM containing primary signaling sequences that are of particular use in the invention include those derived from TCR zeta, FcR gamma, FcR beta, CD3 gamma, CD3 delta, CD3 epsilon, CD5, CD22, CD79a, CD79b, and CD66d. It is particularly preferred that signaling molecule in the CAR of the invention comprises a signaling domain derived from CD3-zeta.

In a preferred embodiment, the signaling domain of the CAR can be designed to comprise the CD3-zeta signaling domain by itself or combined with any other desired cytoplasmic domain(s) useful in the context of the CAR of the invention. For example, the signaling domain of the CAR can comprise a CD3 zeta chain portion and a costimulatory signaling domain. The costimulatory signaling domain refers to a portion of the CAR comprising the intracellular domain of a costimulatory molecule. A costimulatory molecule is a cell surface molecule other than an antigen receptor or its ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. Thus, while the invention in exemplified primarily with CD28 and 4-1BB as the co-stimulatory signaling domains, other costimulatory domains are within the scope of the invention.

The signaling domains within the intracellular portion of the CAR of the invention may be linked to each other in a random or specified order. Optionally, a short oligo- or polypeptide linker, preferably between 2 and 10 amino acids in length may form the linkage. A glycine-serine doublet provides a particularly suitable linker.

In one embodiment, the signaling domain is designed to comprise the signaling domain of CD3-zeta and the signaling domain of CD28. In another embodiment, the signaling domain is designed to comprise the signaling domain of CD3-zeta and the signaling domain of 4-1BB.

Anti-FSHR Antibodies

The antibodies of the invention are characterized by particular functional features or properties. For example, the antibodies specifically bind to human FSHR. In some embodiments, the antibodies bind to FSHR with high affinity. The antibodies of the invention may specifically recognize naturally expressed FSHR protein on a cell. It may also be advantageous if the anti-FSHR antibodies do not cross-react with other surface molecules.

In one embodiment, the antibody contains heavy chain variable regions having CDRs 1, 2 and 3. In one embodiment, the antibody contains light chain variable regions having CDRs 1, 2 and 3.

Given that each of these antibodies binds to FSHR, the $V_H$ and $V_L$ sequences can be "mixed and matched" to create other anti-FSHR binding molecules of the invention. FSHR binding of such "mixed and matched" antibodies can be tested using the binding assays described herein, in the art, for example, in the Examples section (e.g., ELISAs). Preferably, when VH and VL chains are mixed and matched, a VH sequence from a particular VH/VL pairing is replaced with a structurally similar VH sequence. Likewise, preferably a VL sequence from a particular VH/VL pairing is replaced with a structurally similar VL sequence. It will be readily apparent to the ordinarily skilled artisan that novel VH and VL sequences can be created by substituting one or more VH and/or VL CDR region sequences with structurally similar sequences from the CDR sequences disclosed herein.

In one embodiment, the invention includes antibodies that comprise the heavy chain and light chain CDR1s, CDR2s and CDR3s. In certain embodiments, the antibody of the invention comprises a heavy chain variable region comprising CDR1, CDR2 and CDR3 sequences and a light chain variable region comprising CDR1, CDR2 and CDR3 sequences, wherein one or more of these CDR sequences comprise specified amino acid sequences or conservative modifications thereof, and wherein the antibodies retain the desired functional properties of the anti-FSHR antibodies of the invention. Accordingly, the invention provides an isolated antibody (e.g., scFv), or antigen binding portion thereof, comprising a heavy chain variable region comprising CDR1, CDR2, and CDR3 sequences and a light chain variable region comprising CDR1, CDR2, and CDR3 sequences.

In another embodiment, the invention includes antibodies that bind to the same epitope on human FSHR as any of the FSHR antibodies of the invention (i.e., antibodies that have the ability to cross-compete for binding to FSHR with any of the antibodies of the invention An antibody of the invention is prepared using an antibody having one or more of the VH and/or VL sequences disclosed herein as a starting material to engineer a modified antibody, which modified antibody may have altered properties as compared with the starting antibody. An antibody can be engineered by modifying one or more amino acids within one or both variable regions (i.e., VH and/or VL), for example within one or more CDR regions and/or within one or more framework regions. Additionally or alternatively, an antibody can be engineered by modifying residues within the constant region(s), for example to alter the effector function(s) of the antibody.

In certain embodiments, the small peptides of the invention comprise amino acids 33-53 or 51-65 of the human beta subunit FSH and target the beta subunit of the FSHR. In certain embodiments, the peptide comprises 5-30 amino acids. In other embodiments, peptide comprises 8-20 amino acids. The invention also provides methods of making such immuno-receptors.

Human Antibodies

For in vivo use of antibodies in humans, it may be preferable to use human antibodies. Completely human antibodies are particularly desirable for therapeutic treatment of human subjects. Human antibodies can be made by a variety of methods known in the art including phage display methods using antibody libraries derived from human immunoglobulin sequences, including improvements to these techniques. See, also, U.S. Pat. Nos. 4,444,887 and 4,716,111; and PCT publications WO 98/46645, WO 98/50433, WO 98/24893, WO98/16654, WO 96/34096, WO 96/33735, and WO 91/10741; each of which is incorporated herein by reference in its entirety. A human antibody can also be an antibody wherein the heavy and light chains are encoded by a nucleotide sequence derived from one or more sources of human DNA.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. For example, it has been described that the homozygous deletion of the antibody heavy chain joining region (JH) gene in chimeric and germ-line mutant mice results in complete inhibition of endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Antibodies directed against the target of choice can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies, including, but not limited to, IgG1 (gamma 1) and IgG3. For an overview of this technology for producing human antibodies, see, Lonberg and Huszar (Int. Rev. Immunol., 13:65-93 (1995)). For a detailed discussion of this technology for producing human antibodies and human monoclonal antibodies and protocols for producing such antibodies, see, e.g., PCT Publication Nos. WO 98/24893, WO 96/34096, and WO 96/33735; and U.S. Pat. Nos. 5,413,923; 5,625,126; 5,633, 425; 5,569,825; 5,661,016; 5,545,806; 5,814,318; and 5,939,598, each of which is incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above. For a specific discussion of transfer of a human germ-line immunoglobulin gene array in germ-line mutant mice that will result in the production of human antibodies upon antigen challenge see, e.g., Jakobovits et al., Proc. Natl. Acad. Sci. USA, 90:2551 (1993); Jakobovits et al., Nature, 362:255-258 (1993); Bruggermann et al., Year in Immunol., 7:33 (1993); and Duchosal et al., Nature, 355:258 (1992).

Human antibodies can also be derived from phage-display libraries (Hoogenboom et al., J. Mol. Biol., 227:381 (1991); Marks et al., J. Mol. Biol., 222:581-597 (1991); Vaughan et al., Nature Biotech., 14:309 (1996)). Phage display technology (McCafferty et al., Nature, 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for their review see, e.g., Johnson, Kevin S, and Chiswell, David J., Current Opinion in Structural Biology 3:564-571 (1993). Several sources of V-gene segments can be used for phage display. Clackson et al., Nature, 352:624-628 (1991) isolated a diverse array of anti-oxazolone antibodies from a small random combinatorial library of V genes derived from the spleens of unimmunized mice. A repertoire of V genes from unimmunized human donors can be constructed and antibodies to a diverse array of antigens (including self-antigens) can be isolated essentially following the techniques described by Marks et al., J. Mol. Biol., 222:581-597 (1991), or Griffith et al., EMBO J., 12:725-734 (1993). See, also, U.S. Pat. Nos. 5,565,332 and 5,573,905, each of which is incorporated herein by reference in its entirety.

Human antibodies may also be generated by in vitro activated B cells (see, U.S. Pat. Nos. 5,567,610 and 5,229,275, each of which is incorporated herein by reference in its entirety). Human antibodies may also be generated in vitro using hybridoma techniques such as, but not limited to, that described by Roder et al. (Methods Enzymol., 121:140-167 (1986)).

Humanized Antibodies

Alternatively, in some embodiments, a non-human antibody is humanized, where specific sequences or regions of the antibody are modified to increase similarity to an antibody naturally produced in a human. In one embodiment, the antigen binding domain is humanized.

A "humanized" antibody retains a similar antigenic specificity as the original antibody. However, using certain methods of humanization, the affinity and/or specificity of binding of the antibody for human CD3 antigen may be increased using methods of "directed evolution," as described by Wu et al., J. Mol. Biol., 294:151 (1999), the contents of which are incorporated herein by reference herein in their entirety.

A humanized antibody has one or more amino acid residues introduced into it from a source which is nonhuman. These nonhuman amino acid residues are often referred to as "import" residues, which are typically taken from an "import" variable domain. Thus, humanized antibodies comprise one or more CDRs from nonhuman immunoglobulin molecules and framework regions from human. Humanization of antibodies is well-known in the art and can essentially be performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody, i.e., CDR-grafting (EP 239,400; PCT Publication No. WO 91/09967; and U.S. Pat. Nos. 4,816,567; 6,331,415; 5,225,539; 5,530,101; 5,585,089; 6,548,640, the contents of which are incorporated herein by reference herein in their entirety). In such humanized chimeric antibodies, substantially less than an intact human variable domain has been substituted by the corresponding sequence from a nonhuman species. In practice, humanized antibodies are typically human antibodies in which some CDR residues and possibly some FR residues are substituted by residues from analogous sites in rodent antibodies. Humanization of antibodies can also be achieved by veneering or resurfacing (EP 592,106; EP 519,596; Padlan, 1991, Molecular Immunology, 28(4/5):489-498; Studnicka et al., Protein Engineering, 7(6):805-814 (1994); and Roguska et al., PNAS, 91:969-973 (1994)) or chain shuffling (U.S. Pat. No. 5,565,332), the contents of which are incorporated herein by reference herein in their entirety.

The choice of human variable domains, both light and heavy, to be used in making the humanized antibodies is to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151:2296 (1993); Chothia et al., J. Mol. Biol., 196:901 (1987), the contents of which are incorporated herein by reference herein in their entirety). Another method uses a particular framework derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993), the contents of which are incorporated herein by reference herein in their entirety).

Antibodies can be humanized with retention of high affinity for the target antigen and other favorable biological properties. According to one aspect of the invention, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind the target antigen. In this way, FR residues can be selected and combined from the recipient and import sequences so that the desired antibody characteristic, such as increased affinity for the target antigen, is achieved. In general, the CDR residues are directly and most substantially involved in influencing antigen binding.

Vectors

The present invention also provides vectors in which the isolated nucleic acid sequence of the present invention is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

In brief summary, the expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al., Molecular Cloning: A Laboratory Manual, volumes 1-3 ($3^{rd}$ ed., Cold Spring Harbor Press, NY 2001), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

An example of a promoter is the EF1alpha promoter. An additional example includes the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al., Molecular Cloning: A Laboratory Manual, volumes 1-3 ($3^{rd}$ ed., Cold Spring Harbor Press, NY 2001).

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle). In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Sources of T Cells

Prior to expansion and genetic modification, a source of T cells is obtained from a subject. The term "subject" is intended to include living organisms in which an immune response can be elicited (e.g., mammals). Examples of subjects include humans, dogs, cats, mice, rats, and transgenic species thereof. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art, may be used. In certain embodiments of the present invention, T cells can be obtained from a unit of blood collected from a subject using any number of techniques known to the skilled artisan, such as Ficoll™ separation. In one preferred embodiment, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Again, surprisingly, initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, Ca-free, Mg-free PBS, PlasmaLyte A, or other saline solution with or without buffer. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL gradient or by counterflow centrifugal elutriation. A specific subpopulation of T cells, such as $CD3^+$, $CD28^+$, $CD4^+$, $CD8^+$, $CD45RA^+$, and $CD45RO^+$ T cells, can be further isolated by positive or negative selection techniques. For example, in one embodiment, T cells are isolated by incubation with anti-$CD3^3$/anti-CD28 (i.e., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells which typically express $CD4^+$, $CD25^+$, $CD62L^{hi}$, $GITR^+$, and $FoxP3^+$. Alternatively, in certain embodiments, T regulatory cells are depleted by anti-CD25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of $CD8^+$ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, $CD4^+$ T cells express higher levels of CD28 and are more efficiently captured than $CD8^+$ T cells in dilute concentrations. In one embodiment, the concentration of cells used is $5 \times 10^6$/ml. In other embodiments, the concentration used can be from about $1 \times 10^5$/ml to $1 \times 10^6$/ml, and any integer value in between.

In other embodiments, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain embodiments, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993). In a further embodiment, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g., Rituxan.

In a further embodiment of the present invention, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Activation and Expansion of T Cells

T cells are activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells of the invention are expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either $CD4^+$ T cells or $CD8^+$ T cells, an anti-CD3 antibody and an anti-CD28 antibody. Examples of an anti-CD28 antibody include 9.3, B-T3, XR-CD28 (Diaclone, Besançon, France) can be used as can other methods commonly known in the art (Berg et al., *Transplant Proc.* 30(8):3975-3977, 1998; Haanen et al., *J. Exp. Med.* 190(9):13191328, 1999; Garland et al., *J. Immunol Meth.* 227(1-2):53-63, 1999).

In certain embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one embodiment, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In one embodiment, a 1:1 ratio of each antibody bound to the beads for $CD4^+$ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular embodiment an increase of from about 1 to about 3 fold is observed as compared to the expansion observed using a ratio of 1:1. In one embodiment, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain embodiments of the invention, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In one preferred embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one embodiment, a ratio of particles to cells of 1:1 or less is used. In one particular embodiment, a preferred particle: cell ratio is 1:5. In further embodiments, the ratio of particles to cells can be varied depending on the day of stimulation. For example, in one embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type.

In further embodiments of the present invention, the cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one embodiment the cells (for example, $10^4$ to $10^9$ T cells) and beads (for example, DYNABEADS® M-450 CD3/CD28 T paramagnetic beads at a ratio of 1:1) are combined in a buffer, preferably PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8+ T cells that normally have weaker CD28 expression.

In one embodiment of the present invention, the mixture may be cultured for several hours (about 3 hours) to about 14 days or any hourly integer value in between. In another embodiment, the mixture may be cultured for 21 days. In one embodiment of the invention the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α. or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

T cells that have been exposed to varied stimulation times may exhibit different characteristics. For example, typical blood or apheresed peripheral blood mononuclear cell products have a helper T cell population ($T_H$, CD4$^+$) that is greater than the cytotoxic or suppressor T cell population ($T_C$, CD8$^+$). Ex vivo expansion of T cells by stimulating CD3 and CD28 receptors produces a population of T cells that prior to about days 8-9 consists predominately of $T_H$ cells, while after about days 8-9, the population of T cells comprises an increasingly greater population of $T_C$ cells. Accordingly, depending on the purpose of treatment, infusing a subject with a T cell population comprising predominately of $T_H$ cells may be advantageous. Similarly, if an antigen-specific subset of $T_C$ cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Therapeutic Application

The isolated nucleic acid sequences described herein, the encoded immunoreceptor or CAR, or cells comprising either the isolated nucleic acid sequences or the encoded immunoreceptor or CAR may be included in a composition for therapy. The composition may include a pharmaceutical composition and further include a pharmaceutically acceptable carrier. A therapeutically effective amount of the pharmaceutical composition comprising the immunoreceptor or CAR may be administered.

In one aspect, the invention includes a method for stimulating a T cell-mediated immune response to a thyroid cell population in a mammal, the method comprising administering to a subject an effective amount of a modified cell that expresses a follicle stimulating hormone receptor (FSHR) immunoreceptor (IR), wherein the FSHR binding IR comprises a FSHR binding domain, a transmembrane domain, and a signaling domain, and wherein the FSHR binding domain comprises a follicle-stimulating hormone (FSH) or fragment thereof, a FSHR antagonist or fragment thereof, or an anti-FSHR agonist or fragments thereof.

In another aspect, the invention includes a method of treating a condition in a subject, the method comprising administering to the subject a modified T cell that expresses a follicle stimulating hormone receptor (FSHR) binding immunoreceptor (IR), wherein the FSHR binding IR comprises a FSHR binding domain, a transmembrane domain, and a signaling domain, and wherein the FSHR binding domain comprises a follicle-stimulating hormone (FSH) or fragment thereof, a FSHR antagonist or fragment thereof, or an anti-FSHR agonist or fragments thereof. In one embodiment, the condition is a cancer selected from ovarian cancer, renal cell carcinoma, bladder cancer, kidney cancer, testicular cancer, prostate cancer, breast cancer, colon cancer, pancreatic cancer, lung cancer, liver cancer, stomach cancer and any combination thereof. In another embodiment, the modified T cell is autologous to the subject. In another embodiment, the method further includes administering an antitumor vaccine to the subject. In yet another embodiment, the modified T cell and the antitumor vaccine are co-administered to the subject.

In yet another aspect, the invention includes a method for stimulating a T cell-mediated immune response to a thyroid cell population in a mammal, the method comprising administering to a subject an effective amount of a modified cell that expresses a chimeric antigen receptor comprising a follicle-stimulating hormone receptor (FSHR) binding domain, a transmembrane domain, a costimulatory signaling region, and a CD3 zeta signaling domain, wherein the FSHR binding domain comprises an anti-FSHR antibody or a fragment thereof.

In still another aspect, the invention includes a method of treating a subject with cancer, the method comprising administering to the subject a modified T cell that expresses a chimeric antigen receptor comprising a follicle-stimulating hormone receptor (FSHR) binding domain, a transmembrane domain, a costimulatory signaling region, and a CD3 zeta signaling domain, wherein the FSHR binding domain comprises an anti-FSHR antibody or a fragment thereof. In one embodiment, the cancer is selected from ovarian cancer, renal cell carcinoma, bladder cancer, kidney cancer, testicular cancer, prostate cancer, breast cancer, colon cancer, pancreatic cancer, lung cancer, liver cancer, stomach cancer and any combination thereof. In another embodiment, the modified T cell is autologous to the subject. In another embodiment, the method further includes administering an antitumor vaccine to the subject. In yet another embodiment, the modified T cell and the antitumor vaccine are co-administered to the subject.

In another embodiment, the cells described herein may be used for the manufacture of a medicament for the treatment of an immune response in a subject in need thereof. In yet another embodiment, the cells described herein may be used for the manufacture of a medicament for the treatment of cancer in a subject in need thereof.

The procedure for ex vivo expansion of hematopoietic stem and progenitor cells is described in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In another aspect, the invention pertains to a method of treating a disease or condition associated with enhanced immunity in a subject. The method comprises administering to a subject an effective amount of a modified cell that expresses the immunoreceptor or CAR of the present invention such that the disease or condition associated with enhanced immunity is treated in the subject. Particularly preferred diseases or conditions associated with enhanced immunity include autoimmune diseases such as Acquired Immunodeficiency Syndrome (AIDS), alopecia areata, ankylosing spondylitis, antiphospholipid syndrome, autoimmune Addison's disease, autoimmune hemolytic anemia, autoimmune hepatitis, autoimmune inner ear disease (AIED), autoimmune lymphoproliferative syndrome (ALPS), autoimmune thrombocytopenic purpura (ATP), Behcet's disease, cardiomyopathy, celiac sprue-dermatitis hepetiformis; chronic fatigue immune dysfunction syndrome (CFIDS), chronic inflammatory demyelinating polyneuropathy (CIPD), cicatricial pemphigold, cold agglutinin disease, crest syndrome, Crohn's disease, Degos' disease, dermatomyositis-juvenile, discoid lupus, essential mixed cryoglobulinemia, fibromyalgia-fibromyositis, Graves' disease, Guillain-Barre syndrome, Hashimoto's thyroiditis, idiopathic pulmonary fibrosis, idiopathic thrombocytopenia purpura (ITP), IgA nephropathy, insulin-dependent diabetes mellitus, juvenile chronic arthritis (Still's disease), juvenile rheumatoid arthritis, Meniere's disease, mixed connective tissue disease, multiple sclerosis, myasthenia gravis, pernacious anemia, polyarteritis *nodosa*, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomena, Reiter's syndrome, rheumatic fever, rheumatoid arthritis, sarcoidosis, scleroderma (progressive systemic sclerosis (PSS), also known as systemic sclerosis (SS)), Sjogren's syndrome, stiff-man syndrome, systemic lupus erythematosus, Takayasu arteritis, temporal arteritis/giant cell arteritis, ulcerative colitis, uveitis, vitiligo, Wegener's granulomatosis, and any combination thereof and any combination thereof.

The present invention includes a type of cellular therapy where cells are genetically modified and infused to a recipient in need thereof. In one embodiment, a method is disclosed for adoptive transfer therapy comprising administering a population of the modified cells to a subject in need thereof. The cells are able to kill the diseased cells in the subject. Unlike traditional antibody therapies, the modified cells described herein are able to replicate in vivo resulting in long-term persistence that can lead to sustained disease control. In various embodiments, the cells administered to the patient, or their progeny, persist in the patient for at least four months, five months, six months, seven months, eight months, nine months, ten months, eleven months, twelve months, thirteen months, fourteen month, fifteen months, sixteen months, seventeen months, eighteen months, nineteen months, twenty months, twenty-one months, twenty-two months, twenty-three months, two years, three years, four years, or five years after administration of the cells to the patient.

The fully-human or humanized immunoreceptor- or CAR-modified cells of the invention may be a type of vaccine for ex vivo immunization and/or in vivo therapy in a mammal. Preferably, the mammal is a human.

Ex vivo procedures are well known in the art as discussed more fully above. Briefly, cells are isolated from a mammal (preferably a human) and genetically modified (i.e., transduced or transfected in vitro) with a vector comprising the isolated nucleic acid sequence disclosed elsewhere herein. The modified cells can be administered to a mammalian recipient to provide a therapeutic benefit. The mammalian recipient may be a human and the modified cells can be autologous with respect to the recipient. Alternatively, the cells can be allogeneic, syngeneic or xenogeneic with respect to the recipient.

Generally, the cells may be activated and expanded as described herein then utilized in the treatment and prevention of diseases that arise in individuals who are immunocompromised. In particular, the modified cells of the invention are used in the treatment of diseases, disorders and conditions associated with dysregulated expression of FSHR. In certain embodiments, the cells of the invention are used in the treatment of patients at risk for developing diseases, disorders and conditions associated with dysregulated expression of FSHR. Thus, the present invention provides methods for the treatment or prevention of diseases, disorders and conditions associated with dysregulated expression of FSHR.

The modified cells generated as described herein can also be used to treat inflammatory disorders. Examples of inflammatory disorders include but are not limited to, chronic and acute inflammatory disorders. Examples of inflammatory disorders include Alzheimer's disease, asthma, atopic allergy, allergy, atherosclerosis, bronchial asthma, eczema, glomerulonephritis, graft vs. host disease, hemolytic anemias, osteoarthritis, sepsis, stroke, transplantation of tissue and organs, vasculitis, diabetic retinopathy and ventilator induced lung injury.

Cells of the invention can be administered in dosages and routes and at times to be determined in appropriate preclinical and clinical experimentation and trials. Cell compositions may be administered multiple times at dosages within these ranges. Administration of the cells of the invention may be combined with other methods useful to treat the desired disease or condition as determined by those of skill in the art.

The cells of the invention to be administered may be autologous, allogeneic or xenogeneic with respect to the subject undergoing therapy.

The administration of the cells of the invention may be carried out in any convenient manner known to those of skill in the art. The cells of the present invention may be administered to a subject by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In other instances, the cells of the invention are injected directly into a site of inflammation in the subject, a local disease site in the subject, a lymph node, an organ, a tumor, and the like.

The cells described herein can also be administered using any number of matrices. The present invention utilizes such matrices within the novel context of acting as an artificial lymphoid organ to support, maintain, or modulate the immune system, typically through modulation of T cells. Accordingly, the present invention can utilize those matrix compositions and formulations which have demonstrated utility in tissue engineering. Accordingly, the type of matrix that may be used in the compositions, devices and methods of the invention is virtually limitless and may include both biological and synthetic matrices. In one particular example, the compositions and devices set forth by U.S. Pat. Nos. 5,980,889; 5,913,998; 5,902,745; 5,843,069; 5,787,900; or 5,626,561 are utilized, as such these patents are incorporated herein by reference in their entirety. Matrices comprise features commonly associated with being biocompatible when administered to a mammalian host. Matrices may be formed from natural and/or synthetic materials. The matrices may be non-biodegradable in instances where it is desirable to leave permanent structures or removable structures in the body of an animal, such as an implant; or biodegradable. The matrices may take the form of sponges, implants, tubes, telfa pads, fibers, hollow fibers, lyophilized components, gels, powders, porous compositions, or nanoparticles. In addition, matrices can be designed to allow for sustained release of seeded cells or produced cytokine or other active agent. In certain embodiments, the matrix of the present invention is flexible and elastic, and may be described as a semisolid scaffold that is permeable to substances such as inorganic salts, aqueous fluids and dissolved gaseous agents including oxygen.

A matrix is used herein as an example of a biocompatible substance. However, the current invention is not limited to matrices and thus, wherever the term matrix or matrices appears these terms should be read to include devices and other substances which allow for cellular retention or cellular traversal, are biocompatible, and are capable of allowing traversal of macromolecules either directly through the substance such that the substance itself is a semi-permeable membrane or used in conjunction with a particular semi-permeable substance.

Pharmaceutical Compositions

Pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

It can generally be stated that a pharmaceutical composition comprising the T cells described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer activated T cells to a subject and then subsequently redraw blood (or have an apheresis performed), activate T cells therefrom according to the present invention, and reinfuse the patient with these activated and expanded T cells. This process can be carried out multiple times every few weeks. In certain embodiments, T cells can be activated from blood draws of from 10 ml to 400 ml. In certain embodiments, T cells are activated from blood draws of 20 ml, 30 ml, 40 ml, 50 ml, 60 ml, 70 ml, 80 ml, 90 ml, or 100 ml. Not to be bound by theory, using this multiple blood draw/multiple reinfusion protocol, may select out certain populations of T cells.

The administration of the subject compositions may be carried out in any convenient manner, including by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In one embodiment, the T cell compositions of the present invention are administered to a patient by intradermal or subcutaneous injection. In another embodiment, the T cell compositions of the present invention are preferably administered by i.v. injection. The compositions of T cells may be injected directly into a tumor, lymph node, or site of infection.

In certain embodiments of the present invention, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAM-PATH. In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

The materials and methods employed in these experiments are now described.
Engineering FSHR Immune Receptor (IR) Constructs:
Anti-FSHR Immunoreceptor (FSHR_IR) Construction.

Using pELNS vector based on previously used CAR constructs, FSHR specific peptides are cloned using novel BamHI and NheI digestion sites between the CD8a leader peptide and the transmembrane regions. Cloning into established vectors allows the creation of anti-FSHR IRs that contain either CD3ζ, CD3ζ/CD28, CD3ζ/4-1BB, under the control of the EF-1α promoter.
Recombinant Lentivirus Production.

High titer lentivirus is produced using standardized lab procedures (Song et al., Jr. Cancer Res. 71(13):4617-27, 2011; Carpenito et al., Proc Natl Acad Sci USA 106:3360-3365, 2009). Briefly, 293T cells were transfected with pVSV-G (VSV glycoprotein expression plasmid), pRSV.REV (Rev expression plasmid), pMDLg/p.RRE (Gag/Pol expression plasmid), and pELNS transfer plasmid using Lipofectamine 2000 (Invitrogen). The viral supernatant was harvested at 24 and 48 h post-transfection.

In all assays, lentiviral transduction of T cells are performed under conditions of optimal transduction efficiency and control green fluorescent protein (GFP) lentiviral transduction is performed in parallel cultures. The relative binding of recombinant FSHR protein to anti-FSHR IR is accessed via flow cytometric analysis utilizing biotinylated recombinant-FSHR protein. Quantitative flow cytometry analysis utilizing APC-conjugated Immuno-brite fluorospheres (Beckman Coulter, Fullerton, Calif.) is used to calculate the number of anti-FSHR immune receptors expressed on transduced T cells. In parallel, all anti-FSHR IR constructs are tested for their ability to bind to recombinant mouse FSHR protein. It is known in the art that peptides derived from a beta subunit of the human FSH also bind to the mouse FSHR (Grasso et al., Endocrinology 137:5370-5375, 1996; Grasso et al., Biol Reprod 58:821-825, 1998). As an antigen specificity control, irrelevant recombinant proteins mesothelin and/or folate receptor alpha (FRa) are tested for binding by flow cytometry.

Control IR T cell that recognize mesothelin (Lanitis et al., Mol Ther 20:633-643, 2012) or FRa (Song et al., Cancer Res 71:4617-4627, 2013) are included in these and functional assays.

Flow Cytometric Analysis

APC-Cy7 Mouse Anti-Human-CD3; FITC-anti-human-CD4; APC-anti-human-CD8; PE-human-CD45; APC-human-CD69 antibodies were purchased from (Biolegend). FSHR expression was detected using clone6266717 (R&D Systems). T-cell transduction was measured by GFP transgene expression. 7AAD (Biolegend) was used to assess viability. For in vivo T-cell quantification, 50 µL blood was obtained from mice via retro-orbital bleeding and labeled for human CD45, CD3, and CD8. Cell numbers were quantified using BD TruCount tubes per manufacturer's instructions. Flow cytometry data were analyzed using FlowJo software.

FSHR-PCR

Total RNA was extracted from $5 \times 10^6$ viable tumor cells using RNeasy Mini kit (Qiagen). RNA quantity and quality were verified using a NanoDrop 2000 spectrophotometer (Thermo). cDNA was generated from 1 µg total RNA using the High-Capacity-RNA-to-cDNA kit (Applied Biosystems). The human-FSHR was PCR-amplified using the following primers: 5'-CTCACCAAGCTTCGAGTCATC-CAA-3' (SEQ ID NO: 32) and 5'-GCTCATCTAGTTGGGT-TCCATT-3' (Gene ID: 2492, SEQ ID NO: 33), mouse-FSHR 5'-GGGATCTGGATGTCATCACT-3' (SEQ ID NO: 34) and 5'-GGAGAACACATCTGCCTCTA-3' (Gene ID: 14309, SEQ ID NO: 35).

Cytokine Release Assays and Intracellular Cytokine Staining (CBA)

Cytokine release assays were performed by co-culture of $1 \times 10^5$ FSHR-IR T-cells with FSHR-expressing CaOV3 and FSHR-negative 293T cells, or mouse FSHR-expressing ID8, as described previously (15). After 16 h, co-culture supernatants were assayed for presence of cytokines using an ELISA Kit (Biolegend) and Cytokine Bead Array (BD Biosciences) according to manufacturer's instructions.

Cytotoxicity fLuc-transduced targets were plated at $1 \times 10^4$/well in triplicate. T-cells were added at the indicated effector:target (E:T) ratios. Co-cultures were incubated overnight in phenol-free CM. The Extended-Glow Bioluminescent Reporter Gene Assay (Applied Biosystems) was used to measure residual luciferase activity from remaining targets, and lysis was calculated as follows: Percent Lysis=100-[(average signal from T-cell-treated wells)/(average signal from untreated target wells)×100].

Xenograft Model of OvCa

NOD/SCID/γ-chain-/- (NSG) mice were bred, treated, and maintained under pathogen-free conditions in-house under University of Pennsylvania IACUC-approved protocols. Six to twelve week old female mice were purchased from the University of Pennsylvania Stem Cell and Xenograft Core and $5 \times 10^6$ CaOV3-fLuc tumor cells were inoculated subcutaneously (5 mice/group). Twenty and 25 days later, mice were injected intraperitoneally with $6 \times 10^6$ T-cells. Tumor growth was assessed by weekly caliper measurements. Tumor volume was calculated using the following formula: V=1/2(length×width$^2$), where length is greatest longitudinal diameter and width is greatest transverse diameter.

Statistical Analysis

Student's t-test was used to evaluate differences in T-cells specific cytolysis and cytokine secretion. GraphPad Prism 4.0 (GraphPad Software) was used for the statistical calculations. P<0.05 was considered significant.

The results of the experiments are now described.

Figure 1J:
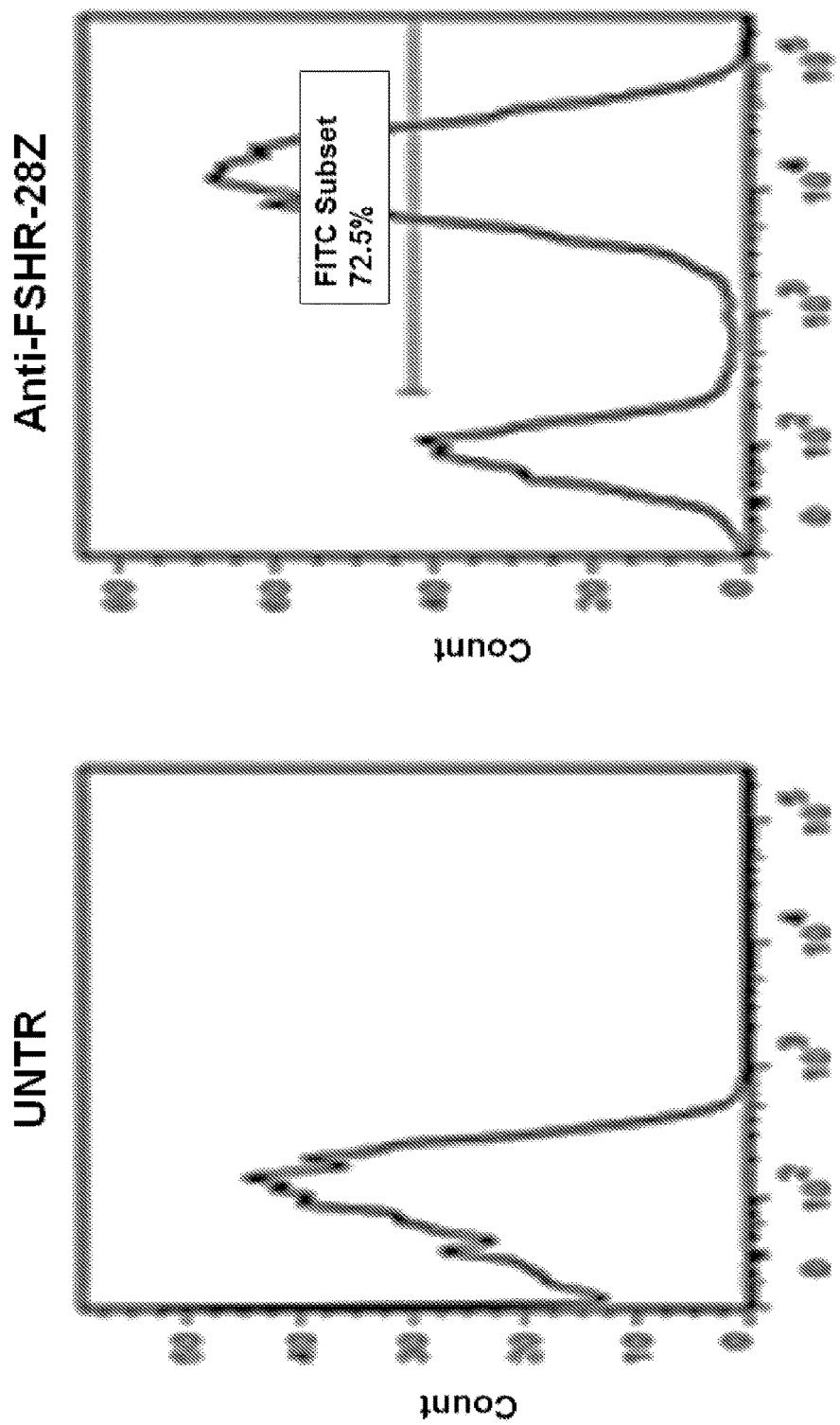
FIG. 1J: anti-FSHR IR transgene expression by human T cells after lentivirus based gene transfer detected via GFP expression.
Figure 4:
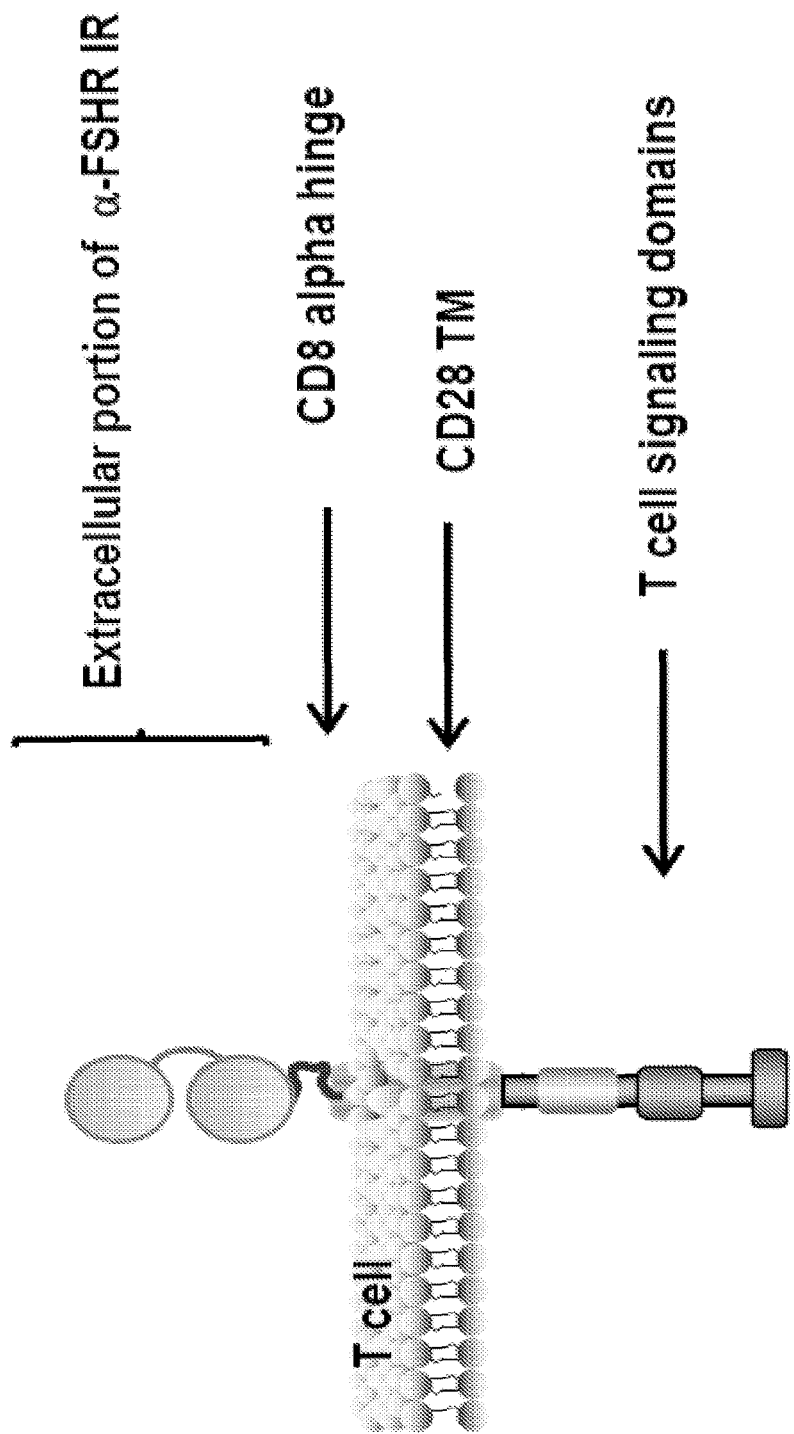
FIG. 4 are a schematic representing the anti-FSHR immune receptor; anti-FSHR IR. Schematic representation of anti-FSHR-Immune Receptor gene constructs containing extracellularly expressed peptides derived from FSH (specificity for FSHR) fused to the human CD3z cytosolic domain alone (anti-FSHR-IR-z) or in combination with the co-stimulatory module (and/or: 41BB/CD27/CD28).

Example 1: Peptide-Based Chimeric Immune-Receptor Construction and Expression Validation After amplification and the insertion of 3'-Bam-H1 and 5'-Nhe-1 restriction sites, PCR products were digested with Bam-HI and NheI enzymes and ligated into pELNS 2A GFP, a third generation self-inactivating lentiviral expression vector, containing humanCD28-CD3z signaling endodomains, under an EF-1a promoter (FIGS. 1A-1I), and referred to as anti-FSHR-IR-z and anti-FSHR-IR-28z (FIG. 1I). Anti-FSHR-28z IRs were transduced into freshly isolated human primary T cells utilizing lentiviral vectors. Five days following lentiviral transduction, the expression of anti-FSHR IR was determined by flow cytometry analysis based on GFP expression (FIG. 1J and FIGS. 3A-3B). A schematic of the immunoreceptor is shown in FIG. 4. Some FSHR-binding sites have been reported, including amino acid fragments 33-53, 51-65, and 81-95 of the FSHβ chain (Santa et al., Biochemistry 29, 1194-1200, 1990; Lum et al., Clinical breast cancer 4, 212-217, 2003 and Morbeck et al., Molecular and cellular endocrinology 97, 173-181, 1993). In particular, FSHβ 33-53 peptide appears functional when covalently attached to nanoparticles, providing high selectivity nanoparticle delivery to FSHR-expressing ovarian tumors (Zhang et al., Cancer research 69, 6506-6514, 2009). FSH peptides were cloned into previously validated lentiviral constructs with intracellular CD3z domain alone or with the CD28 costimulatory signaling domain in tandem (Song et al., Blood 119, 696-706, 2012), and referred to as anti-FSHR-IR-z and anti-FSHR-IR-28z (FIG. 1I).

Figure 2:
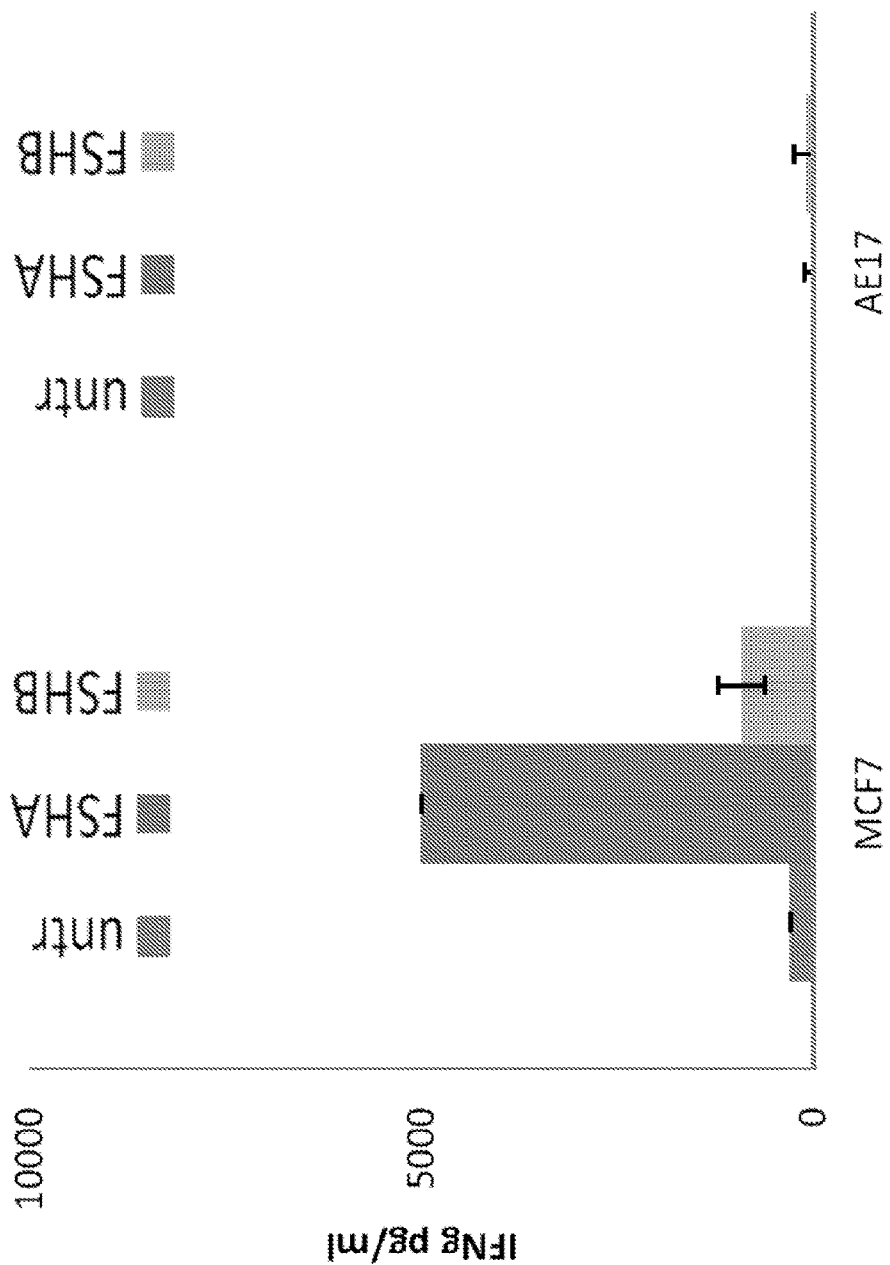
FIG. 2 is a histogram showing that anti-FSHR IR T cells produce IFN-g in response to stimulation with FSHR+ MCF7 tumor cells, but not AE17 cells lacking FSHR. FSHA indicates the 33-53 amino acid immune receptor; FSHR indicates the 51-65 immune receptor. IFN-g cytokine was measured from overnight cell culture supernatants by ELISA. (Mean pg/ml+/−SEM from triplicate wells is shown). Untransduced T cells serve as negative control.

Example 2: Cell Surface Expression of Anti-FSHR IR can Redirect Primary Human T Lymphocytes Against FSHR Positive (FSHR$^+$) Tumor Cell Targets Production of proinflammatory cytokines correlates with cytolytic function of T cells. Therefore, to define whether cell surface expression of anti-FSHR IR can redirect primary human T lymphocytes against FSHR$^+$ tumor cell targets, the levels of IFN-g cytokine released by activated anti-FSHR IR T cells was measured. For that purpose, FSHR positive MCF7 cell line (Breast Carcinoma), and AE17 (mouse mesothelioma), an FSHR negative cell line were utilized. As represented in FIGS. 2 and 5, high levels of IFN-gamma were detected in the cell culture supernatants of primary human T cell transduced to express anti-FSHR (33-53) -28z IR following 16 h culture with FSHR$^+$ MCF7 tumor cells. Anti-FSHR (33-53) IR T cells (referred to as FSH A) secreted higher amounts of IFN-gamma compared to T cells with the anti-FSHR (51-65) IR (FSH B) and control untransduced T cells.

Figures 6A, 6B:
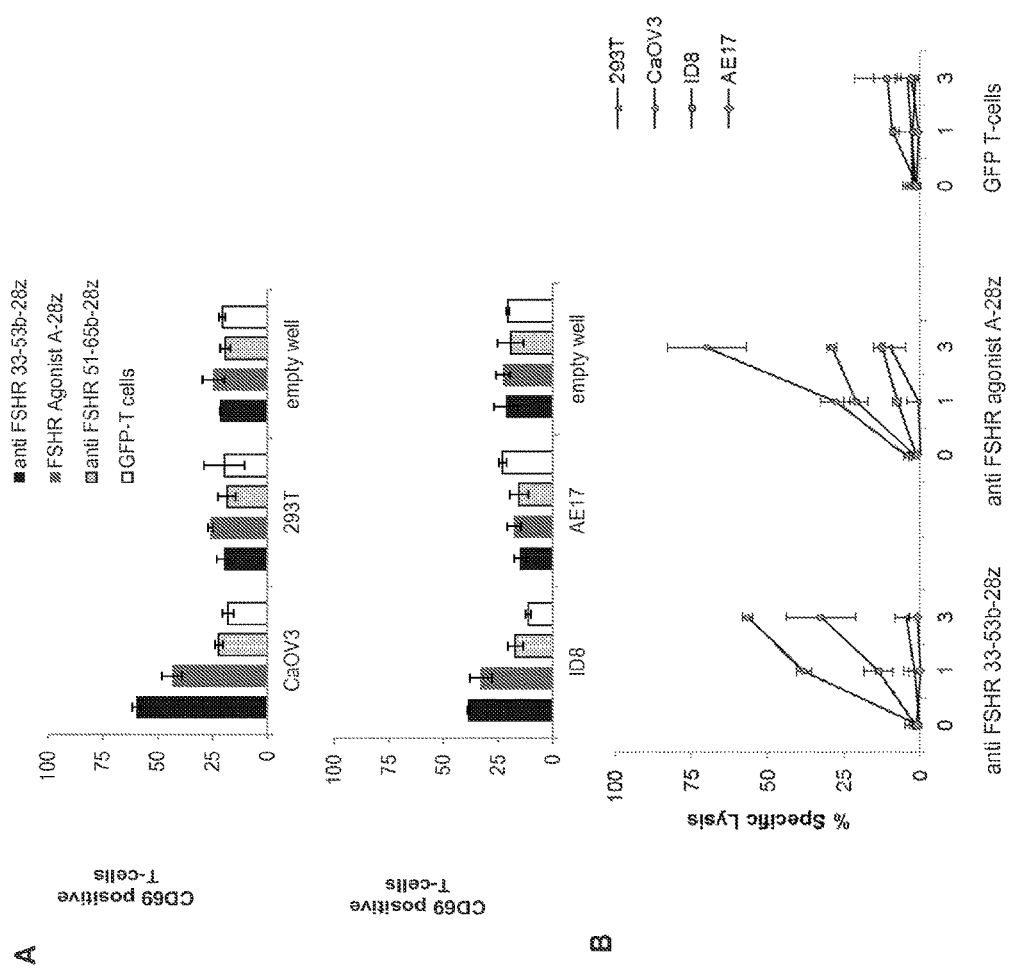
FIGS. 6A-6C are a series of histograms and graphs illustrating the cytotoxicity of anti-FSHR T-cells.
Figure 6C:
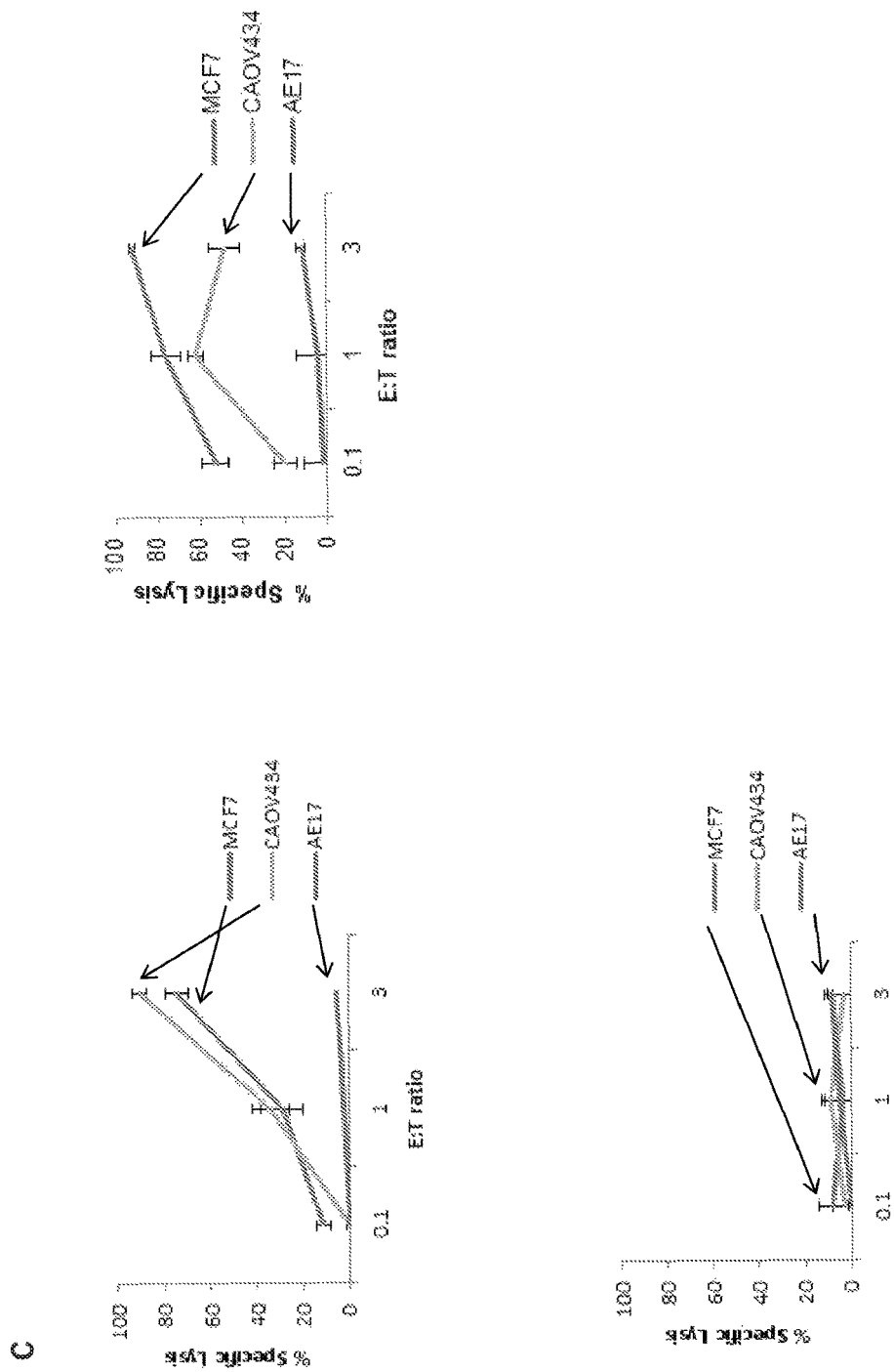

Importantly, no immunoreactivity against the FSHR negative EA17 tumor cell line by any FSHR IR T cells was observed (FIGS. 6A-6C). Furthermore, anti-FSHR (33-53)-28z IR T cells showed a specific immunoreactivity against other types of tumors, with varying expression of FSHR e.g., CaoV3 and OvCAR3 (FIGS. 6A-C and 7), thus confirming their specificity for FSHR antigen. In addition to the FSHR positive MCF7 cell line (Breast Carcinoma), anti-FSHR IR T cells secrete high levels of IFN-g when stimulated with the FSHR positive CAOV434 cell line (Ovarian Carcinoma) (FIG. 5). Importantly, immunorecognition and immunoresponse were observed by the anti-FHSR IR of mouse FSHR expressed on the surface of the mouse ID8 cells ovarian cancer cell line (Li et al., Mol Cell Endocrinol 267:26-37, 2007; Fong et al., J Ovarian Res 2:12, 209). While T cells expressing anti-FSHR (33-53)-28z IR and anti-FSHR (51-65)-28z IR recognize FSHR protein expressed on the cell surface and secrete IFN-g, they bind recombinant FSHR protein poorly (FIGS. 3A-3B).

Example 3: Development of an Anti-FSHR Immune Receptor for Targeting Ovarian Tumor Cells and Tumor Vasculature This invention provides an anti-FSHR immune receptor construct comprising FSHR-specific peptide derived from the natural FSHR ligand linked to intracellular CD3- and/or co-stimulatory signaling moieties such as CD28, and/or 4-1BB (example shown in FIG. 4) for transmission of activating T cell signals to IR T cells upon encounter with FHSR. This invention provides also means for testing this construct.

Figure 11A:
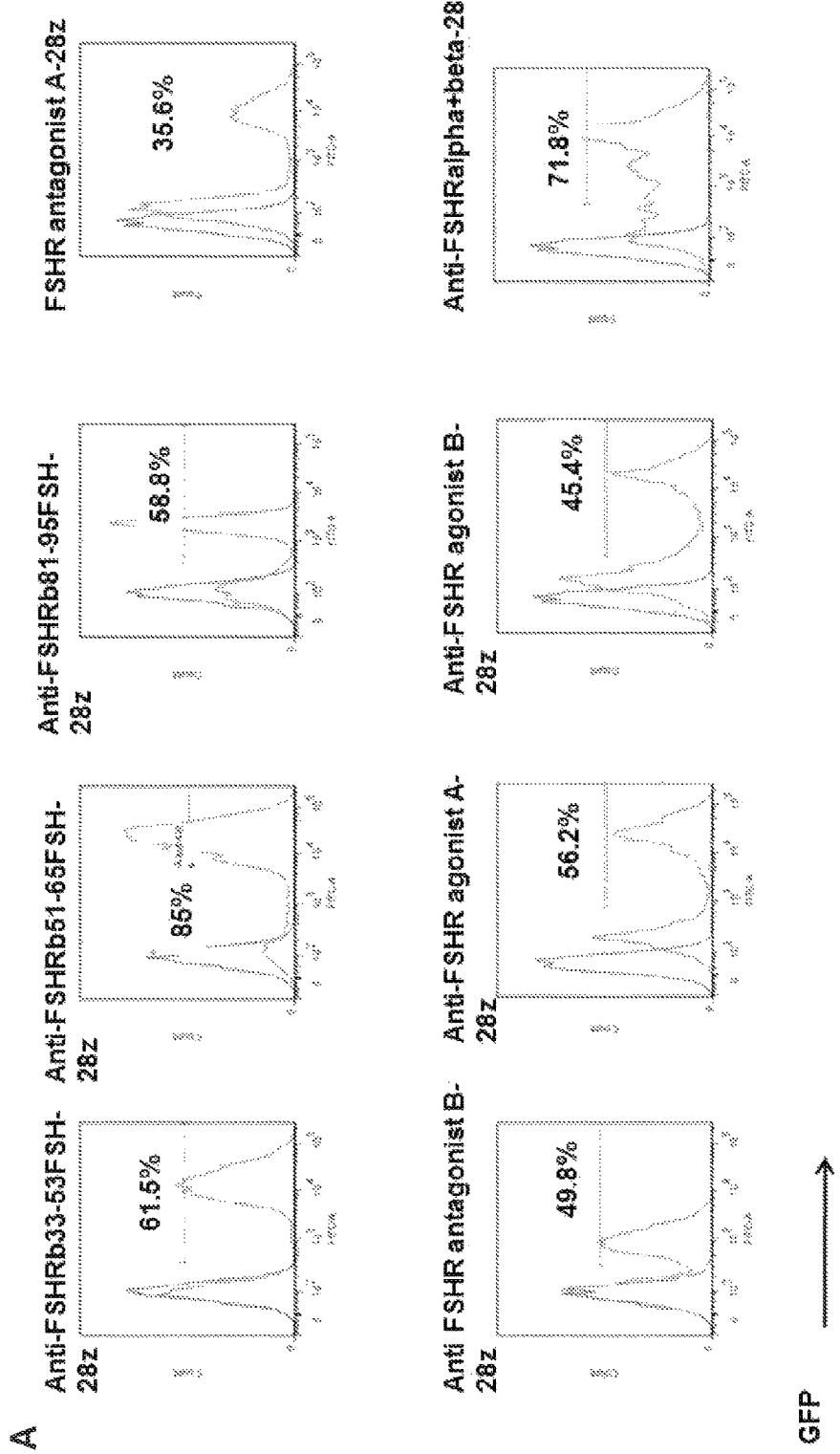
Figure 11B:
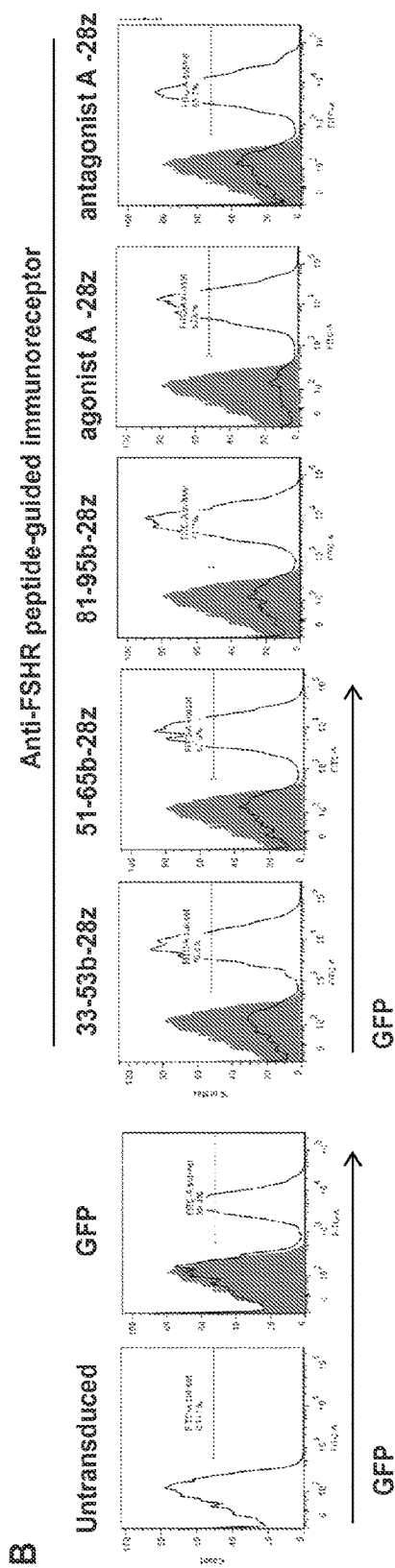

FSH is a heterodimeric glycoprotein gonadotropin, consisting of alpha and beta subunits. Several peptides composed of parts of either FSH beta subunit alone or beta and alpha subunits have been reported in the art to specifically bind to FSHR, as high affinity FSHR agonists or antagonists. The panel of anti-FSHR peptides designed for creation of the chimeric immune receptor are described herein. Lentiviral vectors encoding the various extracellular anti-FSHR peptides (FIG. 10) coupled with a cytosolic tail comprised of modular combinations of CD3δ plus 4-1BB and/or CD28 co-stimulatory domains were engineered (FSHR IR). Anti-FSHR IRs were synthesized (FIGS. 11A-11B), engineered into primary human T cells. A high transduction efficiency of primary human T-cells was achieved, as measured by co-expression of GFP (65-80%; FIG. 11B). Transduction efficiencies of all anti-FSHR-IR constructs were essentially identical. These constructs were validated in in vitro experiments for their ability to specifically bind to FSHR expressed on the FSHR positive cell surface and redirect T cell effector function (FIGS. 2, 5, 6A-6C, 7, 8A-8D, 9 and 12A-12D).

Figure 12A:
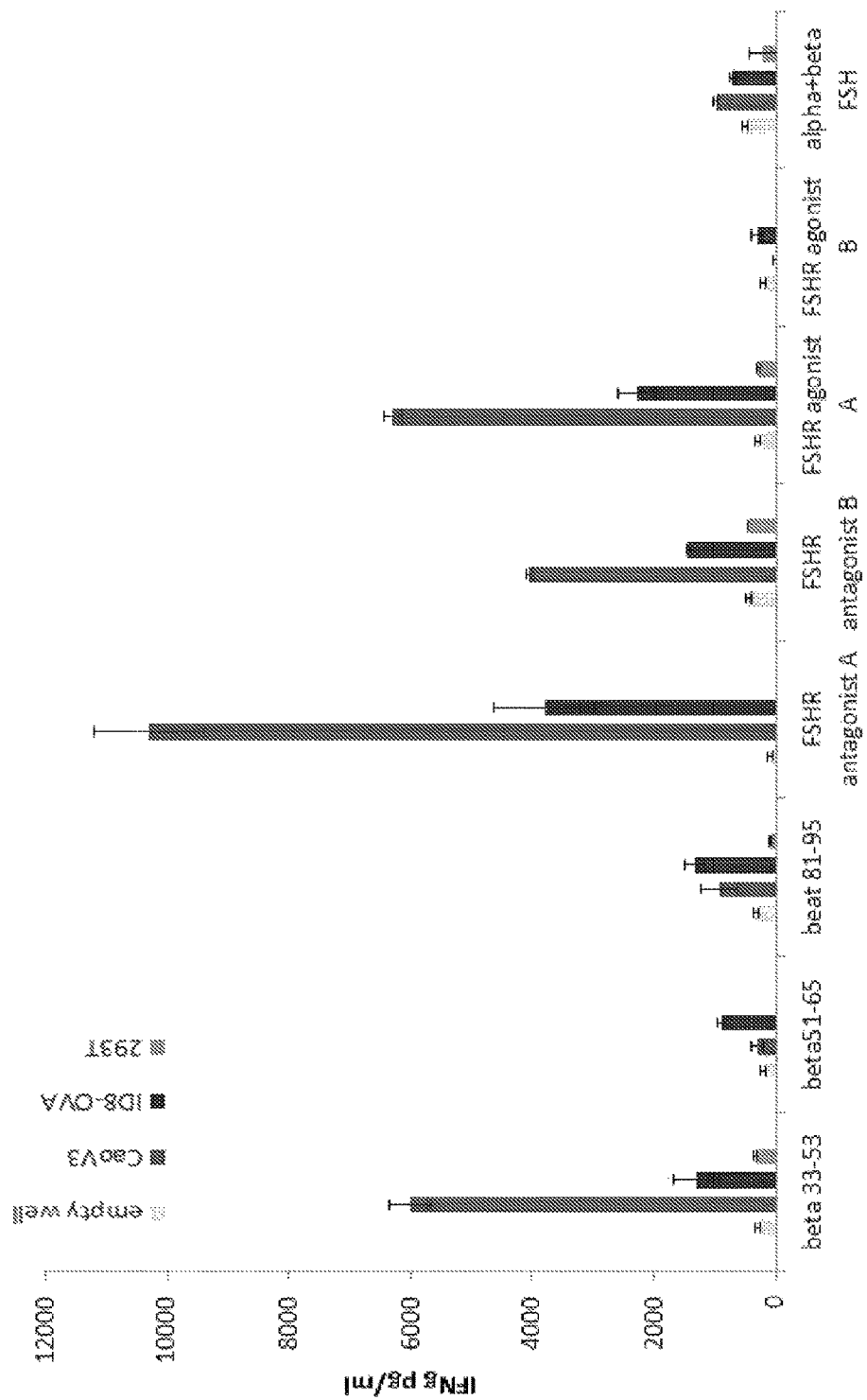
FIGS. 12A-12D are a series of is a graphs demonstrating that anti-FSHRT cells are reactive against cell surface expressed FSHR on human and mouse ovarian cancer cell lines.
Figures 12B, 12C, 12D:
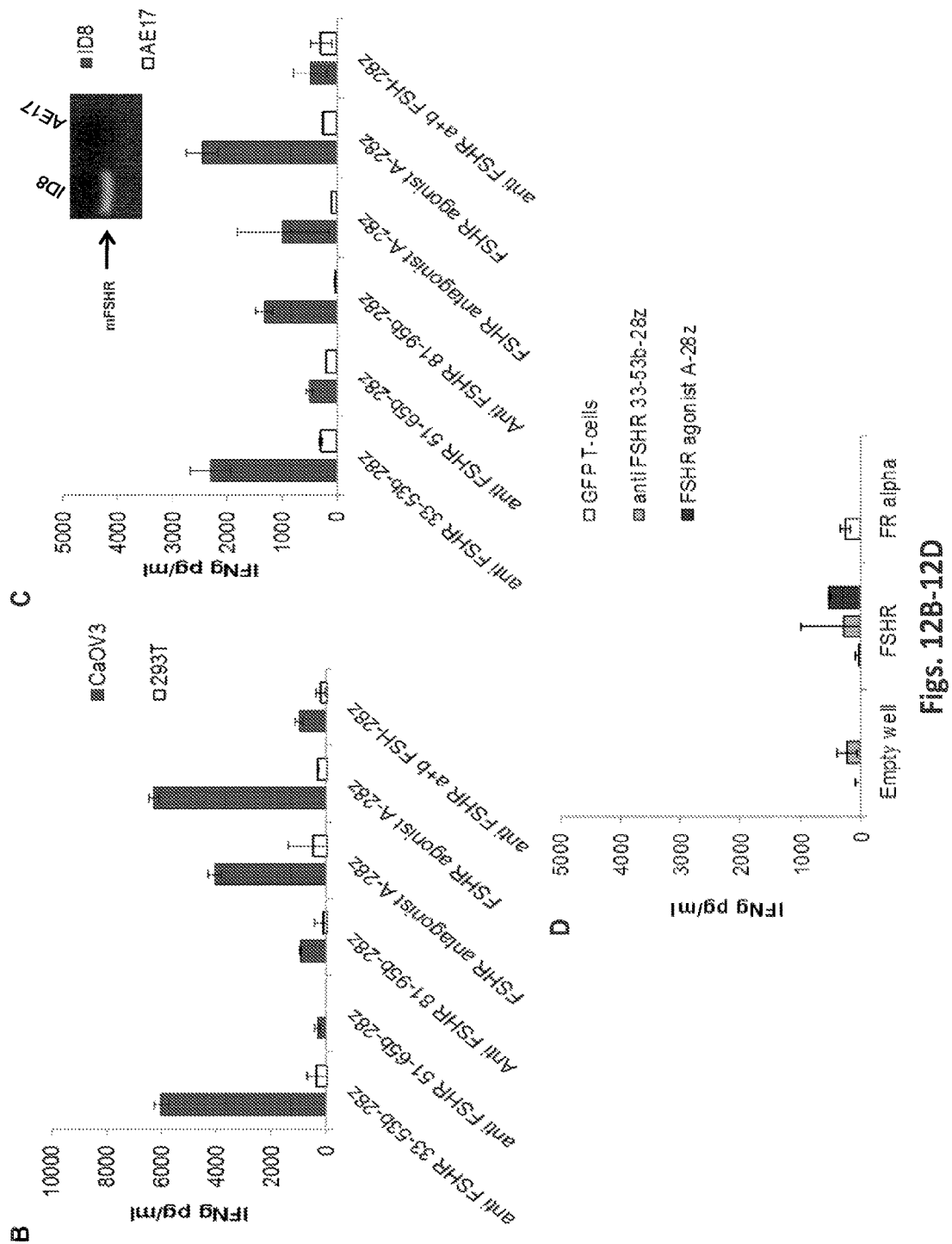
Figure 13A:
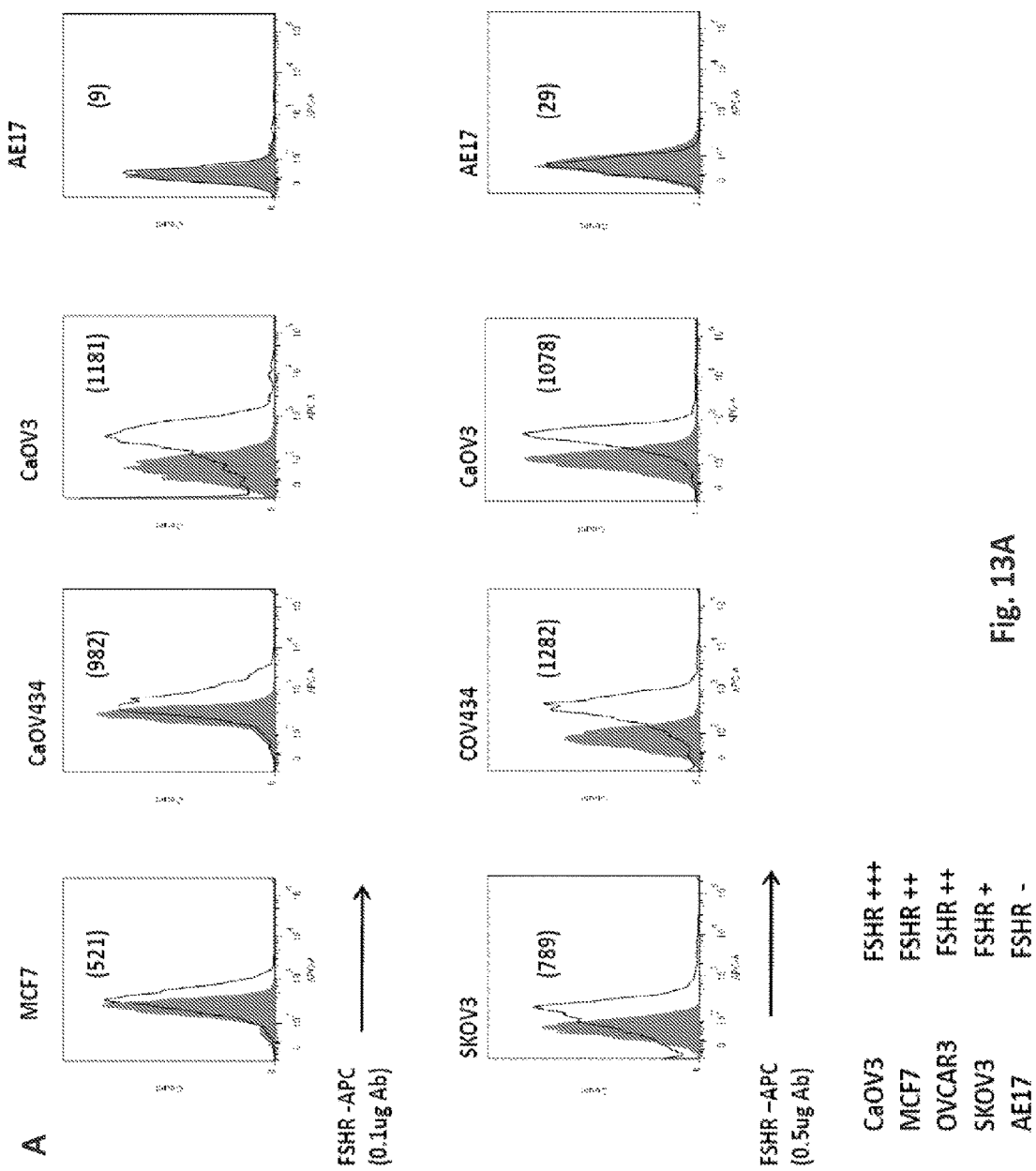
FIGS. 13A-13C are a series of graphs and an image illustrating the presence of FSHR cell surface expression on various human tumor cells.
Figure 13B:
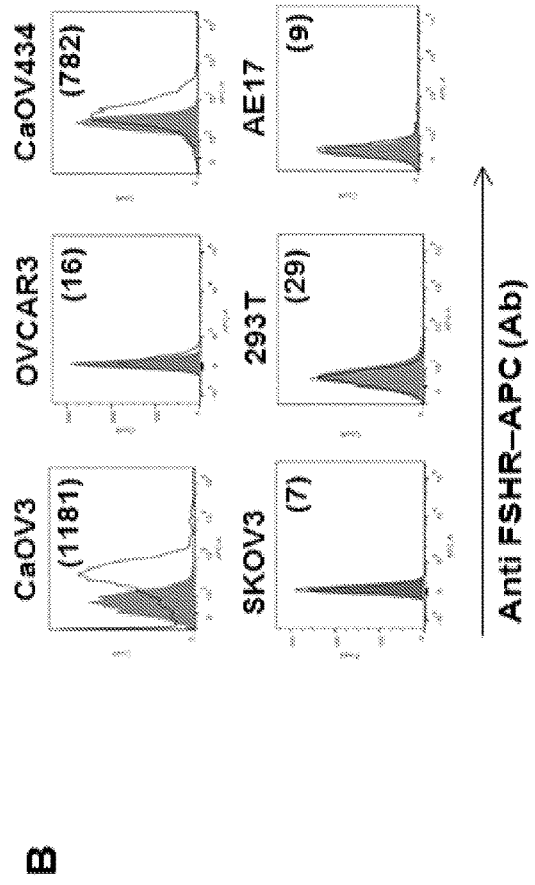
Figure 13C:
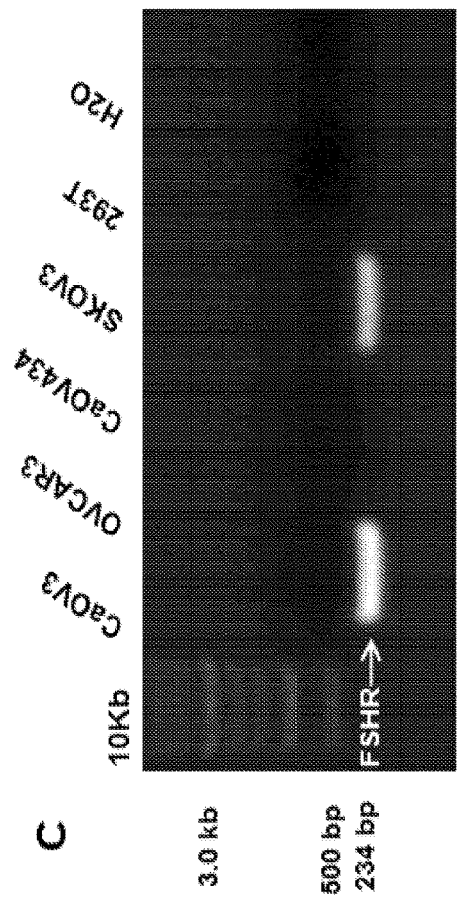
Figure 14:
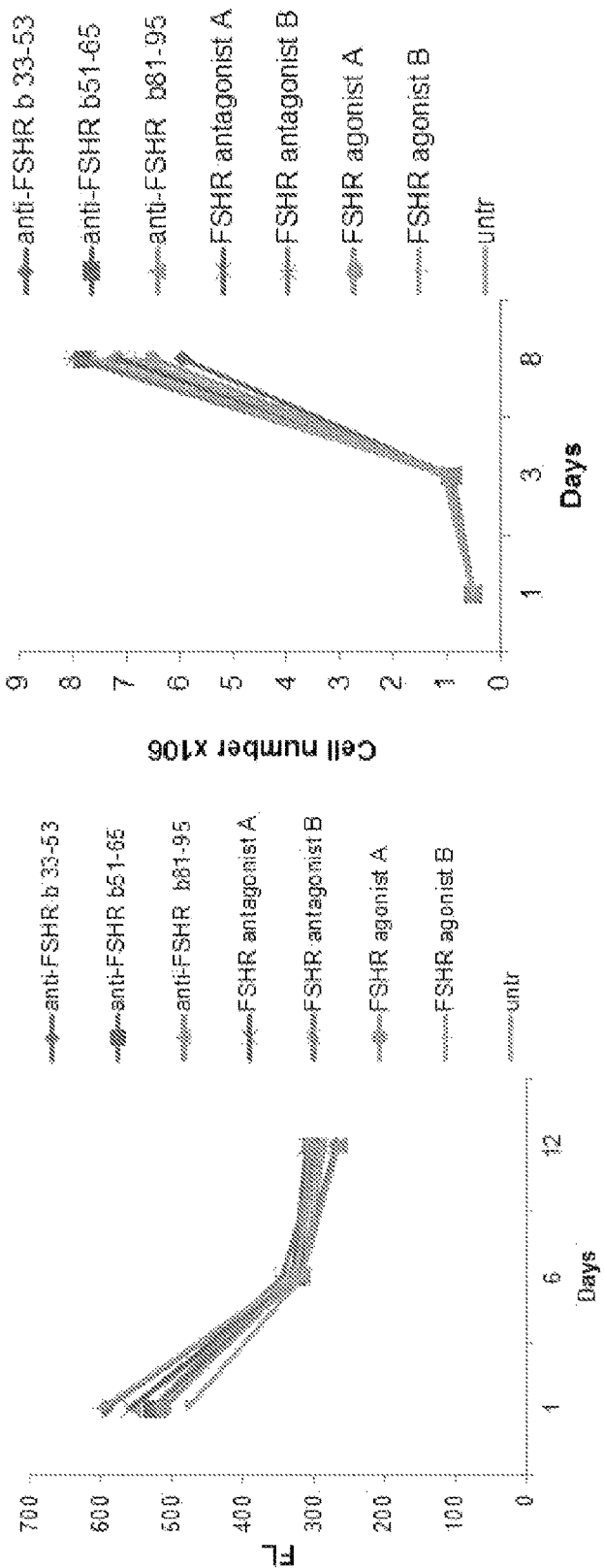
FIG. 14 encompasses graphs of cell size and cell number after stimulation and lentivirus transduction for the in vitro characterization of the anti-FSHR-28z T cells. These data demonstrate that primary human T cells transduced to express the various anti-FSHR Immune Receptors exhibit similar in vitro growth kinetics.

Example 4: Engineered FSHR Redirected T Cells Recognize Specifically FSHR and Kills Ovarian Tumor and/or Tumor Vasculature In Vitro To assess the functional reactivity of human T lymphocytes engineered to express an anti-FSHR IR, a set of anti-FSHR immune receptors were tested. The anti-FSHR immune receptors of the present invention comprising extracellularly expressed peptides derived from the FSHR natural ligand and follicle stimulating hormone (FSH) linked to intracellular T cell signaling domains (CD28 and CD3zeta), were tested for their capacity to respond to antigen expressing tumor cells in co-culture assays, through measurement of cytokine secretion (ELISA, cytokine bead array), T cell activation phenotype and specific lysis (Cr51 release assay or bioluminescence assay) (FIGS. 2, 5, 6A-6C, 7, 8A-8D and 12A-12D). A set of established human cancer cell lines were characterized for FSHR surface expression (FIGS. 13A-13C and FIG. 14). FSHR was detected on CaOV3 and CaOV434 cancer cells while OVCAR3, SKOV3 and 293T (FIG. 13B), as well as OVCAR5 and OVCAR 8, cancer cells lacked detectable FSHR expression. FSHR expression in CaOV3 and CaOv434 was confirmed by PCR utilizing RT-PCR primers (FIG. 13C). To evaluate the FSHR-specific response of anti-FSHR-IR T-cells, the panel of anti-FSHR-IR T-cells was co-cultured with FSHR-positive or FSHR-negative cells overnight, and supernatants were subsequently assayed for the secretion of IFNg cytokine. Anti-FSHR-33-53β-28z and FSHR agonist A-28z IR produced the highest levels of IFNg following a co-culture with FSHR-expressing CaOV3 or FSHR-deficient 293T cells (FIGS. 12A-12B). Interestingly, immunoreactivity did not appear associated with predicted peptide, now immobilized on the T-cell surface. First generation anti-FSHR IR-z T-cells also secreted IFNg in a similar pattern. Importantly, anti-FSHR-IR-expressing T-cells did not respond to the FSHR-deficient cell line, 293T. Similarly, when tested for immunoreactivity against the murine FSHR-expressing cell line ID8, anti-FSHR 33-53β-28z IR and FSHR agonist A-28z T-cells exhibited specific immune-recognition (FIGS. 12A-12C), consistent with the high (93%) homology between human and mouse FSHRs and known binding of human FSH, and FHS-derived peptides, to murine FHSR. This observation is of special interest, given the opportunity to address potential, but unpredicted, toxicity issues associated with targeting of FSHR in preclinical models. Notably, none of the anti-FSHR-IR constructs tested were capable of recognizing immobilized recombinant human FSHR protein produced from *e.coli* (FIG. 12D), consistent with previous reports in the art demonstrating that multiple posttranslational modifications of both FSHR and FSH are required for proper folding and binding of the ligand to the receptor (Jiang et al., PNAS 109, 12491-12496, 2012).

Figures 8A, 8B, 8C:
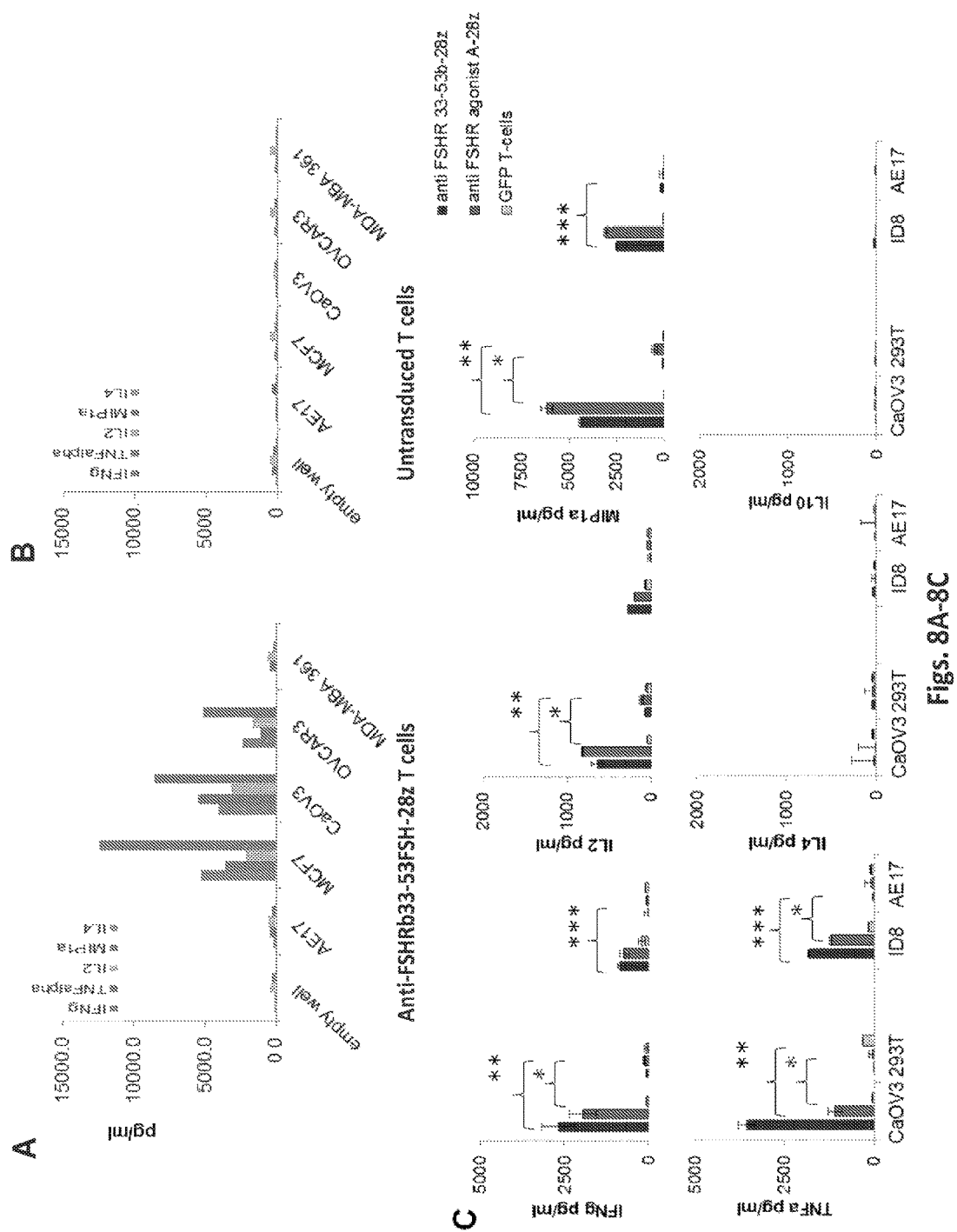
FIGS. 8A-8D, depicts the immunoreactivity of anti-FSHRb33-53-28z against human FSHR+ cancer cells. Anti-FSHR(33-53)-28z T cells (FIG. 8A), but not untransduced control T cells (FIG. 8B), produced Th1 type proinflammatory cytokines (IFN-gamma, MIP-1a and IL2) in response to encounter and stimulation with FHSR+ cancer cell lines, CaOV3, OVAR3 and MCF7, but not FSHR negative cells, AE17 and MDA361. Pooled supernatant from triplicate co-cultures were measured for proinflammatory cytokine secretion by cytokine bead assay. IFN-gamma, IL-2, TNFα, IL-4 and IL-10 cytokine concentrations (pg/ml) were measured from cultures of anti-FSHR T cells and control untransduced T-cells with target cells at the E:T ration 1:1. Representative data from 2 independent assays.
Figure 8D:
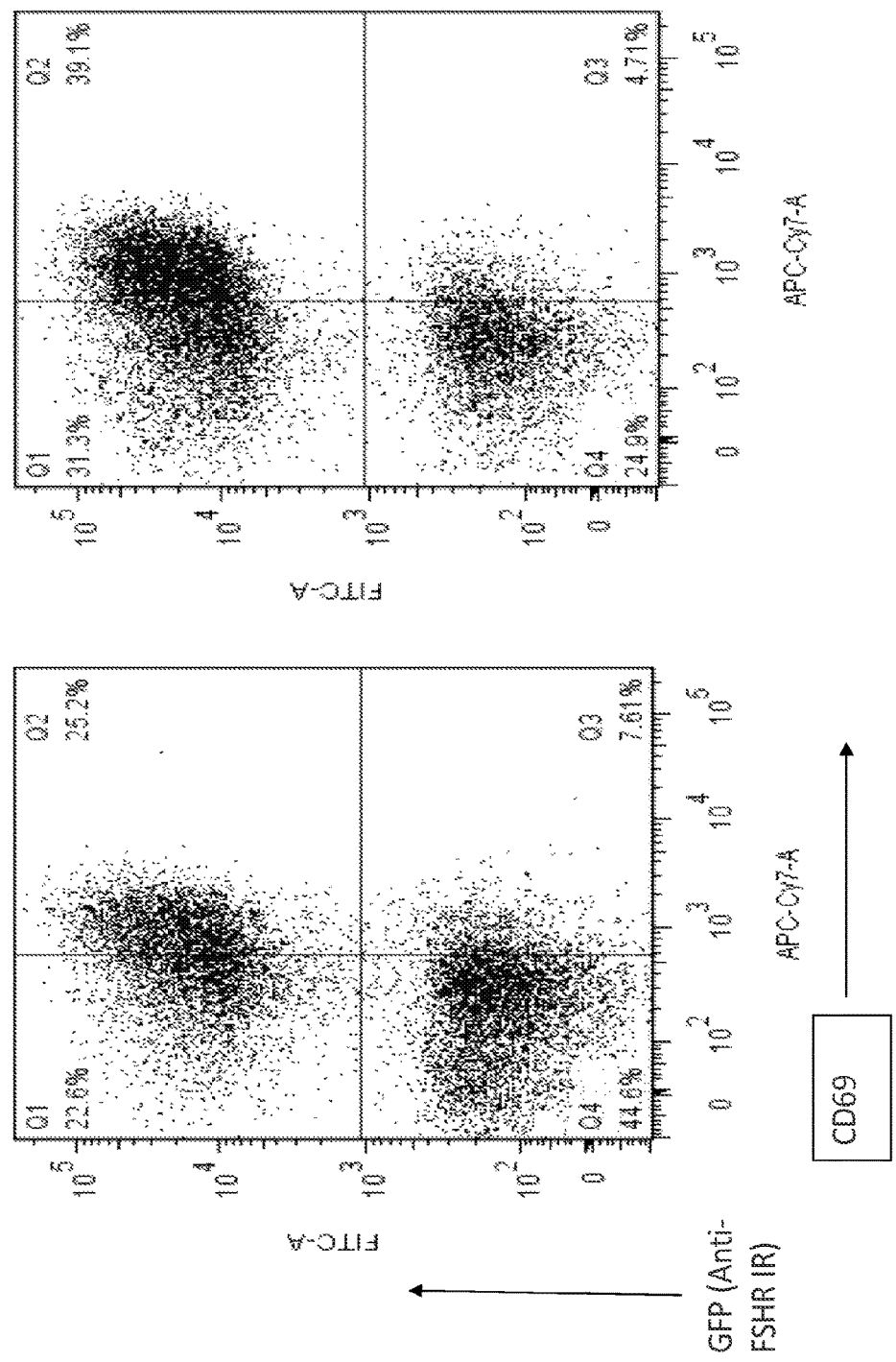
Figure 9:
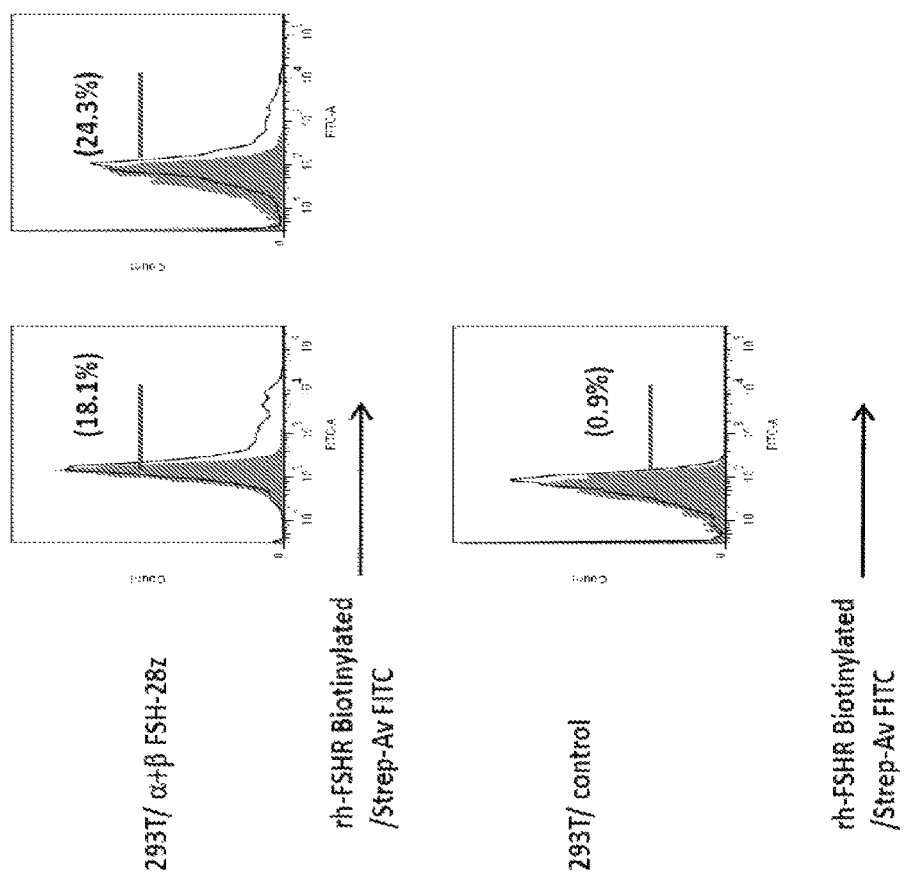
FIG. 9 shows that the anti-FSHR receptors expressed on the T cell surface have a high affinity for FSH receptor binding.

Anti-FSHR-IR constructs 33-53l and agonist-A were selected for further evaluation since they conferred the highest antigen-dependent IFNg secretion against cancer cells expressing surface FSHR. It was first determined if the engagement of anti-FSHR-IRs to its targets triggers T-cell release of other Th1 type cytokines. Both anti-FSHR 33-53β-28z and agonist A-28z IR T-cells produce more than one type of proinflammatory cytokine including TNF-alpha, MIP1-alpha and IL2, when stimulated with FSHR-expressing CaOV3 or ID8 cell lines (FIG. 8C). IFNg and TNF-alpha production was significantly lower against mouse FSHR expressed by ID8 tumor cells, with almost negligible levels of IL2 produced. This may be due to a lower affinity of the anti-FSHR-IRs towards mouse FSHR than human protein, or antigen density, as the anti-human anti-body of the present invention was unable to detect murine FSHR. However, anti-FSHR-IR T-cells did specifically upregulate expression of the activation marker CD69 in the presence of either CaOV3 or ID8, but not the FSHR-deficient cell lines, confirming reactivity against both mouse and human call lines. Control GFP or anti-FSHR 51-65b-28z T-cells did not respond to either cell line (FIG. 6A). Collectively, these data indicate that anti-FSHR-IRs confer T-cells with the capacity to specifically recognize FSHR that is expressed on the tumor cell surface.

Example 5: Anti-FSHR-IR T-Cells Mediate Antigen-Specific Tumor Cell Killing In Vitro In order to evaluate the lytic proficiency of anti-FSHR-IR T-cells T-cells, FHSR-positive and FSHR-negative target cell lines were first engineered to constitutively express firefly luciferase. Following overnight co-culture of target cells with gene-engineered T-cells, percent specific lysis was calculated based upon residual luciferase signal. Both anti-FSHR 33-53β-28 z and agonist A-28z IR T-cells showed dose-dependent lysis of FSHR-expressing targets (FIG. 6B). As observed in IFNg release assays, anti-FSHR-IR T-cells also exhibited specific lytic activity against the mouse FSHR-expressing ID8 cell line.

Figure 15:
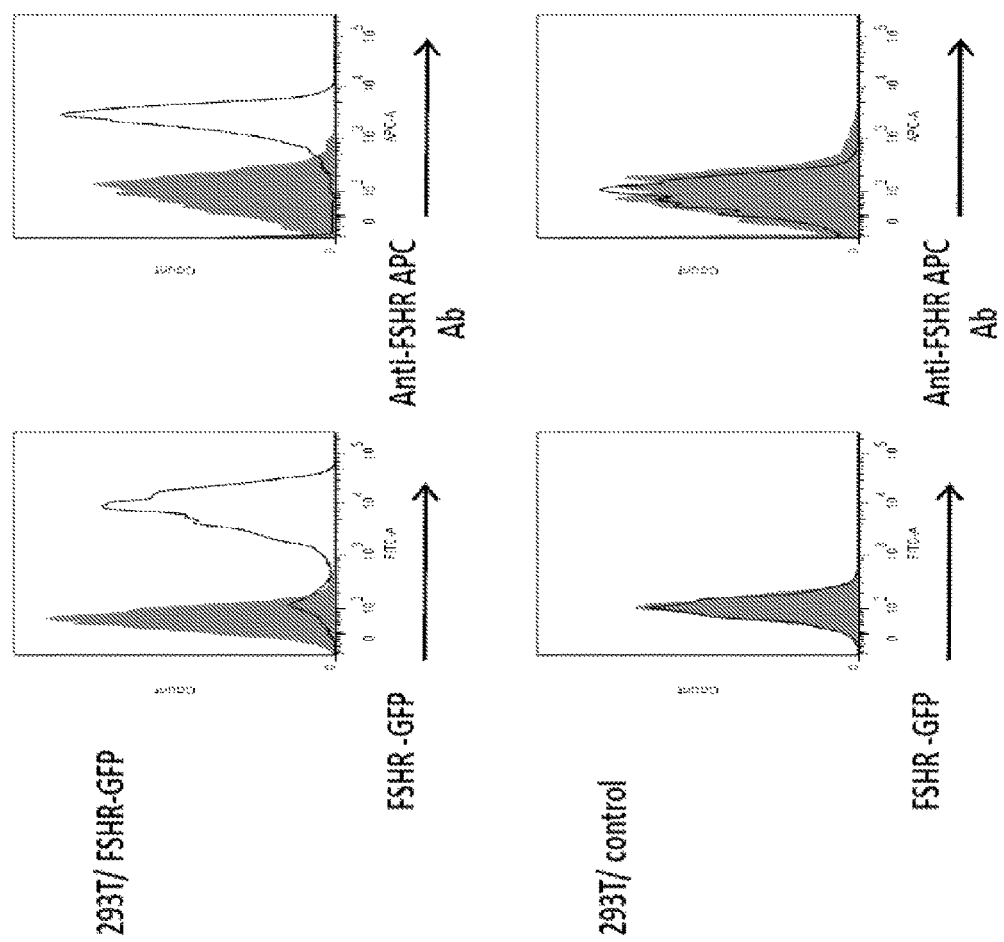
FIG. 15 is a panel of graphs showing generation of h-FSHR expressing 293T cells. 293T cells were transfected with FSHR-GFP and underwent G418 antibiotic selection. Isotype controls are shown in the filled histograms and FSHR are in the open histograms.
Figure 16:
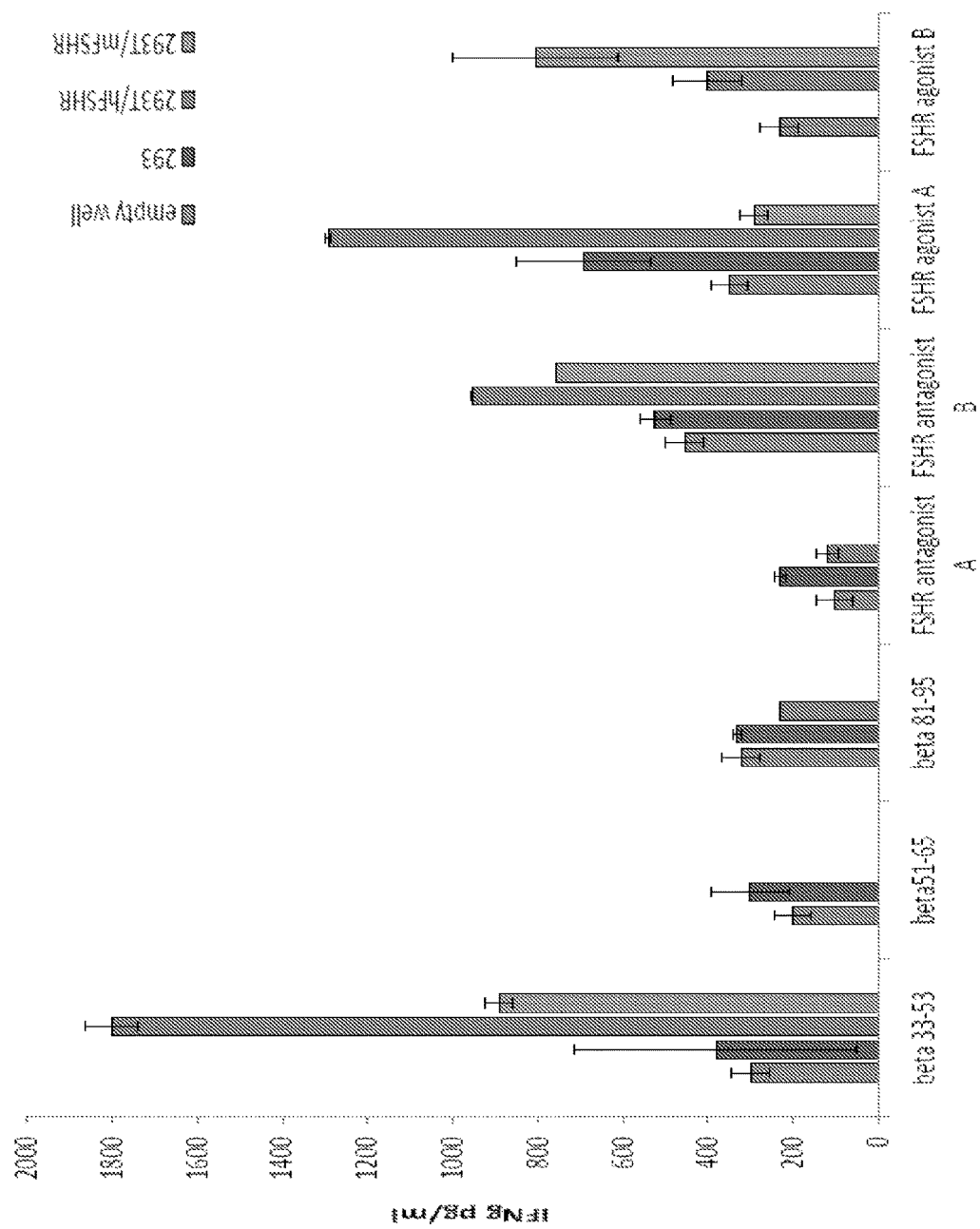
FIG. 16 is a graph showing immunoreactivity of anti-FSHR CARs against 293T cells engineered for artificial human or mouse FSHR surface expression. Anti-FSHR CAR T cells recognize artificial FSHR+293T cells and secrete IFNg but not as efficiently as when stimulated with natural FSHR expressing cancer cell lines shown in FIG. 12B.
Figure 17:
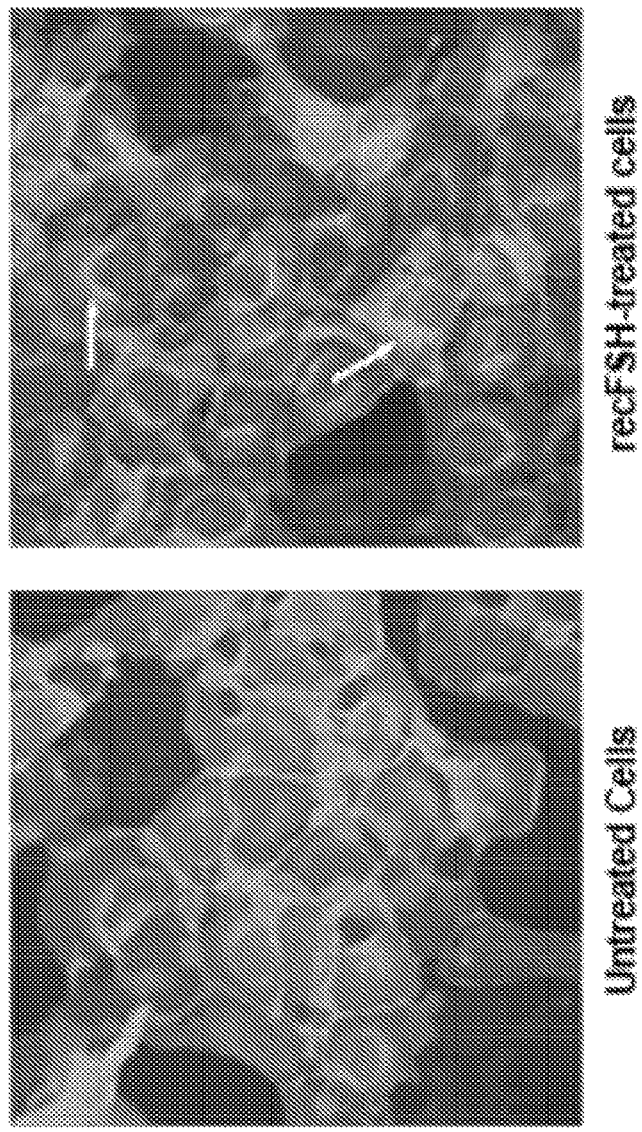
FIG. 17 is a panel of images showing GFP-tagged FSHR detection in human cells.

All anti-FSHR IRs were tested against FSHR positive and negative cells. FIG. 15 is a panel of graphs showing generation of h-FSHR expressing 293T cells. 293T cells were transfected with FSHR-GFP and underwent G418 antibiotic selection. Isotype controls are shown in the filled histograms and FSHR are in the open histograms. FIG. 16 is a graph showing immunoreactivity of anti-FSHR CARs against human and mouse cancer cell lines against artificial FSHR+ 293T cells. Artificial FSHR+293T cells binds but not as efficiently as natural FSHR expressing cancer cell lines. FIG. 17 is a panel of images showing GFP-tagged FSHR detection in human cells.

It is known in the art that some peptides derived from the beta subunits of human FSH exhibit cross-reactivity between species (Grasso et al., Biol Reprod. 58(3):821-5, 1998; Grasso P et al., Endocrinology 137:5370-5375, 1996). Therefore, anti-FSHR CARs were tested against mouse cell lines expressing mouse FSHR. This is of special interest, since it helps determining the potential for on-target toxicity of the novel FSHR-directed CAR immunotherapy in in vivo mouse model. The impact of tumor antigen expression level by target cells on the magnitude of response is assessed using FSHR-negative HEK cells engineered to express FSHR on the cell surface at high, intermediate or low levels. Untransduced T cells, T cells bearing irrelevant CARs (Mesothelin and FRa) and T cells transduced with GFP vector alone are used as controls, and are predicted not to respond to FSHR-expressing cell lines. The impact of co-stimulatory modules in anti-FSHR CARs is determined on antigen-stimulated T cell proliferation and cytokine secretion, using CFSE dilution and cytokine bead array, respectively (IFN-g, TNF-α, GM-CSF, MIP1a, IL-2, IL-4 and IL-10). In addition to establishing cell lines, the immunoreactivity of anti-FSHR T cells against primary tumors is tested. For that purpose the expression of FSHR is determined in fresh primary ovarian cancer tumor samples as well in ascites. Additionally, immunohistochemistry is performed on a tissue microarray containing primary ovarian cancer specimens. The array is analyzed to determine the percentage of FSHR+ positive vessels from each tumor core, and also the intensity of staining. Flow cytometry is used to confirm the expression of FSHR on patient derived tumor endothelial cells, analyzing in parallel co-expression of FSHR with CD31, CD34 and VEGFR2 on tumor endothelial cells. Low levels of FSHR expression on monocytes and osteoclasts is not clearly established in the art (Robinson et al., Biochem Biophys Res Commun. 2010 Mar. 26; 394(1): 12-7). In order to address a potential risk for on-target tissue toxicity against these normal cells, the immunoreactivity of FSHR redirected T cells is also investigated against human and mouse monocytes, in conventional co-culture assays. All the above assays are performed in triplicate and statistical significance determined using appropriate tests.

Example 6: In Vivo Evaluation of the Potency of Anti-FSHR Engineered T Cells

The current invention provides a targeted anti-cancer therapy that affects tumor growth in a direct and indirect manner, by targeting tumor cells and/or tumor vasculature. First, the antitumor effect of targeting exclusively tumor vasculature is validated comparing to simultaneous targeting of tumor vasculature and tumor cells. To assess the antitumor effect of anti-FSHR IR T cells, human endothelium xenografts are established in the NSG (NOD/SCID/γc−/−) mouse model by injection of ovarian cancer cells mixed with immortalized endothelial cells stably expressing FSHR subcutaneously into the flank. A xenogeneic model of ovarian cancer is exploited using FSHR negative human ovarian cancer cell line, A1847 with FSHR-positive and/or -negative tumor endothelial cells. NSG mice are injected in the flank with 50% Matrigel containing $3 \times 10^6$ tumor cells and $0.5 \times 10^6$ endothelial cells (MS1). In parallel, the anti-tumor efficacy of anti-FSHR IRs is tested when both the tumor and vasculature express FSHR by utilizing the A1847 cell line engineered to stably express FSHR in a model similar to that described above in detail.

Anti-tumor response is routinely monitored by caliper sizing and bioluminescence imaging. Anti-FSHR IR T cells or controls are administered i.v. at $5 \times 10^6$ cell doses to mice bearing tumor (≥200 mm3). Because objective clinical response to IR based therapy is correlated with the persistence of IR+T cells after infusion, peripheral blood is collected weekly from treated mice and measured for the continued persistence of human T cells in vivo via TruCount bead-based counting. Since, the novel anti-FSHR IRs of this invention may recognize mouse FSHR, the biodistribution of anti-FSHR IR T cells follows intravenous administration in treated mice. The expression of FSHR on tumor cells or tumor ECs surface is confirmed by immunohistochemistry analysis, as well as flow cytometry (FACS) of single cell suspensions achieved by enzyme-digestion. Accordingly, to validate FSHR expression on tumor blood vessels by FACS, the expression of FSHR is assessed in samples labeled in parallel with antibodies recognizing endothelial cell markers CD31 and CD33, as well as EpCAM as a tumor associated antigen.

Given the current knowledge in the art on high homology between mouse and human FSH and positive response of mice to treatment with either human FSH or FSH derived ligands (Grasso et al., Biol Reprod. 58(3):821-5, 1998), the IR of the present invention is suitable for testing novel anti-FSHR chimeric immune receptor therapy in a syngeneic models of mouse ovarian cancer. Specifically, tumors established by subcutaneously injecting mouse ovarian cancer cell line, ID8 (FSHR positive) are investigated for their capacity of generating tumor blood vessels. The expression of the mouse FSHR is assessed by immunochemistry as well as flow cytometry, utilizing antibodies recognizing mouse FSHR, CD35, EpCam. All experiments include 10 mice per group, and confirmatory mouse studies are conducted to determine reproducibility.

Example 7: FSHR-Redirected Primary Human T-Cells Suppress Tumor Growth In Vivo

Figure 18:
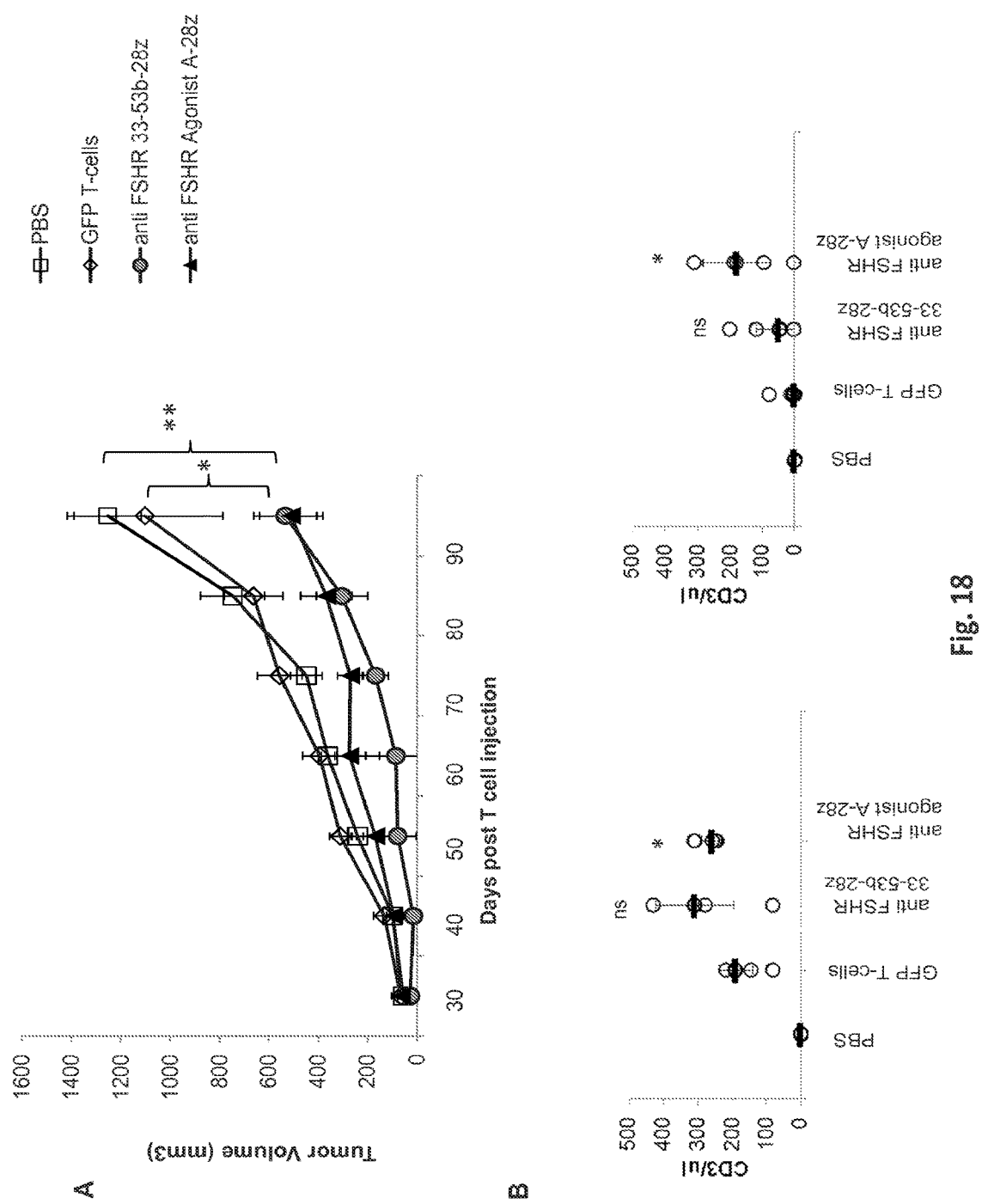
FIGS. 18A-18B are a series of graphs depicting the differential ovarian cancer tumor growth in mice receiving treatment.

To assess the anti-tumor effect of anti-FSHR T-cells in vivo, human ovarian cancer xenografts were established in NOD/SCID/IL2Rγ−/− (NSG) mice by subcutaneous flank injection of CaOV3 cancer cell line followed by two intravenous injections of gene-engineered T-cells at days 20 and 25. Consistent with their in vitro function, both anti-FSHR-33-53β-28z and agonist A-28z IR T-cells mediated the suppression of established tumor outgrowth that was statistically superior to the control, GFP-engineered T-cell treated group, which provided no benefit (FIG. 18A). These data suggest that systemic delivery of anti-FSHR 33-53β-28z or agonist-28z IR T-cells to mice bearing FSHR-expressing tumors may result in tumor trafficking, activation, and lysis at location of tumor. Because objective clinical response to T-cell transfer therapy is often associated with the persistence of T-cells after infusion (Robbins et al., Journal of immunology 173, 7125-7130, 2004), peripheral blood was measured for the continued persistence of engineered human T-cells in vivo via TruCount bead-based counting (FIG. 18B). Consistent with the anti-tumor response, mice treated with anti FSHR-33-53β-28z and agonist A-28z IR T-cells had increased peripheral blood CD3+ T-cell counts compared to controls at three and five weeks post-T-cell infusion, though only at the level of statistical significance in the agonist A-28z-IR T-cell group. No overt immune-related toxicity or immunopathology was observed.

In summary, the present invention successfully exploited a novel therapeutic antigen, the FSHR protein, expressed on the tumor cell surface, to deliver T-cell based immunetherapy of cancer. Given its highly restricted, abundant expression in cancer, cancer-associated vessels and gonadal tissues, the rationale for FSHR targeting in solid human malignancy is strong. Possible risks associated with on target/off tissue toxicities appear limited. FSHR-deficient mice are vital but infertile with decreased size of ovaries and uterus (Dierich et al., PNAS 95, 13612-13617, 1998), suggesting possible toxicities may be restricted to reproductive organs. However, in the scenario of a patient diagnosed with ovarian cancer, these organs are virtually non-essential and often surgically removed. In contrast, male FSHRKO mice exhibit reduced numbers of spermatocytes, and would suggest possible targeted toxicity against testis, an immune privileged organ (Abel et al., Endocrinology 149, 3279-3285, 2008). The present invention demonstrates that anti-FSHR IR T-cells are capable of targeting and killing FSHR-expressing cancer cells, resulting in significant suppression of FSHR-expressing tumor outgrowth in vivo. The findings herein warrant the examination of other molecules for FSHR targeting to create higher affinity anti-FSHR chimeric immunoreceptors. Further, the activity of peptide-based anti-FSHR IRs may also be improved by optimization of other components of the immunoreceptor. For instance, modification of the hinge length may significantly improve the affinity of peptide or scFv based immunoreceptors (Hudecek et al., Cancer immunology research, 2014). Moving forward, it will be important to test this FSHR-targeted therapy in tumor models where FSHR is exclusively expressed by tumor blood vessels, compared to simultaneous expression on both tumor cells and its associated vasculature. This present invention is of a special interest and has great potential for application in not only ovarian cancer but across many solid cancer types.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

Relevant Sequences for the Present Invention:
Sequences for Anti-FSHR IRs (Extracellular Portion of Anti-FSHR IR)

Anti-FSHRb33-53FSH-28z (β33-53, Amino acid sequence)(SEQ ID NO: 1)
YTRDLVYKDPARPKIQKTCTF Anti-FSHRb51-65FSH-28z (β51-65, Amino acid sequence) (SEQ ID NO: 2)
CTFKELVYETVRVPGC Anti-FSHRb51-65FSH-28z (β81-95, Amino acid sequence) (SEQ ID NO: 3)
QCHCGKCDSDSTDCT Anti-FSHRantagonistA-28Z (Antagonist A β3(87-94 aa) + α(25-42 aa), Amino acid sequence) (SEQ ID NO: 4)
CDSDSTDCILQCMGCCFSRAYPTPLR Anti-FSHRantagonistA-28Z (Agonist A β(87-94 aa) + α(25-42 aa) + β(27-45 aa), Amino acid sequence) (SEQ ID NO: 5)
CDSDSTDCILQCMGCCFSRAYPTPLRWCAGYCYCYTRDVKDPARP Anti-FSHR peptide 33-53
Nucleotide sequence (SEQ ID NO: 6):
TACACCAGGGATCTGGTGTATAAGGACCCAGCCAGGCCCAAAATCCAGAA

AACATGT

Amino acid sequence (SEQ ID NO: 7):
YTRDLVYKDPARPKIQKTC

Anti-FSHR peptide 51-65
Nucleotide sequence (SEQ ID NO: 8):
AAAACATGTACCTTCAAGGAACTGGTATACGAAACAGTGAGAGTG Amino acid sequence SEQ ID NO: 9):
KTCTFKELVYETVRV FSHR peptide 81-95
Nucleotide sequence (SEQ ID NO: 10):
GGATCCCAGTGTCACTGTGGCAAGTGTGACAGCGACAGCACTGATTGTAC

TGCTAGC

Amino acid sequence (SEQ ID NO: 11):
GSQCHCGKCDSDSTDCTAS

FSHR antagonist A
Nucleotide sequence (SEQ ID NO: 12):
GATCCTGCGATAGCGATAGCACCGATTGCATTCTGCAGTGCATGGGCTGC

TGCTTTAGCCGCGCGTATCCGACCCCGCTGCGCGCTAGC

Amino acid sequence (SEQ ID NO: 13):
GSCDSDSTDCILQCMGCCFSRAYPTPLRAS

FSHR antagonist B sequence:
Nucleotide sequence (SEQ ID NO: 14):
GGATCCCGCCTGCCGACCCCGTATGCGCGCAGCTTTTGCTGCGGCATGTG

CCAGCTGATTTGCGATACCAGCGATAGCGATTGCGCTAGC

Amino acid sequence (SEQ ID NO: 15):
GSRLPTPYARSFCCGMCQLICDTSDSDCAS

Anti-FSHR agonist A BamHI/PstI to NheI
Agonist' A
Nucleotide sequence (SEQ ID NO: 16):
GGATC CTGCG ATAGC GATAG CACCG ATTGC ATTCT GCAGT

GCATG GGCTG CCTAG GACGC TATCG CTATC GTGGC TAACG

TAAGA CGTCA CGTAC CCGAC CTGCT TTAGC CGCGC GTATC

CGACC CCGCT GCGCT GGTGC GCGGG CTATT GACGA AATCG

GCGCG CATAG CTGG GGCGA CGCGA CCACG CGCCC GATAA

GCTAT TGCTA TACCC GCGAT CTGGT GAAAG ATCCG GCGCG

CCCGG CTAGC CGATA ACGAT ATGGG CGCTA GACCA CTTTC

TAGGC CGCGC GGGCC GATCG

Amino acid sequence (SEQ ID NO: 17):
GSCDSDSTDCILQCMGCCFSRAYPTPLRWCAGYCYCYTRDLVKDPARPAS Anti-FSHR agonist B BamHI to NheI
Nucleotide sequence (SEQ ID NO: 18):
CCCGC GCGCG CCGGA TAAAG TGCTG GATCG CACCT ATTGC

TATTG CCTAG GGGCG CGCGC GGCCT ATTTC ACGAC CTAGC

GTGGA TAACG ATAAC CTATG GCGCG TGCTG GCGCC TGCCG

ACCCC GTATG CGCGC AGCTT TTGCT GATAC CGCGC ACGAC

CGCGG ACGGC TGGGG CATAC GCGCG TCGAA AACGA GCGGC

ATGTG CCAGC TGATT TGCGA TACCA GCGAT AGCGA TTGCG

CTAGC CGCCG TACAC GGTCG ACTAA ACGCT ATGGT CGCTA

TCGCT AACGC GATCG

Amino acid sequence (SEQ ID NO: 19):
PRAPDKVLDRTYCYCYGACWRLPTPYARSFCCGMCQLICDTSDSDC Anti FSHR peptide Alpha + beta chain (linear FSH)
BamHI to NheI Nucleotide sequence (SEQ ID NO: 20):
GGATCCA ACAGCTGCGA ACTGACCAAC ATTACCATTG

CGATTGAAAA AGAAGAATGC CGCTTTTGCA TTAGCATTAA

CACCACCTGG TGCGCGGGCT ATTGCTATAC CCGCGATCTG

GTGTATAAAG ATCCGGCGCG CCCGAAAATT CAGAAAACCT

GCACCTTTAA AGAACTGGTG TATGAAACCG TGCGCGTGCC

GGGCTGCGCG CATCATGCGG ATAGCCTGTA TACCTATCCG

GTGGCGACCC AGTGCCATTG CGGCAAATGC GATAGCGATA

GCACCGATTG CACCGTGCGC GGCCTGGGCC CGAGCTATTG

CAGCTTTGGC GAAATGAAAG AAGCGCCGGA TGTGCAGGAT

TGCCCGGAAT GCACCCTGCA GGAAAACCCG TTTTTTAGCC

AGCCGGGCGC GCCGATTCTG CAGTGCATGG GCTGCTGCTT

TAGCCGCGCG TATCCGACCC CGCTGCGCAG CAAAAAAACC

ATGCTGGTGC AGAAAAACGT GACCAGCGAA AGCACCTGCT

GCGTGGCGAA AAGCTATAAC CGCGTGACCG TGATGGGCGG

CTTTAAAGTG GAAAACCATA CCGCGTGCCA TTGCAGCACC

TGCTATTATC ATAAAAGCGC TAGC

Amino acid sequence (SEQ ID NO: 21):
GSNSCELTNITIAIEKEECRFCISINTTWCAGYCYTRDLVYKDPARPKIQ

KTCTFKELVYETVRVPGCAHHADSLYTYPVATQCHCGKCDSDSTDCTVRG

LGPSYCSFGEMKEAPDVQDCPECTLQENPFFSQPGAPILQCMGCCFSRAY

PTPLRSKKTMLVQKNVTSESTCCVAKSYNRVTVMGGFKVENHTACHCSTC

YYHKSAS

Sequences of Anti-FSHR IR: CD8alpha Hinge; Trans-Membrane Region TM CD8 or CD28; Intracellular Signaling Domains.

CD8 alpha Hinge
Nucleotide sequence (SEQ ID NO: 22):
ACCACG ACGCCAGCGC CGCGACCACC AACACCGGCG CCCACCATCG

CGTCGCAGCC CCTGTCCCTG CGCCCAGAGG CGTGCCGGCC

AGCGGCGGGG GGCGCAGTGC ACACGAGGGG GCTGGACTTC

GCCTGTGAT

Amino acid sequence (SEQ ID NO: 23):
TTTPAPRPPTPAPTIASQPLSLRPEACRPAAGGAVHTRGLDFACD CD28 Transmembrane Domain
Nucleotide sequence (SEQ ID NO: 24):
T TTTGGGTGCT GGTGGTGGTT GGTGGAGTCC TGGCTTGCTA

TAGCTTGCTA GTAACAGTGG CCTTTATTAT TTTCTGGGTG

Amino acid sequence (SEQ ID NO: 25):
FWVLVVVGGVLACYSLLVTVAFIIFWV

CD8hinge/CD8TM
Nucleotide sequence (SEQ ID NO: 26):
ACCACGACGC CAGCGCCGCG ACCACCAACA CCGGCGCCCA

CCATCGCGTC GCAGCCCCTG TCCCTGCGCC CAGAGGCGTG

CCGGCCAGCG GCGGGGGGCG CAGTGCACAC GAGGGGGCTG

GACTTCGCCT GTGATATCTA CATCTGGGCG CCCTTGGCCG

GGACTTGTGG GGTCCTTCTC CTGTCACTGG TTATCACCCT

TTACTGC

Amino acid sequence (SEQ ID NO: 27):
TTTPAPRPPTPAPTIASQPLSLRPEACRPAAGGAVHTRGLDFACDIYIWA

PLAGTCGVLLLSLVITLYC

Signaling domains;
CD28
Nucleotide sequence (SEQ ID NO: 28):
AGGAGTAAGA GGAGCAGGCT CCTGCACAGT GACTACATGA

ACATGACTCC CCGCCGCCCC GGGCCCACCC GCAAGCATTA

CCAGCCCTAT GCCCCACCAC GCGACTTCGC AGCCTATCGC TCC

Amino acid sequence (SEQ ID NO: 29):
RSKRSRLLHSDYMNMTPRRPGPTRKHYQPYAPPRDFAAYRS

CD3Z
Nucleotide sequence (SEQ ID NO: 30):
A GAGTGAAGTT CAGCAGGAGC GCAGACGCCC CCGCGTACCA

GCAGGGCCAG AACCAGCTCT ATAACGAGCT CAATCTAGGA

CGAAGAGAGG AGTACGATGT TTTGGACAAG AGACGTGGCC

GGGACCCTGA GATGGGGGGA AAGCCGAGAA GGAAGAACCC

TCAGGAAGGC CTGTACAATG AACTGCAGAA AGATAAGATG

GCGGAGGCCT ACAGTGAGAT TGGGATGAAA GGCGAGCGCC

GGAGGGGCAA GGGGCACGAT GGCCTTTACC AGGGTCTCAG

TACAGCCACC AAGGACACCT ACGACGCCCT TCACATGCAG

GCCCTGCCCC CTCGCTAA

Amino acid sequence (SEQ ID NO: 31):
RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR

TABLE 1

Sequence listing

| SEQ ID NO: | Description | Type |
|---|---|---|
| 1 | Anti-FSHRb33-53FSH-28z | Amino acid |
| 2 | Anti-FSHRb51-65FSH-28z | Amino acid |
| 3 | Anti-FSHRb51-65FSH-28z | Amino acid |
| 4 | Anti-FSHRantagonistA-28Z | Amino acid |
| 5 | Anti-FSHRantagonistA-28Z | Amino acid |
| 6 | Anti-FSHR peptide 33-53 | Nucleic acid |
| 7 | Anti-FSHR peptide 33-53 | Amino acid |
| 8 | Anti-FSHR peptide 51-65 | Nucleic acid |
| 9 | Anti-FSHR peptide 51-65 | Amino acid |
| 10 | FSHR peptide 81-95 | Nucleic acid |
| 11 | FSHR peptide 81-95 | Amino acid |
| 12 | FSHR antagonist A | Nucleic acid |
| 13 | FSHR antagonist A | Amino acid |
| 14 | FSHR antagonist B sequence | Nucleic acid |
| 15 | FSHR antagonist B sequence | Amino acid |
| 16 | Anti-FSHR agonist A BamHI/PstI to NheI | Nucleic acid |
| 17 | Anti-FSHR agonist A BamHI/PstI to NheI | Amino acid |
| 18 | Anti-FSHR agonist B BamHI to NheI | Nucleic acid |
| 19 | Anti-FSHR agonist B BamHI to NheI | Amino acid |

TABLE 1-continued

Sequence listing

| SEQ ID NO: | Description | Type |
|---|---|---|
| 20 | Anti FSHR peptide Alpha + beta chain (linear FSH) BannHI to NheI | Nucleic acid |
| 21 | Anti FSHR peptide Alpha + beta chain (linear FSH) BamHI to NheI | Amino acid |
| 22 | CD8 alpha Hinge | Nucleic acid |
| 23 | CD8 alpha Hinge | Amino acid |
| 24 | CD28 Transmembrane Domain | Nucleic acid |
| 25 | CD28 Transmembrane Domain | Amino acid |
| 26 | CD8hinge/CD8TM | Nucleic acid |
| 27 | CD8hinge/CD8TM | Amino acid |
| 28 | CD28 | Nucleic acid |
| 29 | CD28 | Amino acid |
| 30 | CD3Z | Nucleic acid |
| 31 | CD3Z | Amino acid |
| 32 | human-FSHR primer | Nucleic acid |
| 33 | human-FSHR primer | Nucleic acid |
| 34 | mouse-FSHR primer | Nucleic acid |
| 35 | mouse-FSHR primer | Nucleic acid |

What is claimed:

1. An isolated nucleic acid sequence encoding a follicle-stimulating hormone receptor (FSHR) binding immunoreceptor (IR) comprising a FSHR binding domain, a transmembrane domain, and a signaling domain, wherein the FSHR binding domain comprises a follicle-stimulating hormone (FSH) or fragment thereof, a FSHR antagonist or fragment thereof, or an anti-FSHR agonist or fragment thereof, wherein the FSHR binding domain is encoded by a nucleic acid sequence selected from the group consisting of SEQ ID NOs: 10, 12, 14, 16, 18 and 20.

2. The isolated nucleic acid sequence of claim 1, wherein the transmembrane domain comprises a CD8alpha hinge and transmembrane domain.

3. The isolated nucleic acid sequence of claim 1, wherein the signaling domain comprises a CD3 signaling domain.

4. The isolated nucleic acid sequence of claim 1, wherein the FSHR binding IR further comprises a costimulatory signaling region comprising an intracellular domain selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, a ligand that specifically binds with CD83, and any combination thereof.

5. The isolated nucleic acid sequence of claim 1, wherein the FSHR binding IR specifically binds to FSHR expressed by tumor cells and/or tumor vasculature.

6. A vector comprising the isolated nucleic acid sequence of claim 1.

7. A modified cell comprising the vector of claim 6.

8. A modified cell comprising the nucleic acid sequence of claim 1.

9. The cell of claim 8, wherein the FSHR binding IR specifically binds to FSHR expressed by tumor cells and/or tumor vasculature.

10. The cell of claim 9, wherein the tumor cells are from a cancer selected from the group consisting of ovarian cancer, renal cell carcinoma, bladder cancer, kidney cancer, testicular cancer, prostate cancer, breast cancer, colon cancer, pancreatic cancer, lung cancer, liver cancer, stomach cancer and any combination thereof.

11. The cell of claim 8, wherein the cell is selected from the group consisting of a T cell, a natural killer (NK) cell, a cytotoxic T lymphocyte (CTL), and a regulatory T cell.

12. A composition comprising the modified cell of claim 8.

* * * * *